(12) United States Patent
Korennykh et al.

(10) Patent No.: US 8,980,899 B2
(45) Date of Patent: Mar. 17, 2015

(54) METHODS OF INHIBITING IRE1

(75) Inventors: Alexei Korennykh, Princeton, NJ (US); Peter Walter, San Francisco, CA (US); Han Li, Redwood City, CA (US); Arvin Dar, San Francisco, CA (US); Kevan Shokat, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 106 days.

(21) Appl. No.: 13/502,307

(22) PCT Filed: Oct. 18, 2010

(86) PCT No.: PCT/US2010/053072
§ 371 (c)(1),
(2), (4) Date: Sep. 6, 2012

(87) PCT Pub. No.: WO2011/047384
PCT Pub. Date: Apr. 21, 2011

(65) Prior Publication Data
US 2012/0322814 A1    Dec. 20, 2012

Related U.S. Application Data

(60) Provisional application No. 61/252,230, filed on Oct. 16, 2009.

(51) Int. Cl.
*A01N 43/90* (2006.01)
*A61K 31/519* (2006.01)

(52) U.S. Cl.
CPC .................................. *A61K 31/519* (2013.01)
USPC ........................................ 514/257; 514/262.1

(58) Field of Classification Search
USPC ................................................. 514/257, 262.1
See application file for complete search history.

(56) References Cited

U.S. PATENT DOCUMENTS

| | | | |
|---|---|---|---|
| 4,704,381 A | 11/1987 | Schaumann et al. |
| 4,861,760 A | 8/1989 | Mazuel et al. |
| 4,911,920 A | 3/1990 | Jani et al. |
| 5,212,162 A | 5/1993 | Missel et al. |
| 5,240,941 A | 8/1993 | Bruneau |
| 5,310,731 A | 5/1994 | Olsson et al. |
| 5,364,862 A | 11/1994 | Spada et al. |
| 5,403,841 A | 4/1995 | Lang et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |

(Continued)

FOREIGN PATENT DOCUMENTS

| CA | 1338379 | 6/1996 |
|---|---|---|
| CN | 101602768 | 12/2009 |

(Continued)

OTHER PUBLICATIONS

Sheridan RP. "The Most Common Chemical Replacements in Drug-Like Compounds". J. Chem. Inf. Comput. Sci. 2002, 42, 103-108.*
Cannon JG. "Analog Design". Burger's Medicianl Chemistry and Drug Discovery, Fifth Edition, vol. 1: Principles and Practice, 1995, pp. 783-802.*
"Report of the Expert Committee on the Diagnosis and Classification of Diabetes Mellitus", *Diabetes Care* (1992) 2(Suppl 1):S5-S19.

(Continued)

*Primary Examiner* — Renee Claytor

(74) *Attorney, Agent, or Firm* — Kilpatrick Townsend & Stockton LLP

(57) ABSTRACT

Disclosed herein are, inter alia, methods for inhibiting Ire1 activity.

16 Claims, 6 Drawing Sheets

(56) References Cited

U.S. PATENT DOCUMENTS

| | | |
|---|---|---|
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Tanaka et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Ono et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 2001/0019829 A1 | 9/2001 | Nelson |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |

(56) References Cited

U.S. PATENT DOCUMENTS

| | | |
|---|---|---|
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0264423 A2 | 1/2009 | Cheung et al. |
| 2009/0053192 A1 | 2/2009 | Milian et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |

FOREIGN PATENT DOCUMENTS

| | | | |
|---|---|---|---|
| EP | 773023 | A1 | 5/1997 |
| EP | 1020445 | B1 | 8/2008 |
| GB | 812366 | | 4/1959 |
| GB | 937725 | | 9/1963 |
| JP | 61109797 | | 5/1986 |
| JP | 5256693 | | 10/1993 |
| JP | 8295667 | A | 11/1996 |
| JP | 9143163 | A | 6/1997 |
| JP | 10206995 | A | 8/1998 |
| JP | 2000072773 | A | 3/2000 |
| JP | 2002037787 | A | 2/2002 |
| JP | 2002131859 | A2 | 5/2002 |
| JP | 2003073357 | A2 | 3/2003 |
| JP | 2004161716 | A | 6/2004 |
| WO | WO83/01446 | A1 | 4/1983 |
| WO | WO91/17161 | A1 | 11/1991 |
| WO | WO92/14733 | A1 | 9/1992 |
| WO | WO93/16091 | A1 | 8/1993 |
| WO | WO93/16092 | A1 | 8/1993 |
| WO | WO93/18035 | A1 | 9/1993 |
| WO | WO93/22443 | A1 | 11/1993 |
| WO | WO94/13677 | A1 | 6/1994 |
| WO | WO94/17803 | A1 | 8/1994 |
| WO | WO95/12588 | A1 | 5/1995 |
| WO | WO95/29673 | A1 | 11/1995 |
| WO | WO95/32984 | A1 | 12/1995 |
| WO | WO96/40706 | A1 | 12/1996 |
| WO | WO97/15658 | A1 | 5/1997 |
| WO | WO97/28133 | A1 | 8/1997 |
| WO | WO97/28161 | A1 | 8/1997 |
| WO | WO98/41525 | A1 | 9/1998 |
| WO | WO98/52611 | A1 | 11/1998 |
| WO | WO98/57952 | A1 | 12/1998 |
| WO | WO00/17202 | A1 | 3/2000 |
| WO | WO00/42042 | A2 | 7/2000 |
| WO | WO01/02369 | A2 | 1/2001 |
| WO | WO01/16114 | A2 | 3/2001 |
| WO | WO01/19829 | A2 | 3/2001 |
| WO | WO01/25238 | A2 | 4/2001 |
| WO | WO01/31063 | A1 | 5/2001 |
| WO | WO01/38584 | A2 | 5/2001 |
| WO | WO01/16114 | A3 | 8/2001 |
| WO | WO01/55140 | A1 | 8/2001 |
| WO | WO01/56988 | A1 | 8/2001 |
| WO | WO01/19829 | A3 | 9/2001 |
| WO | WO01/25238 | A3 | 10/2001 |
| WO | WO01/38584 | A3 | 10/2001 |
| WO | WO01/81346 | A2 | 11/2001 |
| WO | WO02/06192 | A1 | 1/2002 |
| WO | WO01/81346 | A3 | 3/2002 |
| WO | WO01/02369 | A3 | 4/2002 |
| WO | WO02/30944 | A2 | 4/2002 |
| WO | WO02/057425 | A2 | 7/2002 |
| WO | WO02/076986 | A1 | 10/2002 |
| WO | WO02/080926 | A1 | 10/2002 |
| WO | WO02/083143 | A1 | 10/2002 |
| WO | WO02/088025 | A1 | 11/2002 |
| WO | WO02/090334 | A1 | 11/2002 |

(56) References Cited

FOREIGN PATENT DOCUMENTS

| | | |
|---|---|---|
| WO | WO02/30944 A3 | 1/2003 |
| WO | WO03/000187 A2 | 1/2003 |
| WO | WO03/016275 A1 | 2/2003 |
| WO | WO03/020880 A2 | 3/2003 |
| WO | WO03/024969 A1 | 3/2003 |
| WO | WO03/035075 A1 | 5/2003 |
| WO | WO03/059884 A1 | 7/2003 |
| WO | WO03/020880 A3 | 10/2003 |
| WO | WO03/082341 A1 | 10/2003 |
| WO | WO03/106426 A1 | 12/2003 |
| WO | WO2004/006906 A2 | 1/2004 |
| WO | WO2004/006906 A3 | 3/2004 |
| WO | WO2004/018058 A2 | 3/2004 |
| WO | WO2004/031177 A1 | 4/2004 |
| WO | WO2004/039774 A2 | 5/2004 |
| WO | WO2004/018058 A3 | 7/2004 |
| WO | WO2004/039774 A3 | 7/2004 |
| WO | WO03/000187 A3 | 8/2004 |
| WO | WO2004/087053 A2 | 10/2004 |
| WO | WO2004/111014 A1 | 12/2004 |
| WO | WO2005/002585 A1 | 1/2005 |
| WO | WO2005/007085 A | 1/2005 |
| WO | WO2005/012323 A2 | 2/2005 |
| WO | WO2005/016348 A1 | 2/2005 |
| WO | WO2005/016349 A1 | 2/2005 |
| WO | WO2005/016528 A2 | 2/2005 |
| WO | WO2005/021533 A1 | 3/2005 |
| WO | WO02/057425 A3 | 4/2005 |
| WO | WO2005/012323 A3 | 5/2005 |
| WO | WO2005/016528 A3 | 5/2005 |
| WO | WO2005/044181 A2 | 5/2005 |
| WO | WO2005/047289 A1 | 5/2005 |
| WO | WO2005/061460 A1 | 7/2005 |
| WO | WO2005/063258 A1 | 7/2005 |
| WO | WO2005/067901 A2 | 7/2005 |
| WO | WO2005/074603 A2 | 8/2005 |
| WO | WO2005/007085 A3 | 9/2005 |
| WO | WO2005/097800 A1 | 10/2005 |
| WO | WO2005/105760 A1 | 11/2005 |
| WO | WO2005/067901 A3 | 12/2005 |
| WO | WO2005/112935 A1 | 12/2005 |
| WO | WO2005/113556 A1 | 12/2005 |
| WO | WO2005/117889 A1 | 12/2005 |
| WO | WO2005/120511 A1 | 12/2005 |
| WO | WO2005/044181 A3 | 3/2006 |
| WO | WO2006/030032 A1 | 3/2006 |
| WO | WO2006/038865 A1 | 4/2006 |
| WO | WO2006/050501 A2 | 5/2006 |
| WO | WO2006/050946 A1 | 5/2006 |
| WO | WO2006/068760 A2 | 6/2006 |
| WO | WO2004/087053 A3 | 8/2006 |
| WO | WO2006/089106 A2 | 8/2006 |
| WO | WO2006/108107 A1 | 10/2006 |
| WO | WO2006/112666 A1 | 10/2006 |
| WO | WO2005/074603 A3 | 11/2006 |
| WO | WO2006/114064 A2 | 11/2006 |
| WO | WO2006/114065 | 11/2006 |
| WO | WO2006/114180 A1 | 11/2006 |
| WO | WO2006/068760 A3 | 12/2006 |
| WO | WO2006/089106 A3 | 12/2006 |
| WO | WO2007/002293 A2 | 1/2007 |
| WO | WO2007/006547 A1 | 1/2007 |
| WO | WO2007/020046 A1 | 2/2007 |
| WO | WO2007/002293 A3 | 3/2007 |
| WO | WO2007/025090 A2 | 3/2007 |
| WO | WO2006/050501 A3 | 5/2007 |
| WO | WO2007/061737 A2 | 5/2007 |
| WO | WO2006/114064 A3 | 6/2007 |
| WO | WO2006/114065 A3 | 6/2007 |
| WO | WO2007/025090 A3 | 6/2007 |
| WO | WO2007/075554 A2 | 7/2007 |
| WO | WO2007/079164 A2 | 7/2007 |
| WO | WO2007/095223 A2 | 8/2007 |
| WO | WO2007/075554 A3 | 9/2007 |
| WO | WO2007/079164 A3 | 9/2007 |
| WO | WO2007/103308 A2 | 9/2007 |
| WO | WO2007/106503 A2 | 9/2007 |
| WO | WO2007/112005 A2 | 10/2007 |
| WO | WO2007/114926 A2 | 10/2007 |
| WO | WO2007/121453 A2 | 10/2007 |
| WO | WO2007/121920 A2 | 11/2007 |
| WO | WO2007/121924 A2 | 11/2007 |
| WO | WO2007/124854 A1 | 11/2007 |
| WO | WO2007/125310 A2 | 11/2007 |
| WO | WO2007/125315 A2 | 11/2007 |
| WO | WO2007/126841 A2 | 11/2007 |
| WO | WO2007/134828 A1 | 11/2007 |
| WO | WO2007/135380 A2 | 11/2007 |
| WO | WO2007/135398 A1 | 11/2007 |
| WO | WO2007/061737 A3 | 12/2007 |
| WO | WO2007/125315 A3 | 12/2007 |
| WO | WO2007/121920 A3 | 1/2008 |
| WO | WO2007/103308 A3 | 2/2008 |
| WO | WO2007/112005 A3 | 2/2008 |
| WO | WO2007/125310 A3 | 3/2008 |
| WO | WO2008/025755 A1 | 3/2008 |
| WO | WO2008/037477 A1 | 4/2008 |
| WO | WO2008/047821 A1 | 4/2008 |
| WO | WO2008/063625 A2 | 5/2008 |
| WO | WO2008/064018 A1 | 5/2008 |
| WO | WO2007/121453 A3 | 7/2008 |
| WO | WO2007/135380 A3 | 7/2008 |
| WO | WO2008/063625 A3 | 7/2008 |
| WO | WO2008/079028 A1 | 7/2008 |
| WO | WO2008/082487 A2 | 7/2008 |
| WO | WO2008/094737 A2 | 8/2008 |
| WO | WO2007/121924 A3 | 9/2008 |
| WO | WO2008/112715 A2 | 9/2008 |
| WO | WO2007/114926 A3 | 10/2008 |
| WO | WO2008/118454 A2 | 10/2008 |
| WO | WO2008/118455 A1 | 10/2008 |
| WO | WO2008/118468 A1 | 10/2008 |
| WO | WO2008/125014 A1 | 10/2008 |
| WO | WO2008/125207 A1 | 10/2008 |
| WO | WO2008/127226 A2 | 10/2008 |
| WO | WO2007/126841 A3 | 11/2008 |
| WO | WO2008/112715 A3 | 11/2008 |
| WO | WO2008/118454 A3 | 11/2008 |
| WO | WO2008/136457 A1 | 11/2008 |
| WO | WO2008/082487 A3 | 12/2008 |
| WO | WO2008/127226 A3 | 12/2008 |
| WO | WO2009/000412 A1 | 12/2008 |
| WO | WO2009/004621 A1 | 1/2009 |
| WO | WO2009/010925 A2 | 1/2009 |
| WO | WO2009/023718 A2 | 2/2009 |
| WO | WO2008/094737 A3 | 3/2009 |
| WO | WO2009/023718 A3 | 4/2009 |
| WO | WO2009/044707 A1 | 4/2009 |
| WO | WO2009/050506 A2 | 4/2009 |
| WO | WO2009/062118 A2 | 5/2009 |
| WO | WO2009/064802 A2 | 5/2009 |
| WO | WO2009/010925 A3 | 7/2009 |
| WO | WO2009/064802 A3 | 7/2009 |
| WO | WO2009/088986 A1 | 7/2009 |
| WO | WO2009/088990 A1 | 7/2009 |
| WO | WO2009/100406 A2 | 8/2009 |
| WO | WO2009/117157 A1 | 9/2009 |
| WO | WO2009/050506 A3 | 11/2009 |
| WO | WO2009/100406 A3 | 11/2009 |
| WO | WO2010/009207 A1 | 1/2010 |
| WO | WO2010/019210 A2 | 2/2010 |
| WO | WO2010/036380 A1 | 4/2010 |
| WO | WO2010/039534 A2 | 4/2010 |
| WO | WO2010/045542 A2 | 4/2010 |
| WO | Wo2010/019210 A3 | 5/2010 |
| WO | 2010/039534 A3 | 8/2010 |

OTHER PUBLICATIONS

Abdel-Mohsen, S.A., "Synthesis, reactions and antimicrobial activity of 2-amino-4-(8-quinolinol-5-yl)-1-(p-tolyl)-pyrrole-3-carbonitrile", Bull. Korean Chem. Soc. 2005 26(5):719-728.

Ames et al., "Heterocyclic Synthesis from o-Halogen-acids. Part II. Thienopyridinones and Thienopyranones from 3- bromothiophene

(56) References Cited

OTHER PUBLICATIONS

-2- and 4-Bromothiophene-3-Carboxylic Acids", Journal of the Chemical Society, Perkin Transactions 1, Jan., 14:1390-1395 (1975).
Andrews, R.C., et al. "Effects of the 11β-Hydroxysteroid Dehydrogenase Inhibitor Carbenoxolone on Insulin Sensitivity in Men with Type 2 Diabetes", *J. Clin. Endocrinol. Metab.* (2003) 88(1):285-291.
Apsel, Beth et al., "Targeted polypharmacology: discovery of dual inhibitors of tyrosine and phosphoinositide kinases", *Nature Chemical Biology* 4(11):691-699, 2008.
Aragón, Anthony D. et al., "Characterization of Differentiated Quiescent and Nonquiescent Cells in Yeast Stationary-Phase Cultures", *Molecular Biology of the Cell* 19:1271-1280, 2008.
Aragón, Anthony D. et al., "Microarray based analysis of temperature and oxidative stress induced messenger RNA in *Schistosoma mansoni*", *Molecular & Biochemical Parasitology* 162:134-141, 2008.
Aragón, Tomas et al., "Messenger RNA targeting to endoplasmic reticulum stress signaling sites", *Nature* 457(7230):736-740, 2009.
Arnold, et al. "Pyrrolo[2,3-*d*]pyrimidines containing an extended 5-substituent as potent and selective inhibitors of Ick I", *Bioorg. & Med. Chem. Lett* (2000) 10:2167-70.
Banker, G.S., et al. *Modern Pharmaceutics*, 3ed, Marcel Dekker, New York, 1996, pp. 451-596.
Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", *J. Med. Chem.* (2002) 45(18):3813-3815.
Barnes, P.J., et al. "Efficacy and Safety of Inhaled Corticosteroids in Asthma", *Am. Rev. Respir. Dis.* (1993) 148:S1-26.
Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011, 10 pages.
Beeram, M. et al., "Akt-induced endocrine therapy resistance is reversed by inhibition of mTOR signaling", Annals of Oncology 18:1323-1328, 2007.
Bell, G., et al. "Glucokinase Mutations Insulin Secretion, and Diabetes Mellitus", *Annu. Rev. Physiol.*, (1996) 58:171-186.
Berge, Stephen M. et al., "Pharmaceutical Salts", Journal of Pharmaceutical Sciences Berge et al., "Pharmaceutical Salts", *Journal of Pharmaceutical Sciences* 66(1):1-19, 1977.
Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.
Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.
Bishop, Anthony C. et al., "Design of allele-specific inhibitors to probe protein kinase signalling", Current Biology 8:257-266, 1998.
Blethrow, Justin et al., "Design and Use of Analog-Sensitive Protein Kinases", *Current Protocols in Molecular Biology* 18.11.1-18.11.19, 2004.
Bohren, K.M., et al. "Expression, Crystallization and Preliminary Crystallographic Analysis of Human Carbonyl Reductase", *J. Mol. Biol.* (1994) 224:659-664.
Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.
Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.
Carrasco, Daniel R. et al., "The Differentiation and Stress Response Factor XBP-1 Drives Multiple Myeloma Pathogenesis", *Cancer Cell* 11:349-360, 2007.

Chaisuparat, et al. Dual Inhibition of PI3K(alpha) and mTOR as an Alternative Treatment for Kaposi's Sarcoma. Cancer Research. 2008;68:8361.
Chappelow, et al. Neovascular Age-Related Macular Degeneration: Potential Therapies. Drugs. 2008;68(8):1029-1036.
Cox, B., et al. "Human Colorectal Cancer Cells Efficiently Conjugate the Cyclopentenone Prostaglandin, Prostaglandin $J_2$ to Glutathione", *Biochim. Biophys. Acta* (2002) 1584:37-45.
Cox, Jeffery S. et al., "A Novel Mechanism for Regulating Activity of a Transcription Factor That Controls the Unfolded Protein Response", *Cell* 87:391-404, 1996.
Credle, Joel J. et al., "On the mechanism of sensing unfolded protein in the endoplasmic reticulum", *Proceedings of the National Academy of Sciences* 102(52):18773-18784, 2005.
Dar, Arvin C. et al., "Small Molecule Recognition of c-Src via the Imatinib-Binding Conformation", *Chemistry & Biology* 15:1015-1022, 2008.
Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.
Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", *Eur. J. Endocrinol.* (2000) 142:200-207.
Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.
Ding, S., et al. "A Combinatorial Scaffold Approach Toward Kinase-Directed Heterocycle Libraries", *J. Am. Chem. Soc.* (2002) 124(8):1594-1596.
Ding, S., et al. "A Concise and Traceless Linker Strategy Toward Combinatorial Libraries of 2,6,9-Substituted Purines", *J. Org. Chem.* (2001) 66:8273-8276.
Ding, S., et al. "Resin-Capture and Release Strategy Toward Combinatorial Libraries of 2,6,9-Substituted Purines", *J. Comb. Chem.*(2002) 4:183-186.
Donati. Emerging Therapies for Neovascular Age-Related Macular Degeneration: State of the Art. Ophthalmologica. 2007;221:366-377.
Doody, Gina M. et al., "BLIMP-1 is a target of cellular stress and downstream of the unfolded protein response", *European Journal of Immunology* 36:1572-1582, 2006.
European Examination Report dated Sep. 14, 2011 for EP Application No. 07873406.8, 4 pages.
European search report and search opinion dated Oct. 26, 2011 for Application No. 9700424.6, 5 pages.
European Search Report dated Mar. 1, 2010 for EP Application No. 07873406.8, 5 pages.
European Search Report Dated Feb. 4, 2011 for EP Application No. 05857011.0, 5 pages.
Examination Report for GB Application No. GB0819947.3 dated Oct. 27, 2010, 2 pages.
Extended European Search Report from corresponding European Application No. 09700784.3 dated Oct. 28, 2011, 6 pages.
Extended European Search Report from corresponding European Application No. 12175020.2 dated Jan. 1, 2013, 7 pages.
Extended European Search Report from corresponding European Application No. 12175019.4 dated Apr. 4, 2013, 12 pages.
Fajans, S., et al."Maturity Onset Diabetes of the Young (MODY)", *Diabet. Med.* (1996) 13:S90-S95.
Feinstein, M.B., et al. "Regulation of the Action of Hydrocotisone in Airway Epithelial Cells by 11β-Hydroxysteroid Dehydrogenase", *Am. J. Respir. Cell. Mol. Biol.* (1999) 21:403-408.
Feldman, M.E. et al. , "Active site inhibitors of mTOR target rapamycin-resistant outputs of mTORC1 and mTORC2", PLOS Biology 7(2):371-383, Feb. 2009.
Fingl, E., et al. "General Principles", *The Pharmacological Basis of Therapeutics, Fifth Edition* (1975), Ch. 1, 1-46.
Forrest, G.L., et al. "Carbonyl Reductase", *Chem. Biol. Interact.* (2000) 129:21-40.

(56) References Cited

OTHER PUBLICATIONS

Forrest, G.L., et al. "Induction of a Human Carbonyl Reductase Gene Located on Chromosome 21", *Biochim. Biophys. Acta.* (1990) 1048:149-155.

Franzen, R. "The Suzuki, the Heck, and the Stille reaction—three versative methods for the introduction of new C—C bonds on solid support", *Can J. Chem.* (2000) 78:957-962.

Funder, J.W., et al. "Mineralocorticoid Action: Target Tissue Specificity Is Enzyme, Not Receptor, Mediated", *Science* (1998) 242:583-585.

Garber, M.E., et al. "Diversity of Gene Expression in Adenocarcinoma of the Lung", *Proc. Nat. Acad. Sci. USA* (2001) 98(24):13784-13789.

Gonzalez, B., et al. "Protection against Daunorubicin Cytotoxicity by Expression of a Cloned Human Carbonyl Reductase cDNA in K562 Leukemia Cells", *Cancer Res.* (1995) 55:4646-4650.

Gonzalez, Tania N. et al., "Ire1p: A Kinase and Site-Specific Endoribonuclease", *Methods in Molecular Biology* 160:25-36, 2001.

Graupera, et al. Angiogenesis selectively requires the p110 isoform of PI3K to control endothelial cell migration. Nature. 2008;453:662-666.

Haase, A.,et al. "Detection of Viral Nucleic Acids by in Situ Hybridization", *Methods in Virology* (1984) VII:189-226.

Hanefeld, U., et al. "One-pot Synthesis of Tetrasubstituted Pyrazoles Proof of Regiochemistry", *J. Chem. Soc. Perkin Trans.* (1996) 1:1545-1552.

Hellwinkel, et al. Heterocyclensynthesen mit MF/Al2O3-Basensystemen: 2-Arylbenzofurane and 2,3-Diarylisochinolin-1(2H)-one. Synthesis. 1995;1995(9):1135-41.

International Preliminary Report on Patentability and Written Opinion dated Apr. 17, 2012 for International Application No. PCT/US2010/053072, 5 pages.

International Preliminary Report on Patentability and Written Opinion dated Apr. 19, 2011 for International Application No. PCT/US2009/060985, 6 pages.

International Preliminary Report on Patentability and Written Opinion dated Jan. 1, 2011 for International Application No. PCT/US2009/049969, 7 pages.

International Preliminary Report on Patentability and Written Opinion dated May 22, 2007 for International Application No. PCT/US2005/042524, 12 pages.

International Preliminary Report on Patentability and Written Opinion dated Nov. 4, 2008 for International Application No. PCT/US2007/008355, 7 pages.

International Preliminary Report on Patentability and Written Opinion dated Oct. 8, 2008 for International Application No. PCT/US2007/008395, 6 pages.

International Preliminary Report on Patentability from International Application No. PCT/US2009/000042 issued Jul. 6, 2010, 9 pages.

International search report and written opinion dated Aug. 22, 2011 for PCT/US2011/037412, 2 pages.

International search report and written opinion dated Nov. 20, 2009 for PCT/US2009/005380, 9 pages.

International search report dated Nov. 2, 2010 for PCT Application No. PCT/US10/02020, 8 pages.

International search report dated Mar. 11, 2009 for PCT Application No. PCT/US2009/00038, 1 page.

International search report dated Mar. 23, 2009 for PCT Application No. PCT/US2009/00042, 2 pages.

International Search Report Dated Apr. 5, 2006 for international Application No. PCT/FR2005/051073, 3 pages.

International Search Report dated Aug. 27, 2008 for International Application No. PCT/US07/08395, 4 pages.

International Search report dated Jul. 4, 2011 for International Application No. PCT/US2010/053072, 5 pages.

International Search Report dated Jun. 28, 2010 for International Application No. PCT/US2009/060985, 5 pages.

International Search Report dated Mar. 15, 2010 for International Application No. PCT/US2009/049969, 4 pages.

International Search Report dated Oct. 2, 2006 for International Application No. PCT/US05/042524, 7 pages.

International Search Report dated Sep. 25, 2008 for International Application No. PCT/US07/08355, 1 page.

International Search Report and Written Opinion dated Jun. 28, 2013 for International Application No. PCT/US2012/053542, 13 pages.

Ishiyama, T., et al. "A Stoichiometric Aromatic C—H Borylation Catalyzed by Iridium(I)/2,2'- Bipyridine Complexes at Room Temperature", *Angew. Chem. Int. Ed.* (2002) 41(16):3056-3058.

Ishiyama, T., et al. "Mild Iridium-Catalyzed Borylation of Arenes. High Turnover Numbers, Room Temperature Reactions, and Isolation of a Potential Intermediate", *J. Am. Chem. Soc.* (2002) 124(3):390-391.

Kajita, et al. Nickel-catalyzed decarbonylative addition of phthalimides to alkynes. J Am Chem Soc. May 14, 2008;130(19):6058-9.

Kallberg, Y., et al. "Short-Chain Dehydrogenase/Reductase (SDR) Relationships: a Large Family with Eight Clusters Common to Human, Animal, and Plant Genomes", *Protein Sci.* (2002) 11:636-641.

Kallberg, Y., et al. "Short-Chain Dehydrogenases/Reductases (SDRs)", *Eur. J. Biochem.* (2002) 269:4409-4417.

Kim, M. et al., "Activation and function of the mTORC1 pathway in mast cells", The Journal of Immunology 180:4586-4595, Apr. 2008.

Kimata, Yukio et al., "Two regulatory steps of ER-stress sensor Ire 1 involving its cluster formation and interaction with unfolded proteins", *The Journal of Cell Biology* 179(1):75-86, 2007.

Knight, et al. "A Pharmacological Map of the P13-K Family Defines a Role for p110α in Insulin Signaling", *Cell* (2006) 125:733-747.

Koong, Albert C. et al., "Targeting XBP-1 as a Novel Anti-Cancer Strategy", *Cancer Biology & Therapy* 5(7):756-759, 2006.

Kost et al., "Recyclization of 3-Alkyl- and 1,3-Dialkylisoquinolinium Salts to Naphthylamines", Chemistry of Heterocyclic Compounds, Jan., 16(9):965-970 (1981).

Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.

Kreutzberger, A. et al., "5-substituierte 4-aminopyrimidine durch aminomethynlierung von acetonitrilen", Justus Liebigs Annalen der Chemie 4:537-544, 1977 (not provided in English).

Kudo, Takashi et al., "The Unfolded Protein Response Is Involved in the Pathology of Alzheimer's Disease", *New York Academy of Sciences* 977:349-355, 2002.

Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).

Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.

Kwok, B.H., et al. "The Anti-Inflammatory Natural Product Parthenolide from the Medicinal Herb Feverfew Directly Binds to and Inhibits IkB Kinase", *Chem. Biol.* (2001) 8:759-766.

Lee, et al. All roads lead to mTOR: integrating inflammation and tumor angiogenesis.. Cell Cycle. 2007;6(24):3011-3014.

Lee, Kenneth P.K. et al., "Structure of the Dual Enzyme Ire1 Reveals the Basis for the Catalysis and Regulation in Nonconventional RSN Splicing", *Cell* 132:89-100, 2008.

Lin, Jonathan H. et al., "IRE1 Signaling Affects Cell Fate During the Unfolded Protein Response", *Science* 318:944 (2007).

Majumder, et al. mTOR inhibition reverses Akt-dependent prostate intraepithelial neoplasia through regulation of apoptotic and HIF-1-dependent pathways. Nature Medicine. 2004;10:594-601.

May, Yanjun et al., "The role of the unfolded protein response in tumour development: friend or foe?", *Nature Reviews Cancer* 4:966-977, 2004.

Mayer, T.U., et al. "Small Molecule Inhibitor of Mitotic Spindle Bipolarity Identified in a Pheontype-Based Screen", *Science* (1999) 286:971-974.

(56) References Cited

OTHER PUBLICATIONS

Mellinghoff, et al. TORward AKTually useful mouse models. Nature Medicine. 2004;10:579-580.
Miyaura, N., et al., "Palladium-Catalyzed Cross-Coupling Reactions of Organoboron Compounds," Chem. Rev. (1995) 95(7):2457-2483.
Modi, et at. Isoquinolones: Part IV—Synthesis of 3-Methyl, 3-Formyl & Other 3-Substituted N-Arylisoquinolones, Indian J. Chem. 1979; 18B:304-306.
Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.
Naidoo, Nirinjini et al., "Sleep deprivation induces the unfolded protein response in mouse cerebral cortex", Journal of Neurochemistry 92:1150-1157, 2005.
Nakanishi, M., et al. "Cloning and Sequence Analysis of a cDNA Encoding Tetrameric Carbonyl Reductase of Pig Lung", Biochem. Biophys. Acta (1993) 194(3):1311-1316.
Nemazanyi, et al. 3-Amino-4-aryl-1(2H)-isoquinolones. Chemistry of Heterocyclic Compounds. Mar. 1991;27(3):307-8.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 11β-hydroxysteroid Dehydrogenases with Retained Oxidoreductase Activities", Protein Expr. Purif. (2002) 26:349-356.
Oda, et al. PIK3CA Cooperates with Other Phosphatidylinositol 3'-Kinase Pathway Mutations to Effect Oncogenic Transformation. Cancer Research. 2008;68:8127.
Oppermann, U.C., et al. "Forms and Functions of Human SDR Enzymes", Chem. Biol. Interact. (2001) 130-132(1-3):699-705.
Ozaki, et al. Studies on 4(1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Papa, Feroz R. et al., "Bypassing a Kinase Activity with an ATP-Competitive Drug", Science 302:1533-1537, 2003.
Patel, et al. Immunopathological aspects of age-related macular degeneration. Seminars in Immunopathology. 2008;30(2):97-110.
Persson, C.G. "Glucocorticoids for Asthma—Early Contributions", Pulm. Pharmacol. (1989) 2:163-166.
Petrie et al., "A novel biotinylated adenylate analogue derived from pyrazolo[3,4-d]pyrimidine for labeling DNA probes," Bioconj. Chem. vol. 2, No. 6, (1991), pp. 441-446.
Pudlo, J.S., et al. "Synthesis, Antiproliferative, and Antiviral Activity of Certain 4-Substituted and 4,5 Disubstituted 7[1,3-Dihydroxy-2-propoxy)methyl]pyrrolo[2,3-d]pyrimidines", J. Med. Chem. (1990) 33:1984-1992.
Robertson, R.P. "Eicosandoids and Human Disease", Harrison's Principles of Internal Medicine, Isselbacher K.J., et al. (eds.), McGraw-Hill, New York City (1994) 1:431-435.
Romero, D.G., et al. "Cloning and Expression of the Bovine 11β-hydroxysteroid Dehydrogenase Type-2", J. Steroid Biochm. Mol. Biol. (2000) 72:231-237.
Shamu, Caroline E. et al., "Oligomerization and phosphorylation of the Ire1p kinase during intracellular signaling from the endoplasmic reticulum to the nucleus", The EMBO Journal 15(12):3028-3039, 1996.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. Pharmacol. (1996) 51:117-123.

Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Supplementary European Search Report dated Feb. 24, 2010 for EP Application No. 07754845, 4 pages.
Takeuchi, H. et al. , "Synergistic augmentation of reapamycin-induced autophagy in malignant glioma cells by phosphatidylinositol 3-kinase/protein kinase B inhibitors", Cancer Research 65(8):3336-3346, Apr. 15, 2005.
Tanaka, M., et al. "An Unbiased Cell Morphology-Based Screen for New, Biologically Active Small Molecules", PLoS Biology (2005) 3(5):0764-0776.
Tseng, Ping-Hui et al., "Synergistic interactions between imatinib mesylate and the novel phosphoinositide-dependent kinase-1 inhibitor OSU-03012 in overcoming imatinib mesylate resistance", Blood 105:4021-4027, 2005.
Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457-4459 (2005).
Walker et al., "Structural Determinants of Phosphoinositide 3-Kinase Inhibition by Wortmannin, LY294002, Quercetin, Myricetin, and Staurosporine", Molecular Cell 2000, 6(4):909-919.
White, P.C., et al. "11β-Hydroxysteroid Dehydrogenase and the Syndrome of Apparent Mineralocorticoid Excess", Endocr. Rev. (1997) 18(1):135-156.
Widler, L., et al. "7-Alkyl- and 7-Cycloalkyl-5-aryl-pyrrolo[2,3-d]pyrimidines—Potent Inhibitors of the Tyrosine Kinase c-Src," Bioorganic & Medicinal Chemistry Letters (2001) 11(6):849-852.
Wolff, M. E. Burger's Medicinal Chemistry, 5ed, Part 1, John Wiley & Sons, 1995, pp. 975-977.
Wymann, et al., "Wortmannin Inactivates Phosphoinositide 3-Kinase by Covalent Modification of Lys-802, a Residue Involved in the Phosphate Transfer Reaction", Molecular and Cellular Biology 1996, 16(4):1722-1733.
Yaguchi, et al., "A novel phosphatidylinositol 3-kinase inhibitor, ZSTK474 exterted antitumor activity against human tumor xenografts by oral administration", Proc. Amer. Assoc. Cancer Res. 2005, 46:1691 (Abstract).
Yaguchi, et al. Antitumor activity of ZSTK474, a new phosphatidylinositol 3-kinase inhibitor. J. Natl. Cancer. Inst. 2006; 98(8): 545-556. Abstract only.
Yoshida, Hiderou et al., "XBP1 mRNA Is Induced by ATF6 and Spliced by IRE1 in Response to ER Stress to Produce a Highly Active Transcription Factor", Cell 107:881-891, 2001.
Zhang, Xuewu et al., "An Allosteric Mechanism for Activation of the Kinase Domain of Epidermal Growth Factor Receptor", Cell 125:1137-1149, 2006.
Zheng, Yi et al., "Hepatitis C Virus Non-structural Protein NS4B Can Modulate an Unfolded Protein Response", The Journal of Microbiology 43(6):529-536, 2005.
West et al., "Activation of the PI3K/Akt pathway and chemotherapeutic resistance," Drug Resistance Updates, 5, 2002, 234-248.
International Preliminary Report on Patentability and Written Opinion dated Mar. 4, 2014 for International Application No. PCT/US2012/053542, 10 pages.

* cited by examiner

US 8,980,899 B2

METHODS OF INHIBITING IRE1

CROSS-REFERENCES TO RELATED APPLICATIONS

This application is a National Stage Entry of PCT/US2010/053072, filed Oct. 18, 2010 which claims the benefit of U.S. Provisional Patent Application No. 61/252,230, filed Oct. 16, 2009, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support by grant contract Nos. W81XWH-06-1-0727 and W81XWH-06-1-0383 by the Department of Defense. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 84850-011910US-837239_ST25.TXT, created on Apr. 16, 2012, 609 bytes, machine format IBM-PC, MS-Windows operating system, is hereby incorporated by reference in its entirety for all purposes.

BACKGROUND OF THE INVENTION

Approximately one-third of all the proteins in eukaryotes enter the ER for post-translational processing and folding. The quality of protein folding is monitored by the ER membrane-resident kinase-ribonuclease Ire1, which is activated by misfolded proteins. Ire1 initiates a non-spliceosomal cytoplasmic splicing reaction of transcription factor encoding mRNA initiating a genome-scale transcriptional program termed unfolded protein response (UPR). Translation of the spliced mRNA yields a UPR-specific transcription factor, termed Hac1 (Cox, J. S. et al., *Cell* 87:391-404 (1996)) in yeasts and Xbp1 (Yoshida, H. et al., *Cell* 107:881-91 (2001)) in metazoans, that activates genes involved in protein biogenesis and restores protein folding in the ER. The UPR activates in cancers (Koong, A. C. et al., *Cancer Biol Ther* 5 (2006); Ma, Y. et al., *Nat Rev Cancer* 4:966-77 (2004)), in Alzheimer's disease (Kudo, T. et al. *Ann N Y Acad Sci* 977:349-55 (2002)), and in a variety of other cellular anomalies (Zheng, Y. et al. *J Microbiol* 43:529-36 (2005); Naidoo, N. et al., *J Neurochem* 92:1150-7 (2005); Doody, G. M. et al., *Eur J Immunol* 36:1572-82 (2006)), suggesting numerous possible links between abnormal Ire1 activation and cellular dysfunctions.

During the UPR, the ER-lumenal domain (LD) acts as a sensor of unfolded proteins and promotes lateral self-association of Ire1 in the plane of the ER membrane (FIG. 1A). Notably, the purified LD crystallizes as an oligomer that has two distinct crystallographic interfaces. Ire1 surface residues on both interfaces contribute to Ire1 activation in vivo (Credle, J. J. et al., *Proc Natl Acad Sci USA* 102:18773-84 (2005)). This finding explains an early observation of oligomerization of Ire1 during the UPR (Shamu, C. E. et al., *Embo J* 15:3028-39 (1996)) and provides a first structural rationalization of Ire1 organization in UPR-induced foci that can be observed by life-cell imaging (Kimata, Y. et al. *J Cell Biol* 179:75-86 (2007)) (Aragon et al., 2008). It has been proposed that oligomerization of the LD would increase the local concentration of the kinase-RNase domains of Ire1 on the cytosolic side of the ER membrane and activate the enzymatic domains by dimerization (Credle, J. J. et al., *Proc Natl Acad Sci USA* 102:18773-84 (2005)). This mechanism of activation parallels that for many well-understood cell surface signaling receptors. Ligand-induced dimerization of epithelial growth factor receptors (EGFR) (Zhang, X. et al., *Cell* 125: 1137-49 (2006)), for example, activates the kinase domains by inducing conformational changes that include opening of the N- and the C-lobes of the kinase and rearrangement of the activation loop and the highly conserved αC helix (Zhang, X. et al., *Cell* 125:1137-49 (2006)). In addition to self-association, activation of Ire1 involves autophosphorylation and binding of ADP as a co-factor. Both of these events are thought to facilitate a conformational change that activates the RNase (Papa, F. R. et al., *Science* 302:1533-7 (2003); Gonzalez, T. N. et al., *Methods Mol Biol* 160:25-36 (2001)).

A crystal structure of the Ire1 kinase-RNase domain has been reported (Lee, K. P. et al., *Cell* 132:89-100 (2008)). The structure revealed a two-fold symmetric dimer with a back-to-back arrangement of the kinase domains, compactly attached to an RNase dimer with two independent active sites. The structure is well ordered except for the activation loop, the loop following the αD helix of the kinase domain, and a functionally important and apparently highly dynamic loop of the RNase domain. The back-to-back arrangement of the kinases in the dimer is unexpected because it positions the phosphorylation sites in the activation loops 43-48 Å away from the active site of the partnering molecule in the dimer. This arrangement does not appear productive for the trans-autophosphorylation of Ire1 observed in vivo (Shamu, C. E. et al., *Embo J* 15:3028-39 (1996)) and in vitro (Lee, K. P. et al., *Cell* 132:89-100 (2008)). The dimerization of the RNase domains has been proposed to allow recognition of the conserved tandem stem-loops comprising the splice sites in HAC1/XBP1 mRNA (Lee, K. P. et al., *Cell* 132:89-100 (2008)) (FIG. 1B).

The association of ER stress with diverse human diseases, such as cancer, diabetes, proteinopathies, and viral infections, provides reasoning to alter pathogenesis by manipulating the UPR. See, e.g., Carrasco D R, et al. The differentiation and stress response factor XBP-1 drives multiple myeloma pathogenesis. *Cancer Cell* 11(4):349-60 (2007). Cancers such as multiple myeloma undergo rapid proliferation. Artificially elevated activity of XBP-1, which is immediately downstream of Ire1, causes multiple myeloma. These data establish a direct and causal link between Ire1 activity and cancer.

Inhibitors of Ire1 RNase activity have long been elusive. The present invention provides solutions to these and other problems in the art.

BRIEF SUMMARY OF THE INVENTION

Provided herein are methods and compositions for inhibiting Ire1 enzymatic activity and, in some embodiments, preventing UPR-induced cell death.

In one aspect, a method of decreasing Ire1 activity is provided. The method includes contacting Ire1 with an effective amount of a compound having the formula:

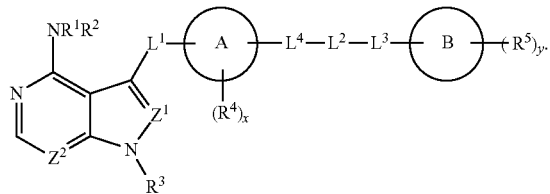

In Formula I, $Z^1$ and $Z^2$ are independently —N= or substituted or unsubstituted —C($R^{31}$)=. $R^{31}$ is hydrogen, halogen, —CN, —CF$_3$, —OH, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ and $R^2$ are independently hydrogen, substituted or unsubstituted alkyl, or substituted or unsubstituted heteroalkyl. Ring A is substituted or unsubstituted arylenyl, substituted or unsubstituted heteroarylenyl, substituted or unsubstituted cycloalkylenyl, or substituted or unsubstituted heterocycloalkylenyl. Ring B is substituted or unsubstituted aryl, substituted or unsubstituted heteroaryl, substituted or unsubstituted cycloalkyl, or substituted or unsubstituted heterocycloalkyl. $R^3$, $R^4$, and $R^5$ are independently halogen, —CN, —CF$_3$, —S(O)$_n$R$^6$, —N(O)$_m$, —NR$^7$R$^8$, —C(O)OR$^9$, —N=NR$^7$, —NR$^{10}$—C(O)R$^{11}$, —NR$^{12}$—C(O)—OR$^{13}$, —C(O)NR$^{14}$R$^{15}$, —NR$^{16}$S(O)$_n$R$^{17}$, —S(O)$_n$NR$^{18}$R$^{18'}$, —OR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n and m are independently an integer from 0 to 2. The symbol x represents an integer from 0 to 4; y is an integer from 0 to 5. $L^1$ is a bond, substituted or unsubstituted alkylene, or substituted or unsubstituted heteroalkylene. $L^2$ is a bond, —S(O)—, —S(O)$_2$—, or —C(O)—. $L^3$ is a bond, —N(R$^{20}$)—, substituted or unsubstituted alkylene, or substituted or unsubstituted heteroalkylene. $L^4$ is a bond, —NR$^{20'}$—, or —CHR$^{20'}$—. $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{20}$ and $R^{20'}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, a method is provided for treating a disorder responsive to inhibition of Ire1. The method includes administering to a subject an effective amount of a compound of Formula I above.

In another aspect, a method of treating a disorder selected from the group consisting of a cancer, an inflammatory disease, or an autoimmune disease is provided. The method includes administering to a subject an effective amount of a compound of Formula I above.

BRIEF DESCRIPTION OF THE DRAWINGS

FIG. 1. Activation of Ire1 by self-association.

FIG. 4. Titrations of Ire1 inhibitors to measure $K_i$ using 1 µM hIre1 (5'-$^{32}$p-HP21, 30° C.).

DETAILED DESCRIPTION OF THE INVENTION

I. Abbreviations and Definitions

Figure 1A:
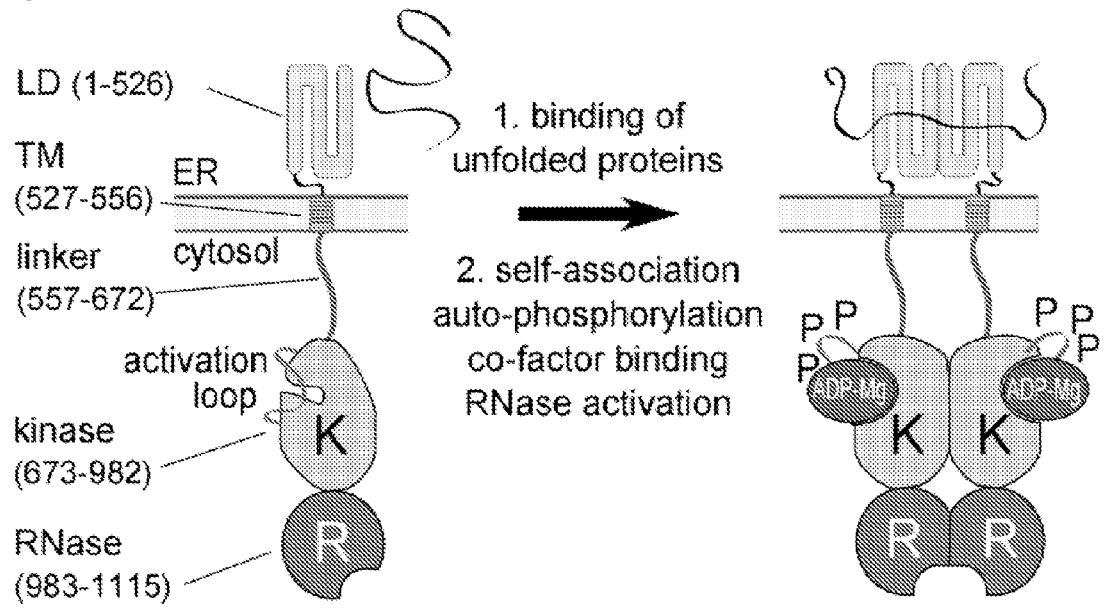
FIG. 1A: Unfolded proteins in the endoplasmic reticulum (ER) bind to the lumenal domain (LD) and activate the kinase (K) and the ribonuclease (R) domains of Ire1.
Figure 1B:
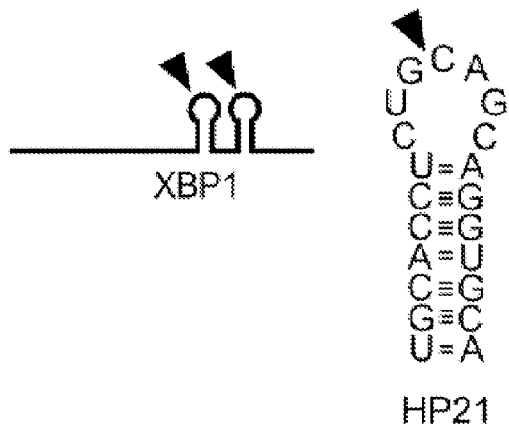
FIG. 1B: Schematic representation of Ire1 substrates used. Sequence of HP21: UGCACCUCUGCAGCAGGUGCA (SEQ ID NO:1).
Figure 1C:
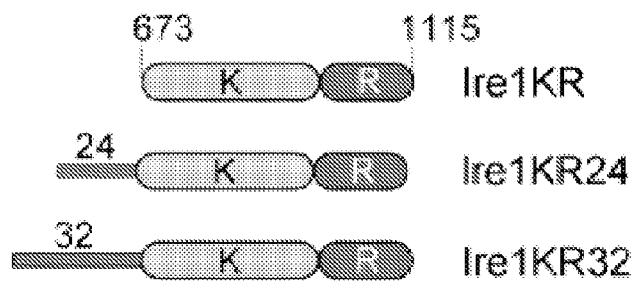
FIG. 1C: Ire1 constructs used for cleavage assays and structure determination.
Figure 1D:
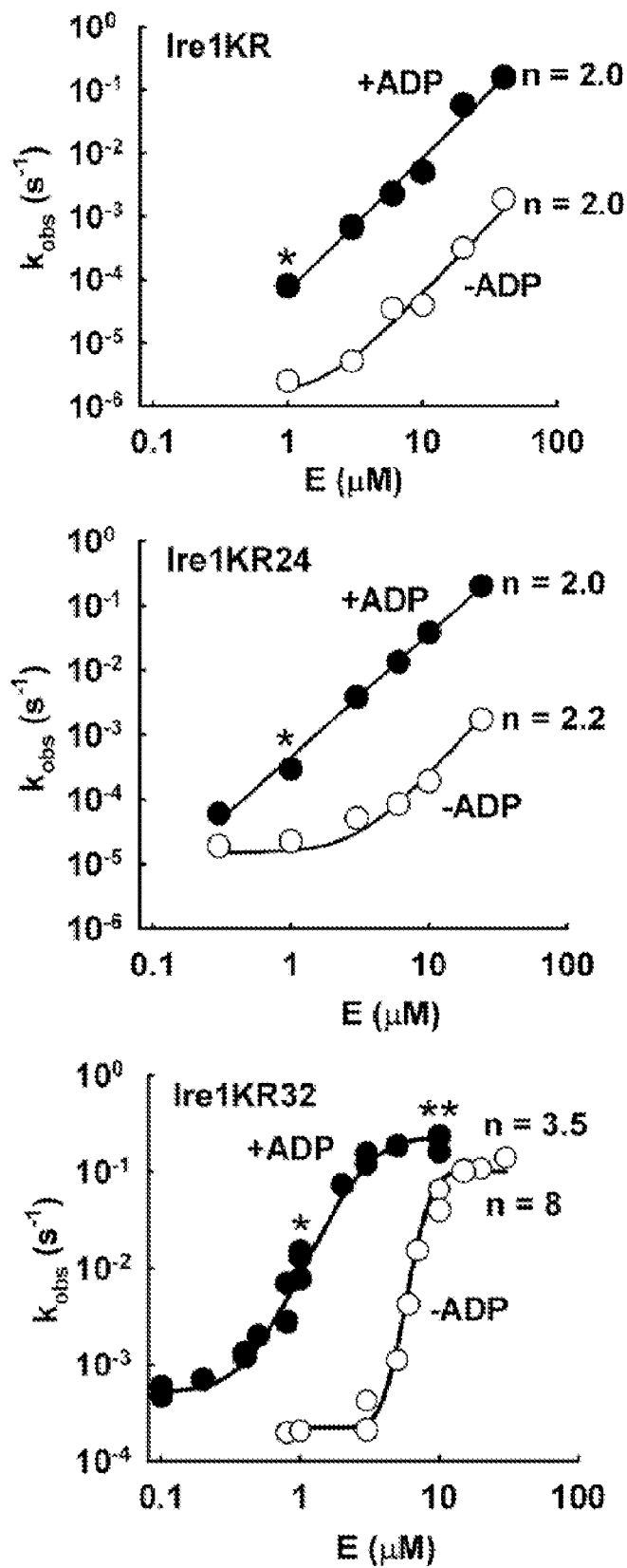
FIG. 1D: Cooperative activation profiles for Ire1KR (top panel), Ire1KR24 (middle panel) and Ire1KR32 (bottom panel) obtained using 5'-$^{32}$p-HP21, with (+ADP) or without (−ADP) co-factor.
Figure 2:
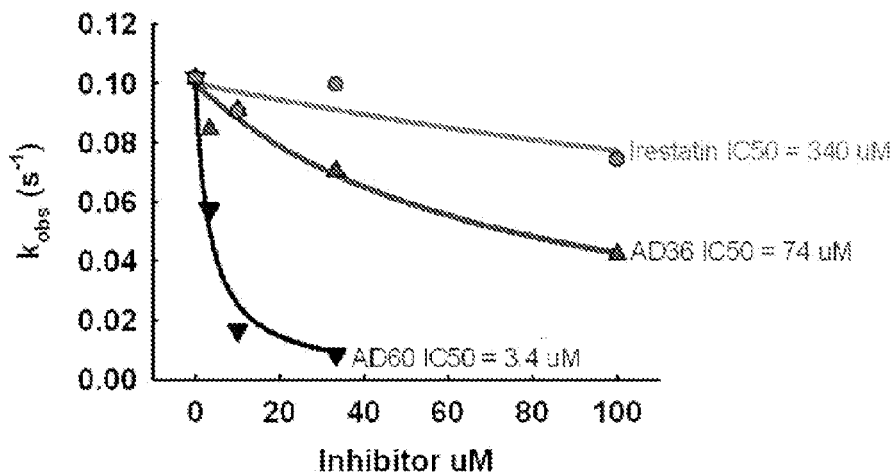
FIG. 2 depicts inhibition of yIre1 at varying concentrations by exemplary compounds AD36 and AD60 versus irestatin.
Figure 3:
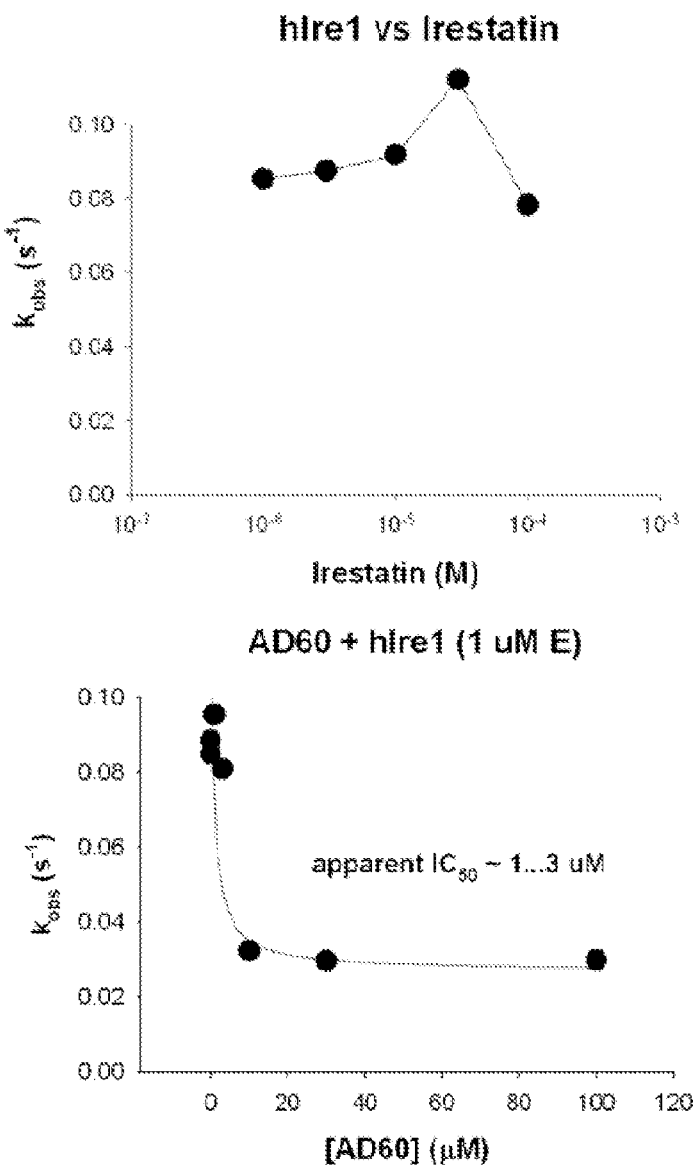
FIG. 3 depicts inhibition of hIre1 by irestatin (top panel), and B exemplary compound AD60 (bottom panel).
Figure 4A:
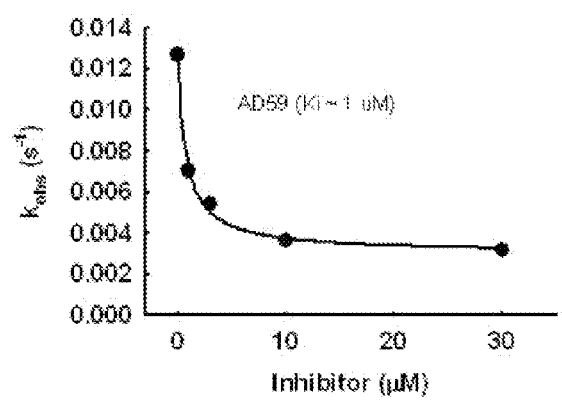
FIG. 4A: Exemplary compound AD59 exhibits $K_i$ of about 1 µM.
Figure 4B:
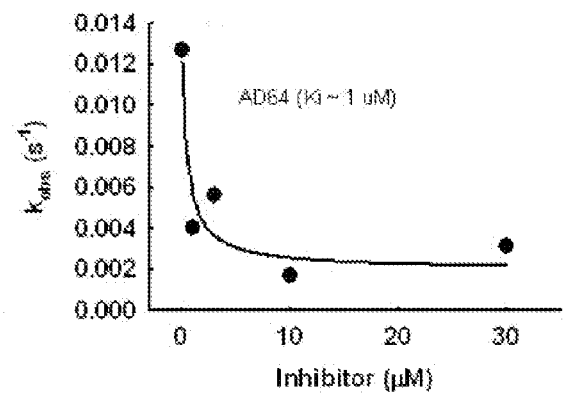
FIG. 4B: Exemplary compound AD64 exhibits $K_i$ of about 1 µM.
Figure 4C:
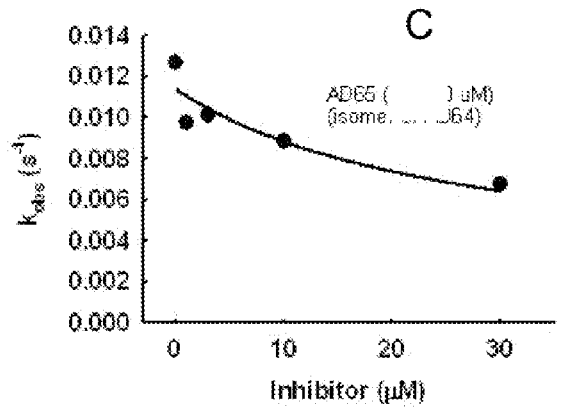
FIG. 4C: Exemplary compound AD65, an isomer of AD64, exhibits $K_i$ of about 30 µM.
Figure 4D:
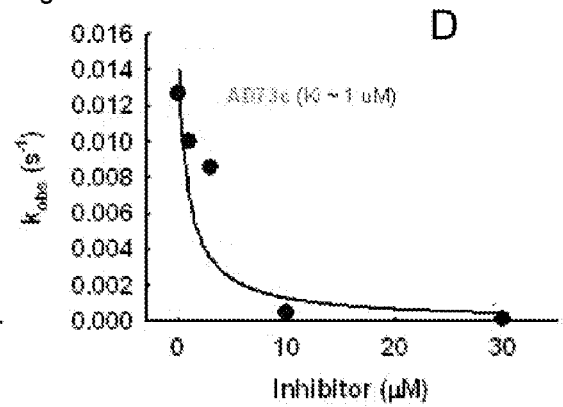
FIG. 4D: Exemplary compound AD73c shows 100-fold rate suppression.

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched carbon chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain one or more heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from an aryl and heteroaryl, respectively. A "fused ring" refers a ring system with two or more rings having at least one bond and two atoms in common. Thus, a "fused ring aryl" and a "fused ring heteroaryl" refer to ring systems having at least one aryl and heteroaryl, respectively, that share at least one bond and two atoms in common with another ring.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S(O$_2$)—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T—C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

"Methods of treating a disease," as used herein, refers to methods of treating a disease state, a condition caused by a disease state, or disease symptoms. The term "treating" and conjugations thereof, include prevention of a disease.

A "peptide" refers to a polymer in which the monomers are amino acids and are joined together through amide bonds, alternatively referred to as a "polypeptide" or "peptide." The terms "protein" encompasses polypeptides, proteins. Unnatural amino acids, for example, β-alanine, phenylglycine and homoarginine are also included under this definition. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983). Thus, an Ire1 protein (also referred to herein as simply "Ire1") includes recombinant Ire1 protein as well as copies of the same Ire1 protein or versions from different sources (e.g. human Ire1, mouse Ire1, yeast Ire1). Where Ire1 proteins are oligomerized, the Ire1 proteins forming the oligomer may be from the same or different sources.

II. Ire1 Inhibitors

Provided herein are Ire1 inhibitors. An "Ire1 inhibitor," as used herein, is a compound that decreases the activity of Ire1, either directly or indirectly, relative to the activity of Ire1 in the absence of the compound. In some embodiments, the Ire1 inhibitors are capable of acting on yeast and/or human Ire1 directly. In one embodiment, the Ire1 inhibitor comprises a pyrazolo-pyrimidinyl moiety (also referred to herein as pyrazol-pyrimidinyl Ire1 inhibitors). In some embodiments, the pyrazolo-pyrimidinyl Ire1 inhibitor has the formula:

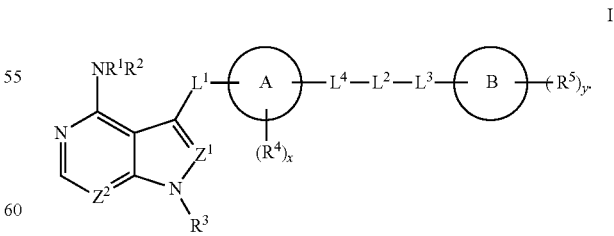

In Formula I, $Z^1$ and $Z^2$ are independently —N= or —C($R^{31}$)=. $R^{31}$ is hydrogen, halogen, —CN, —CF$_3$, —OH, —NH$_2$, —SO$_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiment, $R^{31}$ is hydrogen, halogen, —CN, —CF$_3$, —OH, —NH$_2$, —SO$_2$, —COOH, —CONH$_2$, oxo, unsubstituted alkyl, unsubstituted heteroalkyl, unsubstituted cycloalkyl, unsubstituted heterocycloalkyl, unsubstituted aryl, or unsubstituted heteroaryl. In certain embodiments, $R^{31}$ is hydrogen or $C_{1-10}$ (e.g., $C_{1-4}$) unsubstituted alkyl. $R^{31}$ may also simply be hydrogen.

$R^1$ and $R^2$ are independently hydrogen, substituted or unsubstituted alkyl, or substituted or unsubstituted heteroalkyl. In some embodiments, $R^1$ and $R^2$ are independently hydrogen or $C_{1-10}$ (e.g., $C_{1-4}$) unsubstituted alkyl. In some embodiments, at least one of $R^1$ or $R^2$ is hydrogen. In some embodiments, both $R^1$ and $R^2$ are hydrogen. In other embodiments, $R^1$ and $R^2$ are independently $R^{21}$-substituted or unsubstituted alkyl or $R^{21}$-substituted or unsubstituted heteroalkyl. $R^{21}$ is independently halogen, —CN, —CF$_3$, —OH, —NH$_2$, —SO$_2$, —COOH, —CONH$_2$, oxo, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

Ring A is substituted or unsubstituted arylenyl (i.e. a divalent aryl), substituted or unsubstituted heteroarylenyl (i.e. a divalent heteroaryl), substituted or unsubstituted cycloalkylenyl, or substituted or unsubstituted heterocycloalkylenyl. In some embodiments, ring A is substituted or unsubstituted arylenyl, or substituted or unsubstituted heteroarylenyl. In some embodiments, ring A is substituted or unsubstituted arylenyl. In some embodiments, ring A is substituted or unsubstituted phenylenyl (i.e. a divalent phenyl). In some embodiments, ring A is unsubstituted phenylenyl.

Ring B is substituted or unsubstituted aryl, substituted or unsubstituted heteroaryl, substituted or unsubstituted cycloalkyl, or substituted or unsubstituted heterocycloalkyl. In some embodiments, Ring B is substituted or unsubstituted aryl or substituted or unsubstituted heteroaryl. In some embodiments, ring B is substituted or unsubstituted aryl. In some embodiments, ring B is substituted or unsubstituted phenyl. Where ring A or ring B is "unsubstituted," it is meant that ring A or ring B is not attached to any substituents in addition to those set forth in Formula I (i.e. $R^4$ and $R^5$ respectively). Where ring A or B is substituted, they may be substituted with a $R^{32}$, wherein $R^{32}$ is halogen, —CN, —CF$_3$, —OH, —NH$_2$, —SO$_2$, —COOH, —CONH$_2$, oxo, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

$R^3$, $R^4$, and $R^5$ are independently halogen, —CN, —CF$_3$, —S(O)$_n$R$^6$, —N(O)$_m$ (e.g. NO$_2$), —NR$^7$R$^8$, —C(O)R$^9$, —C(O)OR$^9$, —N=NR$^7$, —NR$^{10}$—C(O)R$^{11}$, —NR$^{12}$—C(O)—OR$^{13}$, —C(O)NR$^{14}$R$^{15}$, —NR$^{16}$S(O)$_n$R$^{17}$ (e.g. —NR$^{16}$S(O)$_2$R$^{17}$), —S(O)$_n$NR$^{18}$R$^{18}$ (e.g. —S(O)$_2$NR$^{18}$R$^{18'}$), —OR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n and m are independently an integer from 0 to 2. In some embodiments, $R^3$, $R^4$, and $R^5$ are independently —CN, —CF$_3$, —S(O)$_n$R$^6$, —NR$^7$R$^8$, —C(O)R$^9$, —C(O)OR$^9$, —N=NR$^7$, —NR$^{10}$—C(O)R$^{11}$, —NR$^{12}$—C(O)—OR$^{13}$, —C(O)NR$^{14}$R$^{15}$, —NR$^{16}$S(O)$_n$ R$^{17}$, —S(O)$_n$NR$^{18}$, —OR$^{19}$, R$^{23}$-substituted or unsubstituted alkyl, R$^{23}$-substituted or unsubstituted heteroalkyl, R$^{23}$-substituted or unsubstituted cycloalkyl, R$^{23}$-substituted or unsubstituted heterocycloalkyl, R$^{23}$-substituted or unsubstituted aryl, or R$^{23}$-substituted or unsubstituted heteroaryl. $R^{23}$ is independently halogen, —CN, —CF$_3$, —OH, oxo, —NH$_2$, —NO$_2$, —SH, —SO$_2$, —COOH, —COOR$^{24}$, —C(O)NHR$^{24}$, R$^{24}$-substituted or unsubstituted alkyl, R$^{24}$-substituted or unsubstituted heteroalkyl, R$^{24}$-substituted or unsubstituted cycloalkyl, R$^{24}$-substituted or unsubstituted heterocycloalkyl, R$^{24}$-substituted or unsubstituted aryl, or R$^{24}$-substituted or unsubstituted heteroaryl.

In some embodiments, $R^3$ is substituted or unsubstituted $C_{1-10}$ alkyl (e.g., $C_{1-6}$ alkyl), substituted or unsubstituted $C_{3-8}$ cycloalkyl (e.g., $C_{3-6}$ cycloalkyl), or substituted or unsubstituted 4-8 membered (e.g., 5-6 membered) heterocycloalkyl. In some embodiments, $R^3$ is unsubstituted $C_{1-4}$ alkyl or unsubstituted $C_{3-6}$ cycloalkyl.

In other embodiments, $R^3$ is $R^{23}$-substituted $C_{1-3}$ alkyl, and $R^{23}$ is —OH, substituted or unsubstituted cycloalkyl, or substituted or unsubstituted aryl (e.g., phenyl). In some embodiments, $R^3$ is isobutyl, propyl substituted with hydroxyl, or methyl substituted with phenyl, methyl, or cyclopentyl. In some embodiments, $R^3$ is cyclopentyl.

In other embodiments, $R^3$ is substituted or unsubstituted 5-6 membered heterocycloalkyl. In some embodiments, $R^3$ is unsubstituted 5-membered heterocycloalkyl, e.g., furanyl or pyrrolyl.

In other embodiments, $R^3$ is $R^{23}$-substituted 5-6 membered heterocycloalkyl, e.g., $R^{23}$-substituted pyrrolyl. In some of these embodiments, $R^{23}$ is —COOR$^{29}$ or —C(O)NHR$^{30}$. $R^{29}$ and $R^{30}$ are independently halogen, —CN, —CF$_3$, —OH, —NH$_2$, —SO$_2$, —COOH, oxo, —CONH$_2$, R$^{31}$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl. In one embodiment, $R^{29}$ and $R^{30}$ are independently R$^{31}$-substituted or unsubstituted alkyl (e.g., $C_1$-$C_4$ alkyl) or R$^{31}$-substituted or unsubstituted aryl.

In one embodiment, $R^3$ is $R^{23}$-substituted pyrrolyl, $R^{23}$ is —C(O)NHR$^{30}$, and $R^{30}$ is R$^{31}$-substituted or unsubstituted aryl, e.g., R$^{31}$-substituted or unsubstituted phenyl. In one embodiment, $R^{31}$ is —CF$_3$.

In another embodiment, $R^3$ is $R^{23}$-substituted pyrrolyl, $R^{23}$ is —COOR$^{29}$, and $R^{29}$ is R$^{31}$-substituted or unsubstituted alkyl (e.g., $C_1$-$C_4$ alkyl), e.g., tert-butyl.

In some embodiments, $R^5$ is $R^{23}$-substituted $C_{1-3}$ alkyl, and $R^{23}$ is a halogen. In one embodiment, $R^5$ is —CF$_3$. In other embodiments, $R^5$ is —CF$_3$, —Br, —Cl, —I, —NO$_2$, —CH$_3$, —C$_2$H$_5$, —SH, —OH, —OMe, —CN, —SMe, —NO, —COOH or —COH.

In Formula I, x is an integer from 0 to 4. In some embodiments, x is 1. In some embodiments, x is 0.

In Formula I, y is an integer from 0 to 5. In some embodiments, y is 0 or 1. In some embodiments, y is 0. In some embodiments, y is 1.

$L^1$ is a bond, substituted or unsubstituted alkylene, or substituted or unsubstituted heteroalkylene. In some embodiments, $L^1$ is a bond or substituted or unsubstituted alkylene. In some embodiments, $L^1$ is a bond or unsubstituted methylene. In some embodiments, $L^1$ is methylene.

$L^2$ is a bond, —S(O)—, —S(O)$_2$—, or —C(O)—. $L^2$ may be —S(O)—, —S(O)$_2$—, or —C(O)—. In some embodiments, $L^2$ is —C(O)—.

$L^3$ is a bond, —N(R$^{20}$)—, substituted or unsubstituted alkylene, or substituted or unsubstituted heteroalkylene. In some embodiments, $L^3$ is a bond. In other embodiments, $L^3$ is —N(R$^{20}$)—, and $R^{20}$ is hydrogen or a substituted or unsubstituted $C_{1-4}$ alkyl. In some embodiments, $L^3$ is —N(H)—.

In some embodiments, $L^4$ is a bond, $-NR^{20'}-$ (e.g. $-NH-$), or $-CHR^{20'}-$ (e.g. $-CH_2-$). In some embodiments, $L^4$ is a bond. In some embodiments, $L^4$ is $-NH-$. In some embodiments, $L^4$ is $-CH_2-$.

In some embodiments, $L^1$ and/or $L^3$ is a bond, $R^{25}$-substituted or unsubstituted alkylene, or $R^{25}$-substituted or unsubstituted heteroalkylene. $R^{25}$ is independently halogen, $-CN$, $-CF_3$, $-OH$, oxo, $-NH_2$, $-NO_2$, $-COOH$, $-CHNH_2$, $-SH$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{20}$ and $R^{20'}$ are independently (and each appearance or occurrence of $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{20}$ and $R^{20'}$ individually are independently (e.g. each appearance or occurrence of $R^6$ is independently)) hydrogen, halogen, $-CN$, $-CF_3$, $-OH$, oxo, $-NH_2$, $-NO_2$, $-COOH$, $-CHNH_2$, $-SH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{20}$ and $R^{20'}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{20}$ and $R^{20'}$ are independently hydrogen, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. $R^{27}$ is independently halogen, $-CN$, $-CF_3$, $-OH$, $-NH_2$, $-SO_2$, $-COOH$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

$R^{22}$, $R^{24}$, $R^{26}$, $R^{28}$, $R^{31}$ and $R^{33}$ are independently halogen, $-CN$, $-CF_3$, $-OH$, oxo, $-NH_2$, $-NO_2$, $-SH$, $-COOH$, $-CONH_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^4$ is $-NH-$, and $Z^1$ and $Z^2$ are both $-N=$ such that the compound has the formula:

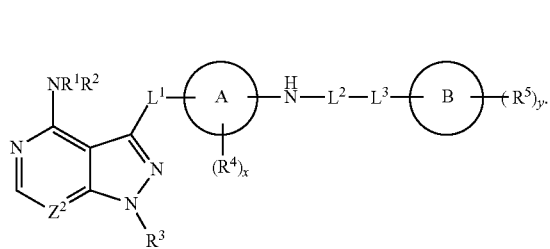

Ia

In some embodiments, Ire1 inhibitor compounds are provided having the formula:

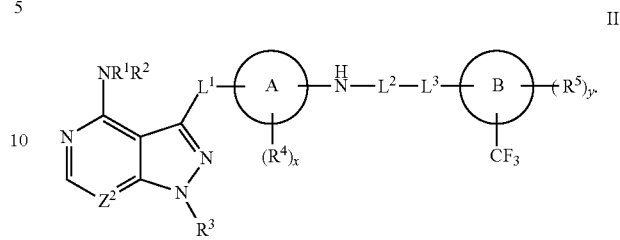

II

In Formula II, x, y, ring A, $R^1$, $R^2$, $R^3$, $L^1$, $L^3$, and $R^5$ are defined as above in the discussion of Formula I. Ring B is unsubstituted aryl or unsubstituted heteroaryl. Where ring B is "unsubstituted," it is meant that ring B is not attached to any substituents beyond those identified in Formula II (i.e., $CF_3$ and $R^5$). In some embodiments, ring B is substituted or unsubstituted aryl. In some embodiments, ring B is substituted or unsubstituted phenyl. In some embodiments, ring B includes only one substituent: the $-CF_3$ group shown in Formula I. In other embodiments, ring B includes one or more additional substituents as designated by $(R^5)_y$.

In some embodiments, Ire1 inhibitor compounds are provided having the formula:

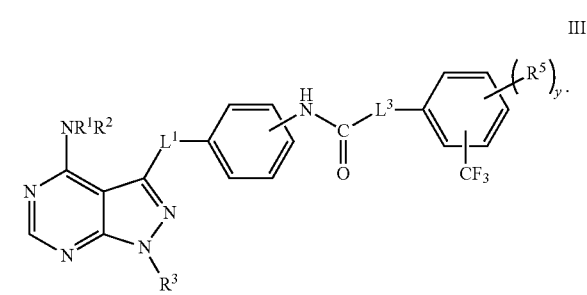

III

In some embodiments, compounds are provided having the formula:

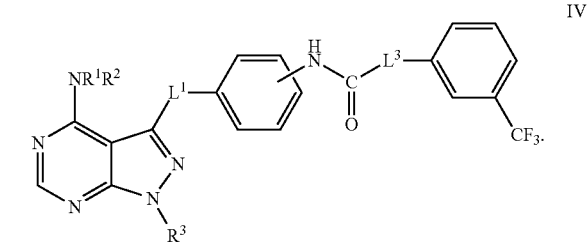

IV

In Formulae III and IV, $R^1$, $R^2$, $R^3$, $L^1$, $L^3$, and $R^5$ are defined as above in the discussion of Formula I.

In another embodiment, compounds are provided having the formula:

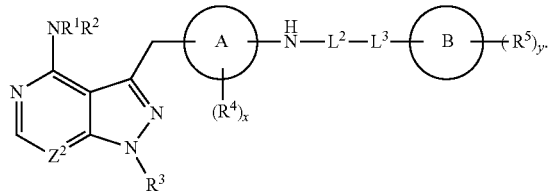

V

In Formula V, x, y, ring A, ring B, $L^2$, $L^3$, $R^1$, $R^2$, $R^3$, $R^4$, and $R^5$ are as defined for Formula I above.

Unless otherwise noted, the symbols in Formulae Ia and II-V are as defined above in the discussion of Formula I.

In another aspect, compounds are provided having the formula:

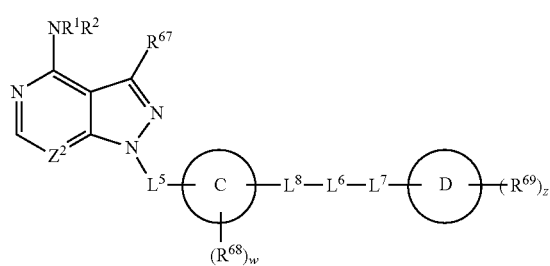

VI wherein $R^1$ and $R^2$ are as defined above.

Ring C is substituted or unsubstituted arylenyl, substituted or unsubstituted heteroarylenyl, substituted or unsubstituted cycloalkylenyl, or substituted or unsubstituted heterocycloalkylenyl. In some embodiments, ring C is heteroarylenyl or heterocycloalkylenyl. In some embodiments, ring C is a nitrogen-containing 5-6 membered heterocycloalkylenyl, e.g., pyrrolidine. Ring D is substituted or unsubstituted aryl, substituted or unsubstituted heteroaryl, substituted or unsubstituted cycloalkyl, or substituted or unsubstituted heterocycloalkyl. In some embodiment, ring D is aryl or heteroaryl. In one embodiment, ring D is aryl, e.g., phenyl. Where ring C or ring D is substituted, they may be substituted with a $R^{32'}$, wherein $R^{32'}$ is halogen, —CN, —CF$_3$, —OH, —NH$_2$, —SO$_2$, —COOH, —CONH$_2$, oxo, $R^{33'}$-substituted or unsubstituted alkyl, $R^{33'}$-substituted or unsubstituted heteroalkyl, $R^{33'}$-substituted or unsubstituted cycloalkyl, $R^{33'}$-substituted or unsubstituted heterocycloalkyl, $R^{33'}$-substituted or unsubstituted aryl, or $R^{33'}$-substituted or unsubstituted heteroaryl. $R^{33'}$ is independently halogen, —CN, —CF$_3$, —OH, oxo, —NH$_2$, —NO$_2$, —SH, —COOH, —CONH$_2$, unsubstituted alkyl, unsubstituted heteroalkyl, unsubstituted cycloalkyl, unsubstituted heterocycloalkyl, unsubstituted aryl, or unsubstituted heteroaryl.

In Formula VI, w is an integer from 0 to 4, and z is an integer from 0 to 5. In some embodiments, w is 0. In some embodiments, z is 0 or 1, In some embodiments, z is 0.

$R^{67}$, $R^{68}$, and $R^{69}$ are independently halogen, —CN, —CF$_3$, —S(O)$_n$R$^6$, —N(O)$_m$ (e.g., —NO$_2$), —NR$^7$R$^8$, —C(O)R$^9$, —C(O)OR$^9$, —N=NR$^7$, —NR$^{o1}$—C(O)R$^{11}$, —NR$^{12}$—C(O)—OR$^{13}$, —C(O)NR$^{14}$R$^{15}$, —NR$^{16}$S(O)$_n$R$^{17}$ (e.g., —NR$^{16}$S(O)$_2$R$^{17}$), —S(O)$_n$NR$^{18}$R$^{18'}$ (e.g., —S(O)$_2$NR$^{18}$R$^{18'}$), —OR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n and m are independently (including each appearance of n and m individually) an integer from 0 to 2. In some embodiments, $R^{67}$ is —NH$_2$.

In some embodiments, $R^{68}$ is halogen, —CN, —CF$_3$, —S(O)$_n$R$^6$, —N(O)$_m$, —NR$^7$R$^8$, —C(O)R$^9$, —C(O)OR$^9$, —N=NR$^7$, —NR$^{10}$—C(O)R$^{11}$, —NR$^{12}$—C(O)—OR$^{13}$, —C(O)NR$^{14}$R$^{15}$, —NR$^{16}$S(O)$_n$R$^{17}$, —S(O)$_n$NR$^{18}$R$^{18'}$, —OR$^{19}$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl. $R^{70}$ is —OH, —NH$_2$, —SH, —CN, —CF$_3$, —NO$_2$, oxo, halogen, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl.

In some embodiments, $R^{69}$ is halogen, —CN, —CF$_3$, —S(O)$_n$R$^6$, —N(O)$_m$, —NR$^7$R$^8$, —C(O)R$^9$, —C(O)OR$^9$, —N=NR$^7$, —NR$^{10}$—C(O)R$^{11}$, —NR$^{12}$—C(O)—OR$^{13}$, —C(O)NR$^{14}$R$^{15}$, —NR$^{16}$S(O)$_n$R$^{17}$, —S(O)$_n$NR$^{18}$R$^{18'}$, —OR$^{19}$, halomethyl, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl. $R^{72}$ is —OH, —NH$_2$, —SH, —CN, —CF$_3$, —NO$_2$, oxo, halogen, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl.

In some embodiments, $L^5$ is a bond, substituted or unsubstituted alkylene or substituted or unsubstituted heteroalkylene. In some embodiments, $L^5$ is a bond, $R^{74}$-substituted or unsubstituted alkylene, or $R^{74}$-substituted or unsubstituted heteroalkylene. $R^{74}$ is —OH, —NH$_2$, —SH, —CN, —CF$_3$, —NO$_2$, oxo, halogen, $R^{75}$-substituted or unsubstituted alkyl, $R^{75}$-substituted or heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl. In some embodiments, $L^5$ is a bond. In some embodiments, $L^5$ is a bond, and $R^{21}$ is substituted phenyl, preferably NH$_2$-substituted phenyl.

In some embodiments, $L^6$ is a bond, —S(O)—, —S(O)$_2$— or —C(O)—. In some embodiments, $L^6$ is —C(O)—.

In some embodiments, $L^7$ is a bond, —N(R$^{78}$)—, substituted or unsubstituted alkylene, or substituted or unsubstituted heteroalkylene. In some embodiments, $L^7$ is a bond, —N(R$^{78}$)—, $R^{76}$-substituted or unsubstituted alkylene, or $R^{76}$-substituted or unsubstituted heteroalkylene. $R^{76}$ is —OH, —NH$_2$, —SH, —CN, —CF$_3$, —NO$_2$, oxo, halogen, $R^{77}$-substituted or unsubstituted alkyl, $R^{77}$-substituted or heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl.

In some embodiments, $R^{78}$ is hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl. In some embodiments, $R^{78}$ is hydrogen, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl. $R^{79}$ is —OH, —NH$_2$, —SH, —CN, —CF$_3$, —NO$_2$, oxo, halogen, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl.

In some embodiments, $R^{71}$, $R^{73}$, $R^{75}$, $R^{77}$ and $R^{80}$ are independently halogen, —CN, —CF$_3$, —OH, oxo, —NH$_2$, —NO$_2$, —SH, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^8$ is a bond, —C(O)—, —NR$^{20'}$— or —CHR$^{20'}$—, where $R^{20'}$ is as defined above. In some embodiments, $L^8$ is a bond, —NH— or —CH$_2$—. In some embodiments, $L^8$ is a bond. In some embodiments, $L^8$ is —C(O)—. In some embodiments, $L^8$ is —NH—. In some embodiments, $L^8$ is —CH$_2$—.

In another aspect, compounds are provided having the formula:

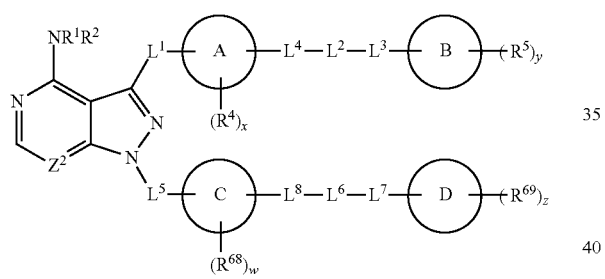

VII wherein $R^1$, $R^2$, $R^4$, $R^5$, $R^{68}$, $R^{69}$, w, x, y, z, ring A, ring B, ring C, ring D, $L^1$, $L^2$, $L^3$, $L^4$, $L^5$, $L^6$, $L^7$, and $L^8$ are as defined above. In some embodiments, $L^1$, $L^5$ and $L^8$ are bonds, $L^2$ is —C(O)—, $L^3$ and $L^7$ are —NH—, ring A is arylenyl, ring B and ring D are independently aryl, preferably phenyl, ring C is heterocycloalkylenyl, x and w are 0, y and z are 1, and $R^5$ and $R^{69}$ are independently halomethyl, preferably trifluoromethyl.

In some embodiments, the Ire1 inhibitor has one of the following formulae:

TABLE 1

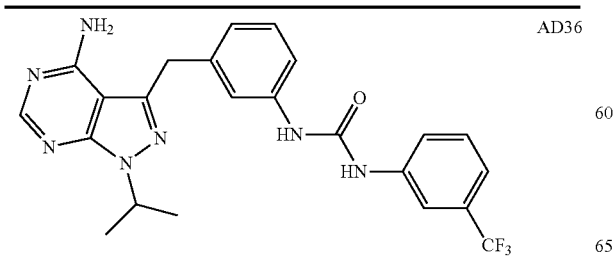

AD36

TABLE 1-continued

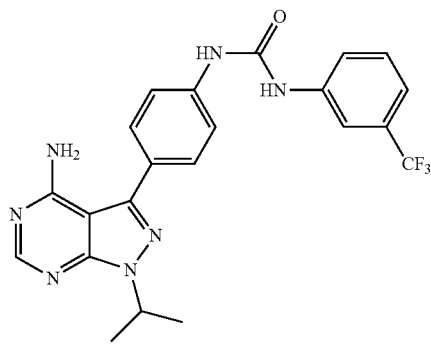 [SMILES: CC(C)n1nc(-c2ccc(NC(=O)Nc3cccc(C(F)(F)F)c3)cc2)c2c(N)ncnc21]

AD57

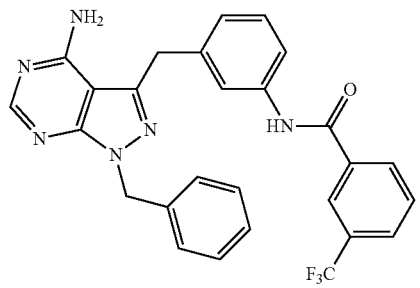 [SMILES: Nc1ncnc2c1c(Cc1cccc(NC(=O)c3cccc(C(F)(F)F)c3)c1)nn2Cc1ccccc1]

BB5

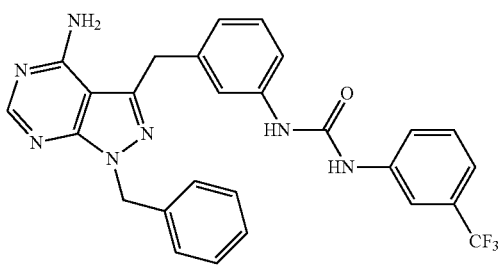 [SMILES: Nc1ncnc2c1c(Cc1cccc(NC(=O)Nc3cccc(C(F)(F)F)c3)c1)nn2Cc1ccccc1]

BB6

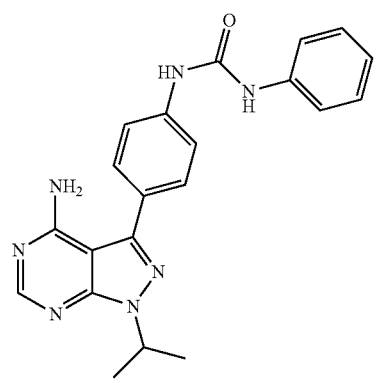 [SMILES: CC(C)n1nc(-c2ccc(NC(=O)Nc3ccccc3)cc2)c2c(N)ncnc21]

AD58

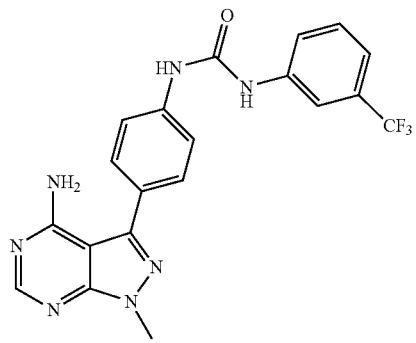 [SMILES: Cn1nc(-c2ccc(NC(=O)Nc3cccc(C(F)(F)F)c3)cc2)c2c(N)ncnc21]

AD59

TABLE 1-continued
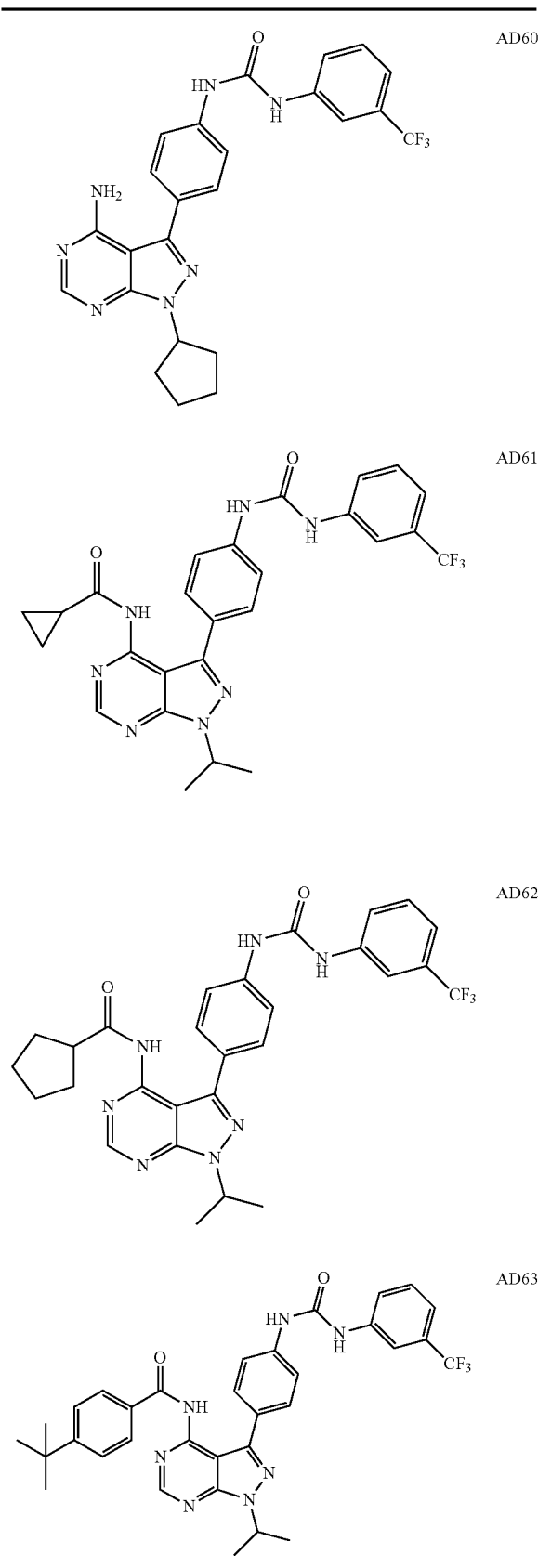
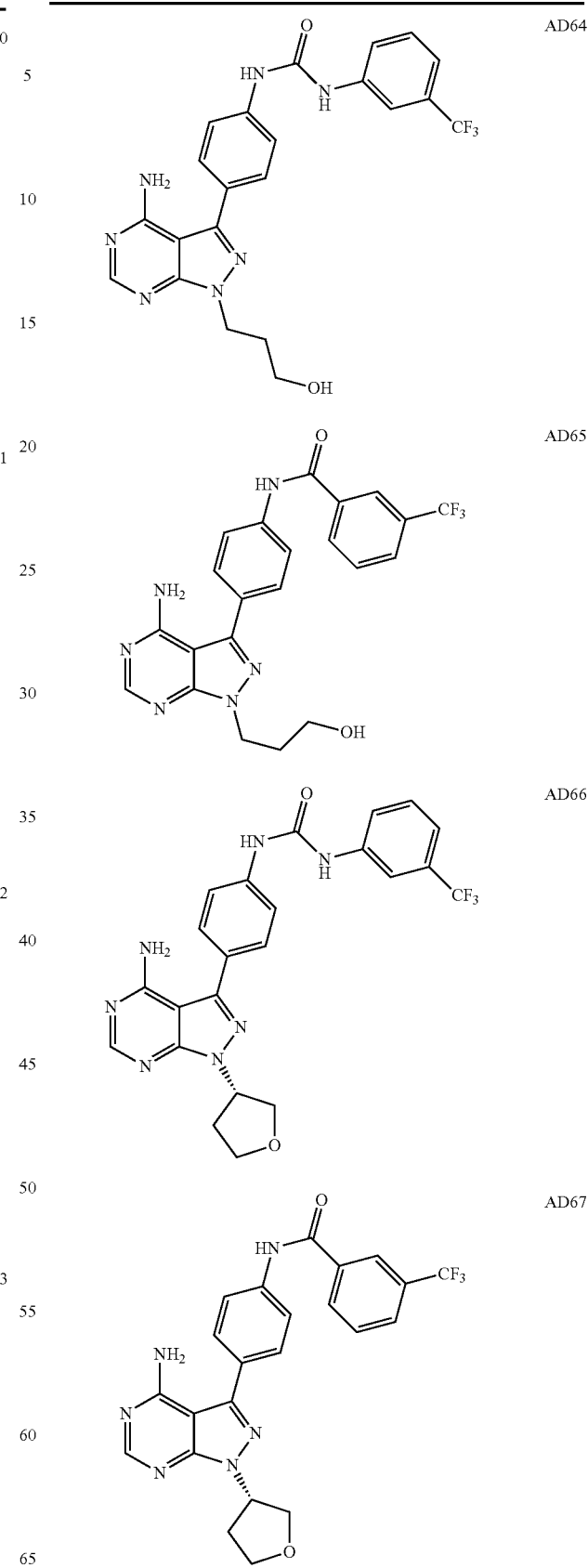

TABLE 1-continued
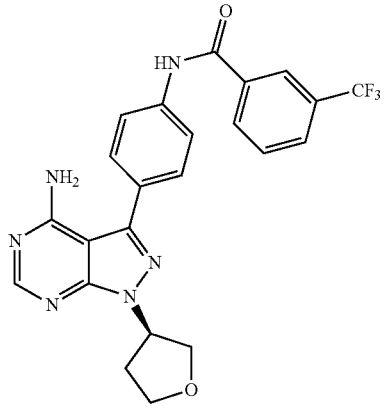 [SMILES: Nc1ncnc2c1c(-c1ccc(NC(=O)c3cccc(C(F)(F)F)c3)cc1)nn2[C@@H]1CCOC1]
AD68
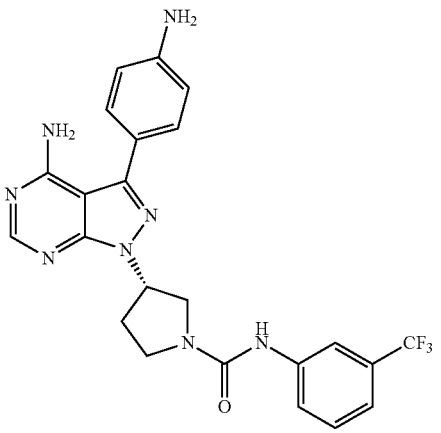 [SMILES: Nc1ccc(-c2nn([C@H]3CCN(C(=O)Nc4cccc(C(F)(F)F)c4)C3)c3ncnc(N)c23)cc1]
AD71a
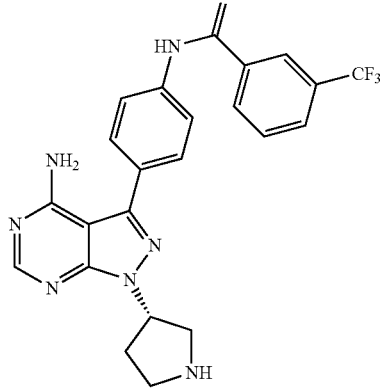
AD69
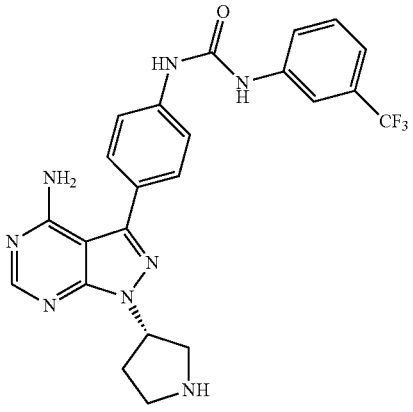 [SMILES: Nc1ncnc2c1c(-c1ccc(NC(=O)Nc3cccc(C(F)(F)F)c3)cc1)nn2[C@H]1CCNC1]
AD71b
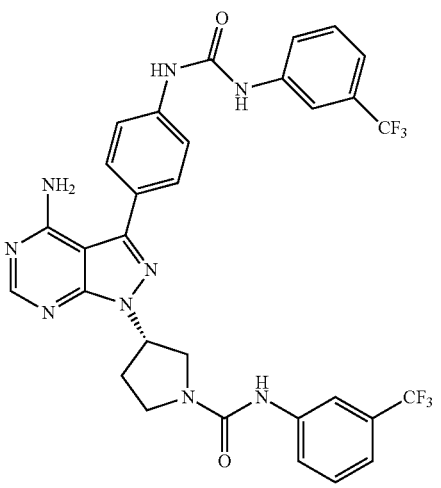 [SMILES: Nc1ncnc2c1c(-c1ccc(NC(=O)Nc3cccc(C(F)(F)F)c3)cc1)nn2[C@H]1CCN(C(=O)Nc2cccc(C(F)(F)F)c2)C1]
AD70
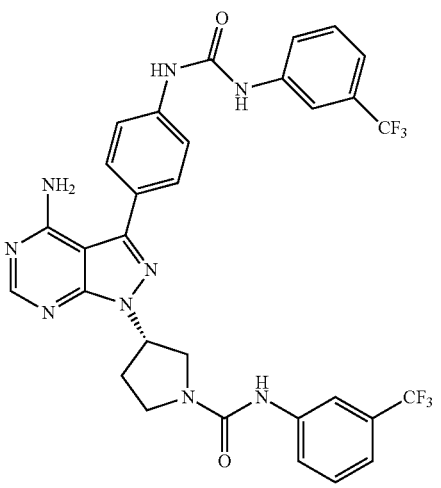 [SMILES: Nc1ncnc2c1c(-c1ccc(NC(=O)Nc3cccc(C(F)(F)F)c3)cc1)nn2[C@H]1CCN(C(=O)Nc2cccc(C(F)(F)F)c2)C1]
AD71c TABLE 1-continued
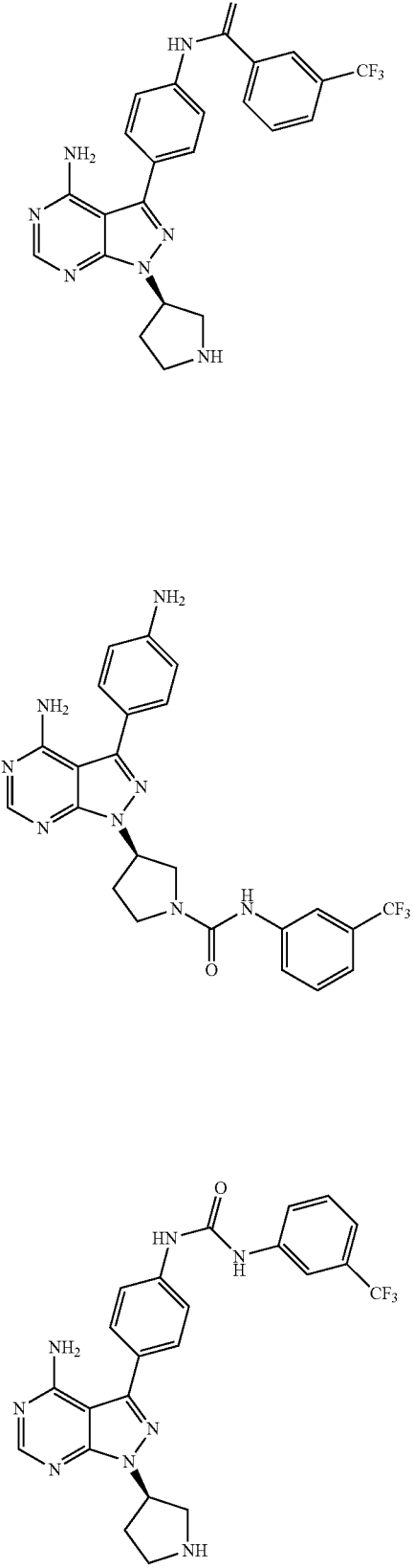
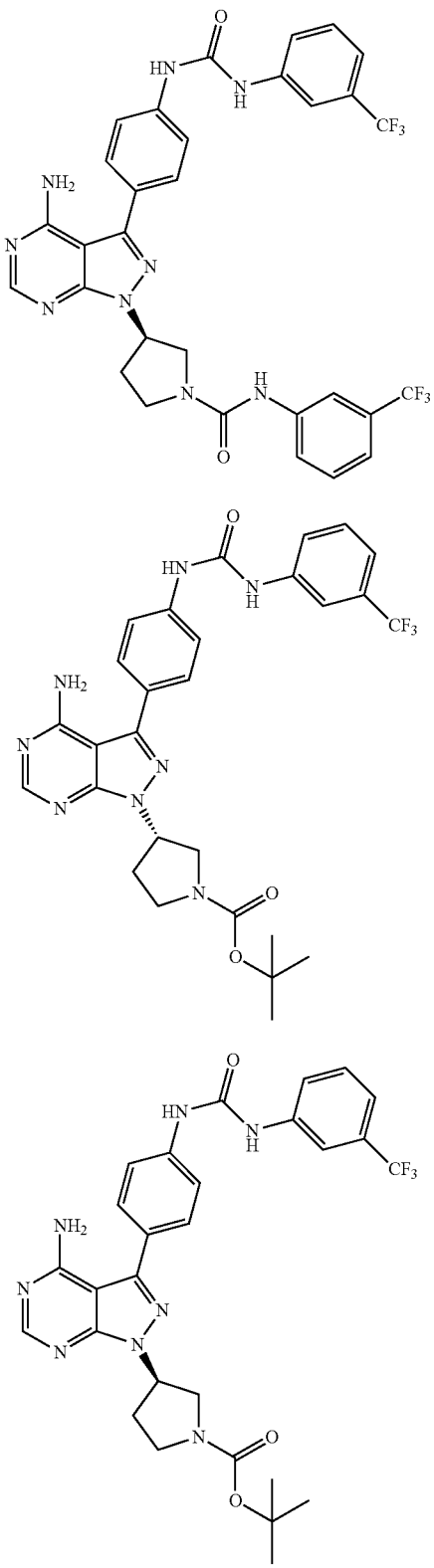
In one embodiment, the Ire1 inhibitor is AD59, AD60, or AD73c. AD60, for example, can inhibit both yIre1 and hIre1. In another embodiment, the Ire1 inhibitor is AD64, AD71c, or AD73c. In one embodiment, the Ire1 inhibitor is AD73c. In one embodiment, the Ire1 inhibitor can inhibit Ire1 activity at low micromolar levels such as, for example, having an IC50 of less than about 1 µM.

In some embodiments, one or more substituted groups described in any of the above Formulae is substituted with at least one substituent group. More specifically, in some embodiments, at least one substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, or substituted heteroarylene described in the above Formulae is substituted with at least one substituent group. In other embodiments, at least one or all of these groups are substituted with at least one size-limited substituent group. Alternatively, at least one or all of these groups are substituted with at least one lower substituent group.

In other embodiments of the Formulae, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted aryl is a substituted or unsubstituted $C_4$-$C_8$ aryl, each substituted or unsubstituted heteroaryl is a substituted or unsubstituted 4 to 8 membered heteroaryl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene substituted or unsubstituted $C_4$-$C_8$ cycloalkylene, each substituted or unsubstituted heterocycloalkylene is a substituted or unsubstituted 4 to 8 membered heterocycloalkylene, and each substituted or unsubstituted arylene is a substituted or unsubstituted $C_4$-$C_8$ arylene, each substituted or unsubstituted heteroarylene is a substituted or unsubstituted 4 to 8 membered heteroarylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted aryl is a substituted or unsubstituted $C_5$-$C_7$ aryl, each substituted or unsubstituted heteroaryl is a substituted or unsubstituted 5 to 7 membered heteroaryl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene substituted or unsubstituted $C_5$-$C_6$ cycloalkylene, and each substituted or unsubstituted heterocycloalkylene is a substituted or unsubstituted 5 to 7 membered heterocycloalkylene, each substituted or unsubstituted arylene is a substituted or unsubstituted $C_5$-$C_7$ arylene, each substituted or unsubstituted heteroarylene is a substituted or unsubstituted 5 to 7 membered heteroarylene.

In any of the Formulae above, the substituents described herein, including linking moieties (e.g., alkylene or heteroalkylene), can be size-limited substituents or lower substituent groups. For example, any alkyl group can be a $C_1$-$C_{10}$, $C_1$-$C_6$, or $C_1$-$C_4$ alkyl group. Any heteroalkyl group can have 2-10, 2-6, or 2-4 members. Any cycloalkyl group can be a $C_3$-$C_8$, $C_5$-$C_7$, or $C_5$-$C_6$ cycloalkyl group. Any heterocycloalkyl group can have 3-8, 4-7, or 5-6 members. Any aryl group can be a $C_5$-$C_8$ or $C_5$-$C_6$ aryl group. Any heteroaryl group can have 5-8 or 5-6 members.

III. Methods

In another aspect, a method of inhibiting Ire1 activity is provided. The method includes contacting an Ire1 protein with an effective amount of an Ire1 inhibitor as described above thereby inhibiting the Ire1 protein. In some embodiments, the Ire1 protein is contacted with the Ire1 inhibitor in the presence of an Ire1 substrate. In some embodiments, the Ire1 activity that is inhibited is the activity of hIre1, yIre1, or both hIre1 and yIre1.

In another aspect, a method of inhibiting Ire1 activity in a cell is provided. The method includes contacting the cell with an effective amount of an Ire1 inhibitor as described above. In some embodiments, the cell is a mammalian cell, such as a human cell. The cell may be isolated in vitro, form part of a tissue in vitro, or may form part of an organism. In some embodiments, the Ire1 activity that is inhibited is the activity of hIre1, yIre1, or both hIre1 and yIre1.

An Ire1 inhibitor, as used herein, may be a compound that is capable of reducing Ire1 enzymatic activity relative to the amount of Ire1 enzymatic activity in the absence of the compound. In some embodiments, one or more functions of Ire1 and/or one or more downstream effects of Ire1 is/are reduced. For example, in one embodiment, the Ire1 inhibitor decreases one or more of: activation of Ire1 by misfolded proteins, initiation of UPR, trans-autophosphorylation, co-factor binding, translation of Hac1, translation of Xbp1, and corrected protein folding. For example, as Xbp1 overexpression is correlated to multiple myeloma, in some embodiments, an effective amount of Ire1 inhibitor is an amount that decreases Xbp1 expression relative to the expression of Xbp1 in the absence of Ire1 inhibitor. In another embodiment, an effective amount of Ire1 inhibitor is an amount that sufficiently decreases Ire1 activity in the cell to reduce UPR relative to the amount of UPR in the absence of Ire1 inhibitor.

In one embodiment, the method of inhibiting Ire1 activity comprises direct binding of the Ire1 inhibitor (i.e., a direct Ire1 inhibitor) to Ire1. In another embodiment, the inhibiting of Ire1 activity by the Ire1 inhibitor (i.e., an indirect Ire1 inhibitor) is indirect (e.g., by modulating another effector that affects Ire1 activity).

In one embodiment, the method may be conducted in vitro by assessing direct inhibition of Ire1 RNase activity.

Also provided herein is a method of treating a disease caused by activity (e.g., abnormally high activity such as hyperactivity) of Ire1 in a subject in need of such treatment. The method includes administering to the subject a therapeutically effective amount of an Ire1 inhibitor as described above. Ire1 hyperactivity is an increased amount of activity that is more than the average amount of Ire1 activity in a particular subject or a population of healthy subjects. The increased amount of Ire1 activity may result in, for example, excessive amounts of cell proliferation thereby causing the disease state.

The Ire1 inhibitors provide a means to pharmacologically decrease the ability of rapidly proliferating cells (e.g., cancer cells) to survive. A strong causal relationship between Ire1 activity and cancer has been established for multiple myeloma. Carrasco D R, et al. 2007. The Differentiation and Stress Response Factor XBP-1 Drives Multiple Myeloma Pathogenesis. Cancer Cell 11: 349-60. The Ire1 inhibitors provided herein provide compounds useful for treating multiple myeloma as well as for treating a panel of additional cancers and diseases in which Ire1 activation has been implicated. Accordingly, in some embodiments, the disease is a cancer, an inflammatory disease, or an autoimmune disease. Exemplary cancers include, but are not limited to, breast cancer and multiple myeloma. In some embodiments, the disease is multiple myeloma. Exemplary inflammatory diseases include, but are not limited to, asthma, chronic inflammation, chronic prostatitis, glomerulonephritis, hypersensitivities, inflammatory bowel diseases, pelvic inflammatory disease; reperfusion injury, rheumatoid arthritis, transplant rejection, and vasculitis. Exemplary autoimmune diseases include, but are not limited to, XBP1-linked Crohn's disease, Coeliac disease, diabetes mellitus type 1 (IDDM), systemic lupus erythematosus (SLE), Sjögren's syndrome, Churg-Strauss Syndrome, Hashimoto's thyroiditis, Graves' disease, idiopathic thrombocytopenic purpura, and rheumatoid arthritis. In some embodiments, the disease is XBP1-linked Crohn's disease.

The subject of treatment for the disease is typically a mammal. The mammals treated with the Ire1 inhibitor may be humans, nonhuman primates, and/or non-human mammals (e.g., rodents, canines).

IV. Assays

The modulation of Ire1 activity may be identified by contacting a test compound with Ire1 proteins in a solution.

For example, inhibition can be achieved by binding of the compound to Ire1 in state of a monomer, dimer, or higher-order oligomer. The inhibition can be achieved due to disruption of Ire1 oligomers or dimers, altering conformation of Ire1, or competition of the inhibitor with the RNA substrate for binding to Ire1. The inhibitor can act competitively, non-competitively, uncompetitively, or in a mixed mode.

Inhibition of Ire1 can be detected by measuring enzymatic activity of Ire1 in RNA cleavage assay. The RNA cleavage assays uses, for example, radioactively labeled RNA, fluorescently labeled RNA, unlabeled RNA, or RNA labeled by other means. Inhibition can alternatively be measured using Ire1 kinase activity assays. Inhibition can alternatively be measured using biophysical methods such as dynamic light scattering, ultracentrifugation, isothermal calorimetry, etc. that detect protein-protein or protein-ligand interactions. Inhibitors can affect the RNase activity of Ire1, the kinase activity of Ire1, and/or the oligomeric state of Ire1.

V. Pharmaceutical Compositions

In another aspect, the present invention provides pharmaceutical compositions comprising a compound of the invention in combination with a pharmaceutically acceptable carrier. The pharmaceutical compositions include optical isomers, diastereomers, or pharmaceutically acceptable salts of the inhibitors disclosed herein. The compound included in the pharmaceutical composition may be covalently attached to a carrier moiety, as described above. Alternatively, the compound included in the pharmaceutical composition is not covalently linked to a carrier moiety.

A "pharmaceutically suitable carrier," as used herein refers to pharmaceutical excipients, for example, pharmaceutically or physiologically acceptable organic or inorganic carrier substances suitable for enteral or parenteral application that do not deleteriously react with the compound. Suitable pharmaceutically acceptable carriers include water, salt solutions (such as Ringer's solution), alcohols, oils, gelatins, carbohydrates (such as lactose, amylose or starch), fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., decreasing Ire1 activity and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., Alzheimer's disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

VI. Examples

The following examples are meant to illustrate certain embodiments of the invention and not to limit the scope of the invention described herein.

Example 1

Generic Synthesis Schemes

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

For example, Scheme 1 following provides one of a variety of overall synthetic strategies that may be employed in the synthesis of compounds described herein. Substituents in Scheme 1 are as described herein above.

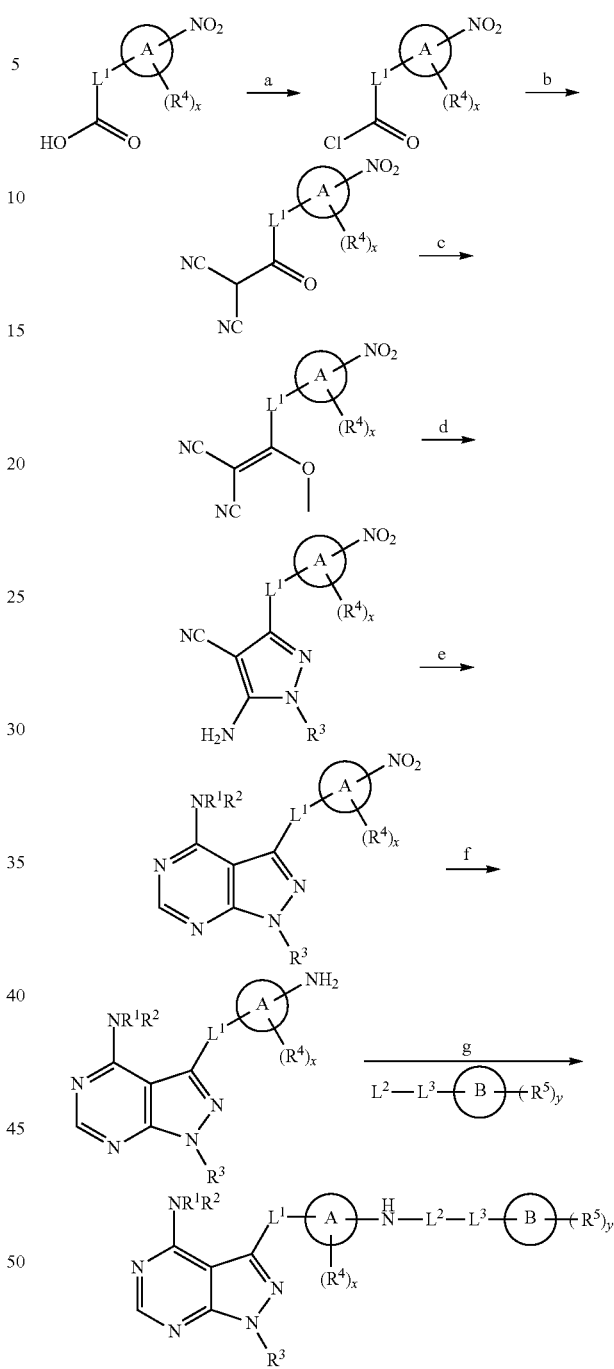

Scheme 1

In Scheme 1, Step a, an acid starting material may be reacted with oxalyl chloride, e.g., in DMF and $CH_2Cl_2$, to afford the acid chloride. In Step b, the acid chloride may be reacted with malononitrile and NaH in, e.g., THF, to afford the substituted malononitrile. In Step c, the compound may be further reacted with dimethyl sulfate and $NaHCO_3$ in, e.g., dioxane and water, to afford the enol ether. In Step d, the enol ether may be reacted with a hydrazine in, e.g., THF, to afford the pyrazole. In Step e, the pyrazole may be further reacted with an amide to afford the pyrazolo[3,4-d]pyrimidine amine. In Step f, the pendant nitrate may be reduced to afford the amine. Finally, in Step g, elaboration at the pendant amine may be employed to afford a compound of the invention.

Optionally, one or more functionalities described herein and in Scheme 1 may be protected during synthesis and subsequently deprotected by methods well known in the art. Exemplary amine protecting groups include, but are not limited to, carbobenzyloxy (Cbx), p-methyoxybenzyl carbonyl (Boz), tert-butyloxycarbonyl (Boc), 9-fluorenylmethyloxy carbonyl (FMoc), benzyl (Bn), p-methoxybenzyl (PMB), 2,3-dimethoxybenzyl (DMPM), p-methoxyphenyl (PMP), tosyl (Ts), allyloxycarbonyl (Alloc), and the like.

Formation of carbon-carbon bonds, for example between aryl functionalities, is available by a variety of routes known in the art. For example, the Suzuki reaction depicted in Scheme 2 is the reaction of an aryl- or vinyl-boronic acid with an aryl- or vinyl-halide, catalyzed by a Pd complex. Exemplary Pd complexes include, but are not limited to, tetrakis (triphenylphosphine)palladium(0), and polymer-bound tetrakis palladium, as known in the art.

Scheme 2

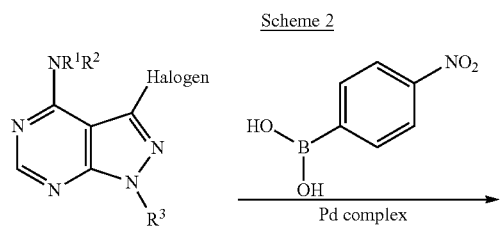

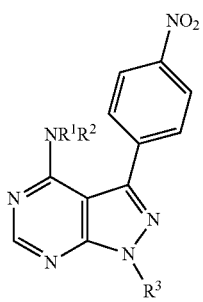

Example 2

Syntheses

Starting materials were purchased from Sigma-Aldrich. Reactions were monitored by thin layer chromatography (TLC), and compounds were characterized by liquid chromatography-mass spectrometry (LC-MS) and nuclear magnetic resonance (NMR) spectroscopy. Compounds were synthesized based on established routes for preparing pyrazolopyrimidines (Bishop et al., 1999, *J American Chemical Society* 121:627-631; Bishop et al., 1998, *Curr Biol* 8:257-266; Blethrow et al., 2004, *Curr Protoc Mol Biol Chapter* 18, Unit 18 11; Apsel et al., 2008, *Nat. Chem. Biol.* 4:691-699; Dar et al., 2008, Chem. Biol. 20:1015-1022) with modifications as described herein.

Example 2.1

Synthesis of AD36: 1-(3-((4-amino-1-isopropyl-1H-pyrazolo[3,4-d]pyrimidin-3-yl)methyl)phenyl)-3-(3-(trifluoromethyl)phenyl)urea

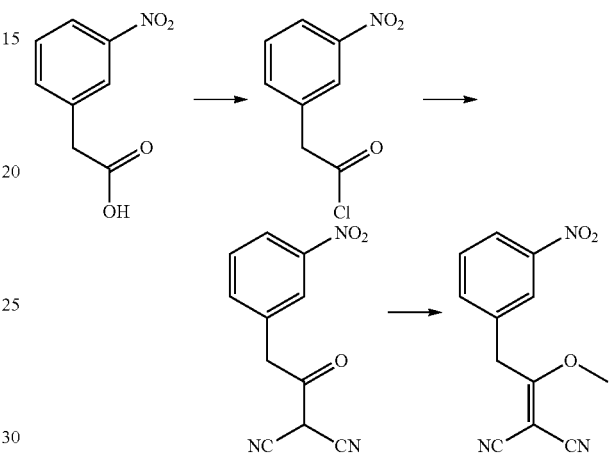

Synthesis of intermediate 2-(1-methoxy-2-(3-nitrophenyl) ethylidene)malononitrile. To a solution of 3-nitrophenyl acetic acid (5 g, 27.6 mmol; Sigma-Aldrich) was added oxalyl chloride (12 mL, 138 mmol) and DMF (0.1 mL) in 40 mL $CH_2Cl_2$. The reaction mixture was stirred for 6 hours at room temperature yielding a clear yellow solution. Solvent was removed in vacuo to afford a yellow solid of the acid chloride, which was washed with $CH_2Cl_2$ three times and carried on directly to the next step. The acid chloride was dissolved in 10 mL of THF and added dropwise to a reaction flask containing an ice-cold solution of malononitrile (2.7 g, 41 mmol) and NaH (3.5 g of a 60% paraffin oil emulsion, 88.3 mmol) in THF. The reaction was stirred for 4 hours and warmed to room temperature, after which 25 mL of 2N HCl was added. The aqueous layer was extracted three times with EtOAc. The organic extracts were combined and concentrated in vacuo. The crude material containing 2-(2-(3-nitrophenyl)acetyl) malononitrile was dissolved in $H_2O$ (7 mL) and 1,4-dioxane (42 mL), to which $NaHCO_3$ (11.5 g, 138 mmol) and dimethyl sulfate (10.5 mL, 110 mmol) were added. The reaction mixture was heated to 80° C. and left stirring for 12 hours. The reaction mixture was diluted with EtOAc (100 mL) and brine (100 mL). The aqueous portion was extracted with EtOAc (3×100 mL). The combined organic fractions were dried over $MgSO_4$, filtered, and concentrated in vacuo. The recovered solid was purified by silica gel chromatography (100% chloroform). Fractions containing the desired enol ether were pooled, concentrated, and dissolved in hot MeOH. The solution was cooled, and fine white crystals formed overnight, which were recovered by filtration and washed with ice-cold MeOH to afford 2-(1-methoxy-2-(3-nitrophenyl)ethylidene) malononitrile. $^1$H NMR (400 MHz, DMSO): δ 7.78 (1H, d), 7.72 (t, 1H), 8.22 (d, 1H), 8.25 (s, 1H), 4.36 (s, 2H), 4.04 (s, 3H).

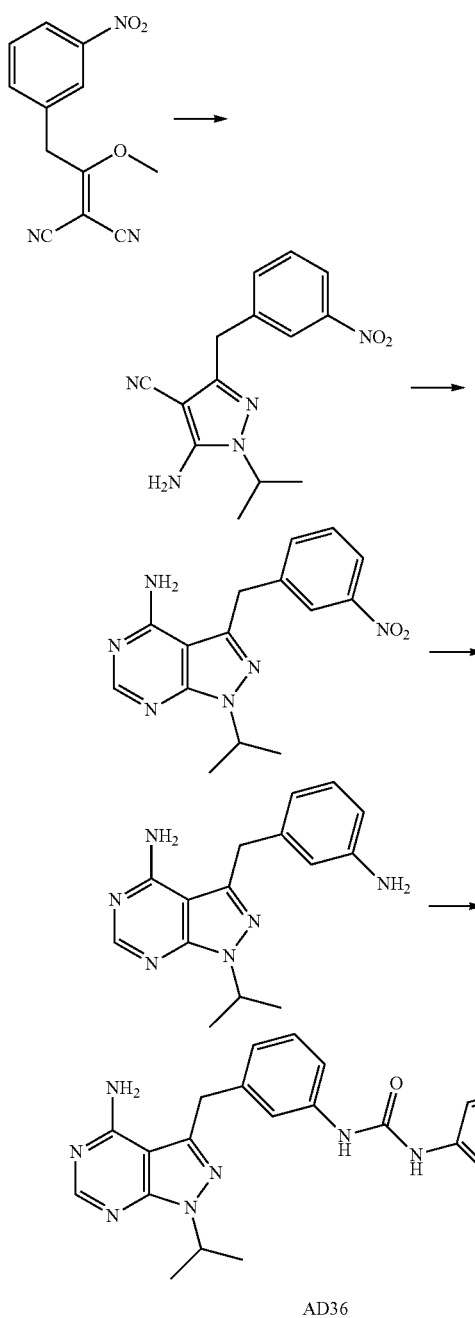

AD36

The intermediate 2-(1-methoxy-2-(3-nitrophenyl)ethylidene)malononitrile (1.2 g, 4.7 mmol) was combined with isopropylhydrazine-HCl (0.57 g, 5.2 mmol; Sigma-Aldrich), 1.4 mL triethylamine in 50 mL EtOH for 2 hours at RT. The reaction was concentrated in vacuo, suspended in brine, and extracted with chloroform. The organic layer was dried over MgSO$_4$. Following, the organic suspension was filtered, concentrated in vacuo, and purified on silica gel in 1% MeOH: CHCl$_3$ to yield 3-(3-nitrobenzyl)-5-amino-1-isopropyl-1H-pyrazole-4-carbonitrile (ESI-MS m/z [M+H]+ found 286.4, calculated 286.12). The product was combined with formamide (1.5 mL) and heated to 160° C. overnight. H$_2$O was added to the cooled reaction, and the precipitate was filtered and dried to yield 3-(3-nitrobenzyl)-1-isopropyl-1H-pyrazolo[3,4-d]pyrimidin-4-amine (ESI-MS m/z [M+H]+ found 313.4, calculated 313.13). This precipitated intermediate was then mixed with excess zinc dust, 5 mL THF, and 0.4 mL HOAc for 12 hours under argon at room temperature. Afterwards the reaction was filtered through Celite®, extracted with EtOAc, and concentrated in vacuo to yield 3-(3-aminobenzyl)-1-isopropyl-1H-pyrazolo[3,4-d]pyrimidin-4-amine ESI-MS m/z [M+H]+ found 283.11, calculated 282.16. To the reduced precursor, molar equivalents of 3-(trifluoromethyl)phenyl isocyanate (Sigma-Aldrich) were added dropwise in ice-cold CH$_2$Cl$_2$. The reaction proceeded until completion as judged by TLC, was concentrated in vacuo, resuspended in 50:50 H$_2$O—CH$_3$CN, and purified on a C18 column in CH$_3$CN/H$_2$O/0.1% TFA (1-100% gradient) to yield final compound AD36 1-(3-((4-amino-1-isopropyl-1H-pyrazolo[3,4-d]pyrimidin-3-yl)methyl)phenyl)-3-(3-(trifluoromethyl)phenyl)urea (ESI-MS m/z [M+H]+ found 470.5, calculated 470.18; $^1$H NMR (400 MHz, DMSO): δ 9.25 (1H, s), 8.97 (s, 1H), 8.36 (s, 1H), 8.05 (s, 1H), 7.48-7.54 (m, 2H), 7.41 (s, 1H), 7.30 (d, J=8 Hz, 2H), 7.20 (t, J=8 Hz, 1H0, 6.88 (d, J=8 Hz, 1H), 5.03 (septet, J=8 Hz, 1H), 1.48 (s, 6H). $^{13}$C NMR (400 MHz, DMSO): δ 22.15, 33.44, 49.21, 98.32, 116.48 (d), 117.03, 118.92, 122.16, 122.67, 124.70 (q), 129.33, 129.98 (q), 130.47 (q), 139.50, 140.07, 141.15, 145.31, 150.15, 151.77, 152.94, 154.32, 159.10 (q))

Example 2.2

Synthesis of BB5: N-(3-((4-amino-1-benzyl-1H-pyrazolo[3,4-d]pyrimidin-3-yl)methyl)phenyl)-3-(trifluoromethyl)benzamide

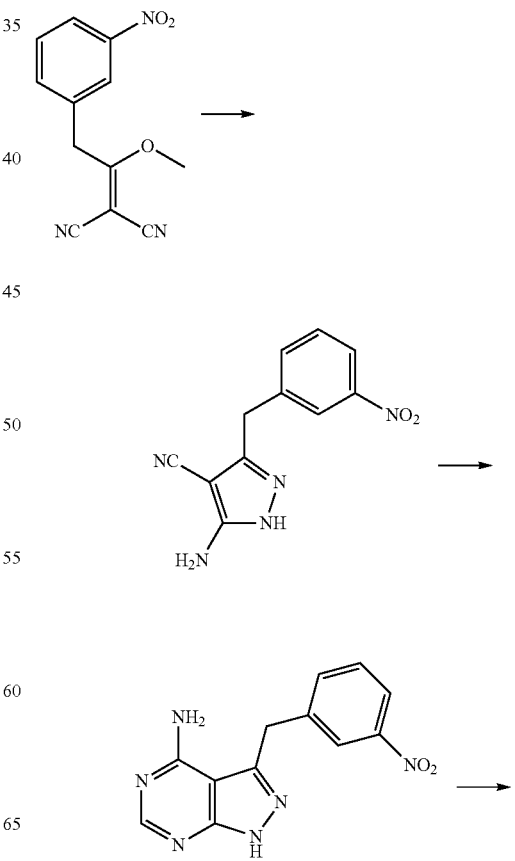

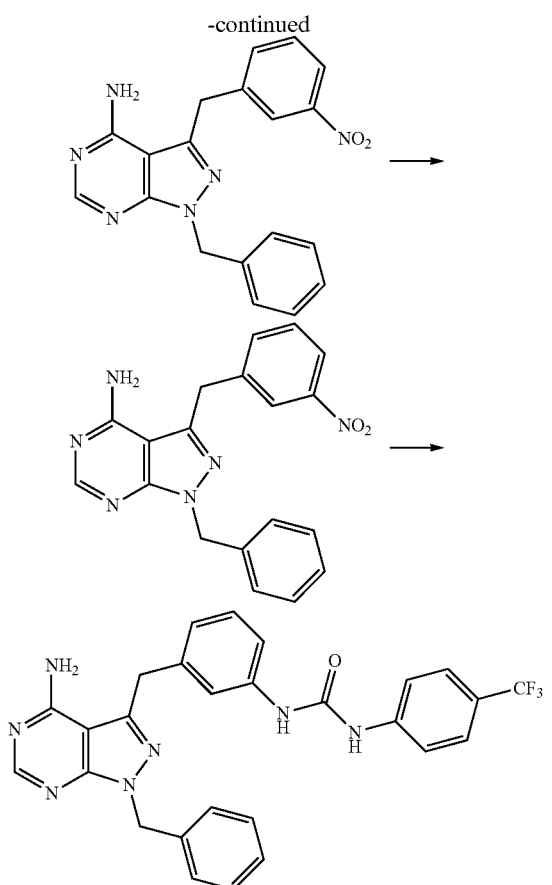

judged by TLC, was concentrated in vacuo, resuspended in 50:50 H₂O—CH₃CN, and purified on a C18 column in CH₃CN/H₂O/0.1% TFA (1-100% gradient) to yield final compound BB5 N-(3-((4-amino-1-benzyl-1H-pyrazolo[3,4-d]pyrimidin-3-yl)methyl)phenyl)-3-(trifluoromethyl)benzamide (ESI-MS m/z [M+H]+ found 503.4, calculated 503.2).

Example 2.3

Synthesis of BB6: 1-(3-((4-amino-1-benzyl-1H-pyrazolo[3,4-d]pyrimidin-3-yl)methyl)phenyl)-3-(3-(trifluoromethyl)phenyl)urea

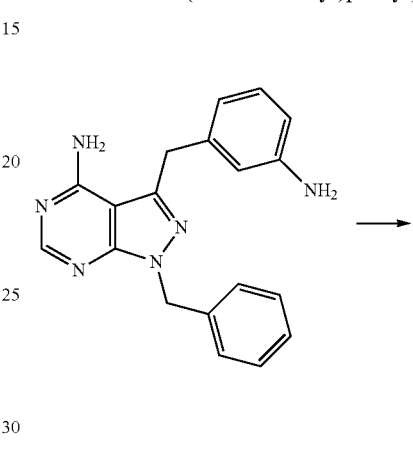

The intermediate 2-(1-methoxy-2-(3-nitrophenyl)ethylidene)malononitrile (0.97 g, 4.0 mmol) was combined with hydrazine (0.3 mL, 6.0 mmol; Sigma-Aldrich) in 10 mL EtOH for 90 minutes at room temperature. Afterwards the reaction was concentrated in vacuo, suspended in brine, and extracted with chloroform (3×50 mL). The organic layer was dried over MgSO₄, then filtered and concentrated in vacuo to afford 3-(3-nitrobenzyl)-5-amino-1H-pyrazole-4-carbonitrile (ESI-MS m/z [M+H]+ found 244.5, calculated 244.1). The product was combined with formamide (1.5 mL) and heated to 160° C. overnight. H₂O was added to the cooled reaction, and the precipitate was filtered and dried to afford 3-(3-nitrobenzyl)-1H-pyrazolo[3,4-d]pyrimidin-4-amine (ESI-MS m/z [M+H]+ found 271.4, calculated 271.1). This recovered solid (50 mg, 0.19 mmol) was then added to a solution containing benzyl bromide (0.1 mL, 0.28 mmol), K₂CO₃ (0.125 g), and DMF (1.0 mL). The reaction mixture was purged with argon and stirred overnight at 80° C. The reaction was filtered to remove solid K₂CO₃. The filtrate was combined with brine, and the organic product was extracted in CH₂Cl₂ (3×50 mL) to afford 3-(3-nitrobenzyl)-1-benzyl-1H-pyrazolo[3,4-d]pyrimidin-4-amine (ESI-MS m/z [M+H]+ found 361.4, calculated 361.1). This intermediate was then mixed with excess zinc dust, 5 mL THF, 0.4 mL HOAc for 12 hours under argon at room temperature. Afterwards the reaction was filtered through Celite®, extracted with EtOAc, and concentrated in vacuo to afford 3-(3-aminobenzyl)-1-benzyl-1H-pyrazolo[3,4-d]pyrimidin-4-amine (ESI-MS m/z [M+H]+ found 331.5, calculated 331.2). To the reduced precursor, molar equivalents of 3-(trifluoromethyl) benzoyl chloride (Sigma-Aldrich) were added dropwise in ice-cold CH₂Cl₂. The reaction proceeded until completion as To the intermediate 3-(3-aminobenzyl)-1-benzyl-1H-pyrazolo[3,4-d]pyrimidin-4-amine, molar equivalents of 3-(trifluoromethyl)phenyl isocyanate (Sigma-Aldrich) were added dropwise in ice-cold CH₂Cl₂. The reaction proceeded until completion as judged by TLC, was concentrated in vacuo, resuspended in 50:50 H₂O—CH₃CN, and purified on a C18 column in CH₃CN/H₂O/0.1% TFA (1-100% gradient) to yield final compound BB6 1-(3-((4-amino-1-benzyl-1H- pyrazolo[3,4-d]pyrimidin-3-yl)methyl)phenyl)-3-(3-(trifluoromethyl)phenyl)urea (ESI-MS m/z [M+H]+ found 518.4, calculated 518.2).

Example 2.4

Synthesis of AD57: 1-(4-(4-amino-1-isopropyl-1H-pyrazolo[3,4-d]pyrimidin-3-yl)phenyl)-3-(3-(trifluoromethyl)phenyl)urea

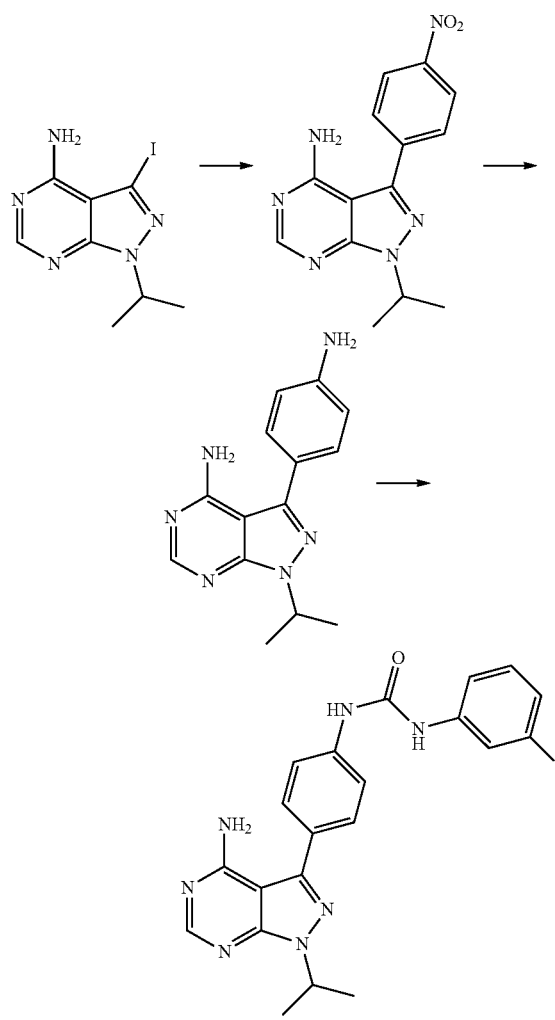

4-nitrophenyl boronic acid (100 mg, 0.330 mmol; Sigma-Aldrich) was coupled to 3-iodo-1-isopropyl-1H-pyrazolo[3,4-d]pyrimidin-4-amine (140 mg, 0.8248 mmol; Apsel et al., 2008) via the Suzuki reaction in 6 mL 1,2 methoxy ethane, 1 mL of saturated sodium carbonate, 1.65 mL EtOH, and 200 mg of polymer-bound tetrakis palladium. The reaction was stirred under argon for 12 hours at room temperature, filtered through Whatman paper to remove palladium, mixed with brine, extracted in chloroform and the product was subsequently purified on silica in EtOAc and concentrated in vacuo. The purified solid 1-isopropyl-3-(4-nitrophenyl)-1H-pyrazolo[3,4-d]pyrimidin-4-amine (ESI-MS m/z [M+H]+ found 299.1, calculated 299.1; 100 mg, 0.336 mmol) was combined with zinc dust, 5 mL THF, and 0.4 mL HOAc for 12 hours at room temperature under argon. Then the reaction mixture was filtered through Celite®, extracted with EtOAc and concentrated in vacuo to yield 3-(4-aminophenyl)-1-isopropyl-1H-pyrazolo[3,4-d]pyrimidin-4-amine (ESI-MS m/z [M+H]+ found 269.1, calculated 269.1). To this reduced product, molar equivalents of 3-(trifluoromethyl)phenyl isocyanate (Sigma-Aldrich) were added dropwise in ice-cold $CH_2Cl_2$. The reaction proceeded until completion as judged by TLC, was concentrated in vacuo, resuspended in 50:50 $H_2O$—$CH_3CN$, and purified on a C18 column in $CH_3CN/H_2O/0.1\%$ TFA (1-100% gradient) to yield AD57 1-(4-(4-amino-1-isopropyl-1H-pyrazolo[3,4-d]pyrimidin-3-yl)phenyl)-3-(3-(trifluoromethyl)phenyl)urea (ESI-MS m/z [M+H]+ found 455.2, calculated 455.2; $^1$H NMR (400 MHz, DMSO): δ 9.48 (s, 1H), 9.42 (s, 1H), 8.39 (s, 1H), 8.07 (s, 1H), 7.70 (d, J=8 Hz, 2H), 7.60 (d, J=8 Hz, 2H), 7.60-7.64 (m, 1H), 7.53 (t, J=8 Hz, 1H), 7.33 (d, J=8 Hz, 1H), 5.10 (septet, J=6.8 Hz, 1H), 1.51 (d, J=6 Hz, 6H), 3.10 (q, J=4 Hz, 1.5H, trace triethylamine), 1.18 (t, J=8 Hz, 2H, trace triethylamine). $^{13}$C NMR (400 MHz, DMSO): δ 9.08 (trace triethylamine), 22.23, 46.20 (trace triethylamine), 49.17, 97.40, 115.45, 116.0 (d), 119.20, 122.34, 124.70 (q), 126.19, 129.35, 130.00 (q), 130.40, 140.85, 141.09, 145.20, 151.70, 152.35, 153.00, 155.72, 159.41 (q)).

Example 2.5

Synthesis of AD59: 1-(4-(4-amino-1-methyl-1H-pyrazolo[3,4-d]pyrimidin-3-yl)phenyl)-3-(3-(trifluoromethyl)phenyl)urea

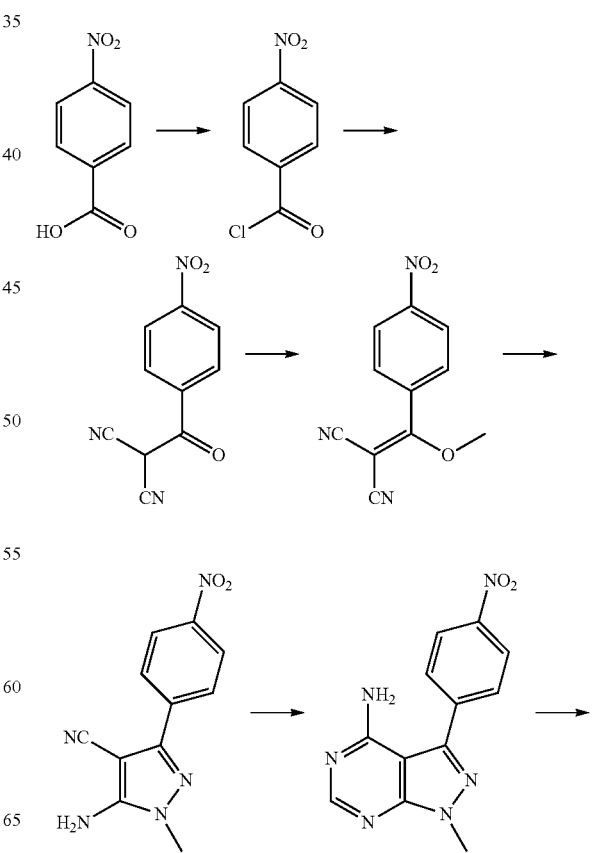

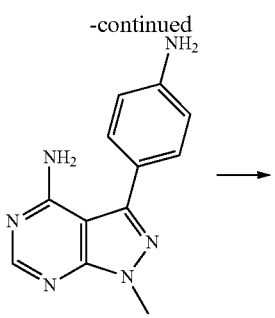

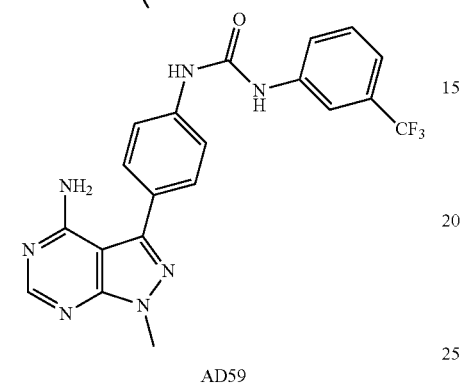

AD59

4-nitrobenzoic acid (5 g, 29.9 mmol; Sigma-Aldrich) was combined with oxaylyl chloride (13.1 mL, 149.5) and DMF (0.1 mL) in 50 mL of dichloromethane and stirred for 2 hours at room temperature to yield a clear yellow solution. The reaction mixture was concentrated in vacuo and washed twice with dichloromethane to yield a bright yellow solid. The solid was dissolved in dry THF and added dropwise to a round bottom flask containing a cooled solution of melanonitrile (2.96 g, 44.9 mmol) and NaH (8.45 g of a 60% oil emulsion, 95.7 mmol) in THF. The reaction was allowed to warm slowly to room temperature and left stirring for 2 hours. Following, 25 mL of 2N HCl and 50 mL of brine were added, and the organic layer was extracted 3 times using EtOAc. The combined organic extracts were dried over $Na_2SO_4$, filtered, and concentrated in vacuo. This brown solid was dissolved in 50 mL of $H_2O$/dioxane (1:8), $NaHCO_3$ (20.1 g, 239 mmol), and dimethyl sulfate (14.2 mL, 150 mmol). The solution was heated to 80° C. for four hours. After cooling, brine was added, and the organic layer was extracted three times using EtOAc. The combined extracts were dried, concentrated in vacuo, and purified on silica in EtOAc-Hexanes (50-100% gradient). The pure yellow solid containing 2-(methoxy(4-nitrophenyl)methylene) malononitrile (100 mg, 0.436 mmol) was added dropwise to monomethylhydrazine (20.1 mg, 0.436 mmol) in ice-cold THF. After 2 hours the reaction was complete as judged by TLC, giving 5-amino-1-methyl-3-(4-nitrophenyl)-1H-pyrazole-4-carbonitrile (ESI-MS m/z [M+H]+ found 243.9, calculated 244.1), which was concentrated in vacuo, suspended in 2 mL of formamide, and heated to 165° C. for 12 hours. Following, the solution was cooled, 8 mL of $H_2O$ was added, and a brown solid was collected by filtration. The purified solid 1-methyl-3-(4-nitrophenyl)-1H-pyrazolo[3,4-d]pyrimidin-4-amine (ESI-MS m/z [M+H]+ found 270.9, calculated 271.1; 60 mg, 0.222 mmol) was combined with zinc dust (0.4 g), 10 mL THF, and 0.25 mL HOAc for 12 hours at room temperature. Afterwards, the reaction mixture was filtered through Celite®, extracted with EtOAc, and concentrated in vacuo to yield 3-(4-aminophenyl)-1-methyl-1H-pyrazolo[3,4-d]pyrimidin-4-amine (ESI-MS m/z [M+H]+ found 241.0, calculated 241.1). To this reduced product, molar equivalents of 3-(trifluoromethyl)phenyl isocyanate (Sigma-Aldrich) were added dropwise in ice-cold $CH_2Cl_2$. The reaction proceeded until completion as judged by TLC, was concentrated in vacuo, resuspended in 50:50 $H_2O$—$CH_3CN$, and purified on a C18 column in $CH_3CN/H_2O$/0.1% TFA (1-100% gradient) to afford AD59 1-(4-(4-amino-1-methyl-1H-pyrazolo[3,4-d]pyrimidin-3-yl)phenyl)-3-(3-(trifluoromethyl)phenyl)urea (ESI-MS m/z [M+H]+ found 428.0, calculated 428.1).

Example 2.6

Synthesis of AD60: 1-(4-(4-amino-1-cyclopentyl-1H-pyrazolo[3,4-d]pyrimidin-3-yl)phenyl)-3-(3-(trifluoromethyl)phenyl)urea

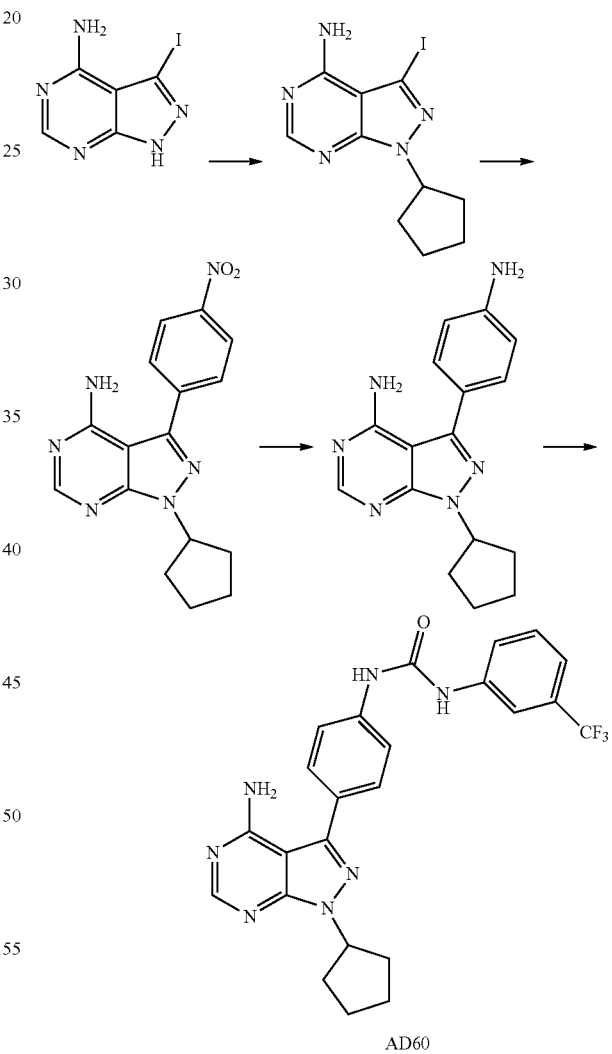

AD60

The intermediate 3-iodo-1H-pyrazolo[3,4-d]pyrimidin-4-amine) (0.5 g, 1.9 mmol; Apsel et al., 2008) was combined with cyclopentyl iodide (0.24 mL, 2.1 mmol), and 1.06 g $K_2CO_3$ in 20 mL DMF and heated to 45° C. under argon for 2 hours. The reaction was filtered to remove solid $K_2CO_3$. The filtrate was combined with brine, and the organic product was extracted in $CH_2Cl_2$ (3×50 mL). The combined organic layer was concentrated in vacuo and purified by silica gel chromatography (MeOH/chloroform; 5:95) to afford 1-cyclopentyl-3-iodo-1H-pyrazolo[3,4-d]pyrimidin-4-amine (ESI-MS m/z [M+H]+ found 330.0, calculated 330.0). 4-nitrophenyl boronic acid (190 mg, 1.1 mmol; Sigma-Aldrich) was coupled to 1-cyclopentyl-3-iodo-1H-pyrazolo[3,4-d]pyrimidin-4-amine (150 mg, 0.456 mmol) via the Suzuki reaction in 6 mL 1,2 methoxy ethane, 1 mL of saturated sodium carbonate, 1.65 mL EtOH, and 200 mg of polymer-bound tetrakis palladium. The reaction was stirred under argon for 12 hours at room temperature, filtered through Whatman paper to remove palladium, mixed with brine, extracted in chloroform, and the product was subsequently purified on silica in EtOAc and concentrated in vacuo. The purified solid 1-cyclopentyl-3-(4-nitrophenyl)-1H-pyrazolo[3,4-d]pyrimidin-4-amine (ESI-MS m/z [M+H]+ found 325.0, calculated 325.1; 100 mg, 0.31 mmol) was combined with zinc dust (605 mg, 9.25 mmol), 10 mL THF, and 0.35 mL HOAc for 12 hours at room temperature under argon. The reaction was filtered through Celite®, extracted with EtOAc, and concentrated in vacuo to yield 3-(4-aminophenyl)-1-cyclopentyl-1H-pyrazolo[3,4-d]pyrimidin-4-amine (ESI-MS m/z [M+H]+ found 295.0, calculated 295.2). To this reduced product, molar equivalents of 3-(trifluoromethyl)phenyl isocyanate (Sigma-Aldrich) were added dropwise in ice-cold $CH_2Cl_2$. The reaction proceeded until completion as judged by TLC, was concentrated in vacuo, resuspended in 50:50 $H_2O$—$CH_3CN$, and purified on a C18 column in $CH_3CN/H_2O$/0.1% TFA (1-100% gradient) to yield AD60 1-(4-(4-amino-1-cyclopentyl-1H-pyrazolo[3,4-d]pyrimidin-3-yl)phenyl)-3-(3-(trifluoromethyl)phenyl)urea (ESI-MS m/z [M+H]+ found 482.2, calculated 482.0).

Example 2.7

Synthesis of AD64

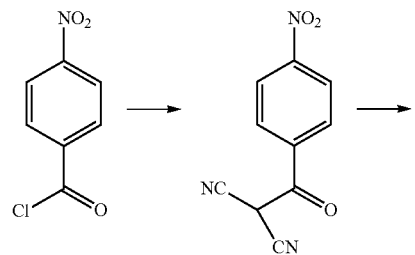

Synthesis of 5-amino-3-(4-nitrophenyl)-1H-pyrazole-4-carbonitrile. A 1000 mL round bottom flask was pre-cooled in an ice-water bath, to which a solution of melanonitrile (10.2 g, 0.154 mol) was mixed into a suspension of sodium hydride (6.72 g, 0.28 mol) in THF (100 mL). To this mixture, 4-nitrobenzoyl chloride (26 g, 0.14 mol; Sigma-Aldrich) was added slowly. After 20 minutes, the reaction was removed from the ice-water bath and left stirring for 2 hours. Dimethyl sulfate (16 mL, 0.168 mol) was then added with a syringe. The reaction vessel was placed into an oil bath at 90° C. and almost immediately afterwards a yellow solid began to form. The reaction was left at 90° C. for 2 hours. The reaction mixture was removed from the oil bath and allowed to cool to room temperature. Afterwards, hydrazine (7.5 mL, 0.154 mol) was added, and the reaction was left stirring for 60 minutes. 200 mL of brine and 100 mL of 2N HCl were added and separated from the organic layer. The aqueous phase was extracted two additional times with $CH_2Cl_2$. The organic phases were combined and concentrated in vacuo to yield a bright yellow solid. The solid was suspended in 100 mL EtOH, refluxed for 30 minutes, and the insoluble solid was collected by filtration, washed with room temperature EtOH, and dried to yield 5-amino-3-(4-nitrophenyl)-1H-pyrazole-4-carbonitrile (9.1 g, 28% yield).

Step 2

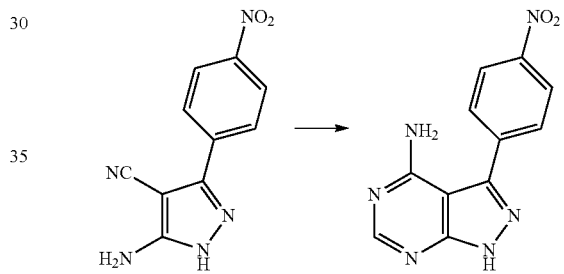

Synthesis of 3-(4-nitrophenyl)-1H-pyrazolo[3,4-d]pyrimidin-4-amine. A solution of formamide (30 mL) and 5-amino-3-(4-nitrophenyl)-1H-pyrazole-4-carbonitrile (7.25 g, 32 mmol) was heated to 160° C. overnight under an argon atmosphere. The reaction was cooled, and 25 mL of $H_2O$ was added. The resulting solid was recovered by filtration and rinsed with cold $H_2O$ to afford 3-(4-nitrophenyl)-1H-pyrazolo[3,4-d]pyrimidin-4-amine (5.9 g, 72% yield). ESI-MS m/z [M+H]+ found 257.5, calculated 257.2.

Step 3

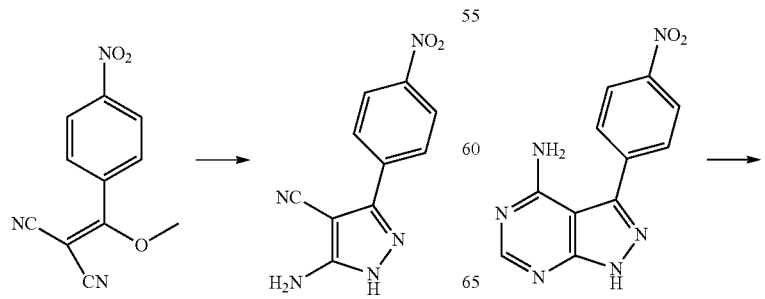

-continued

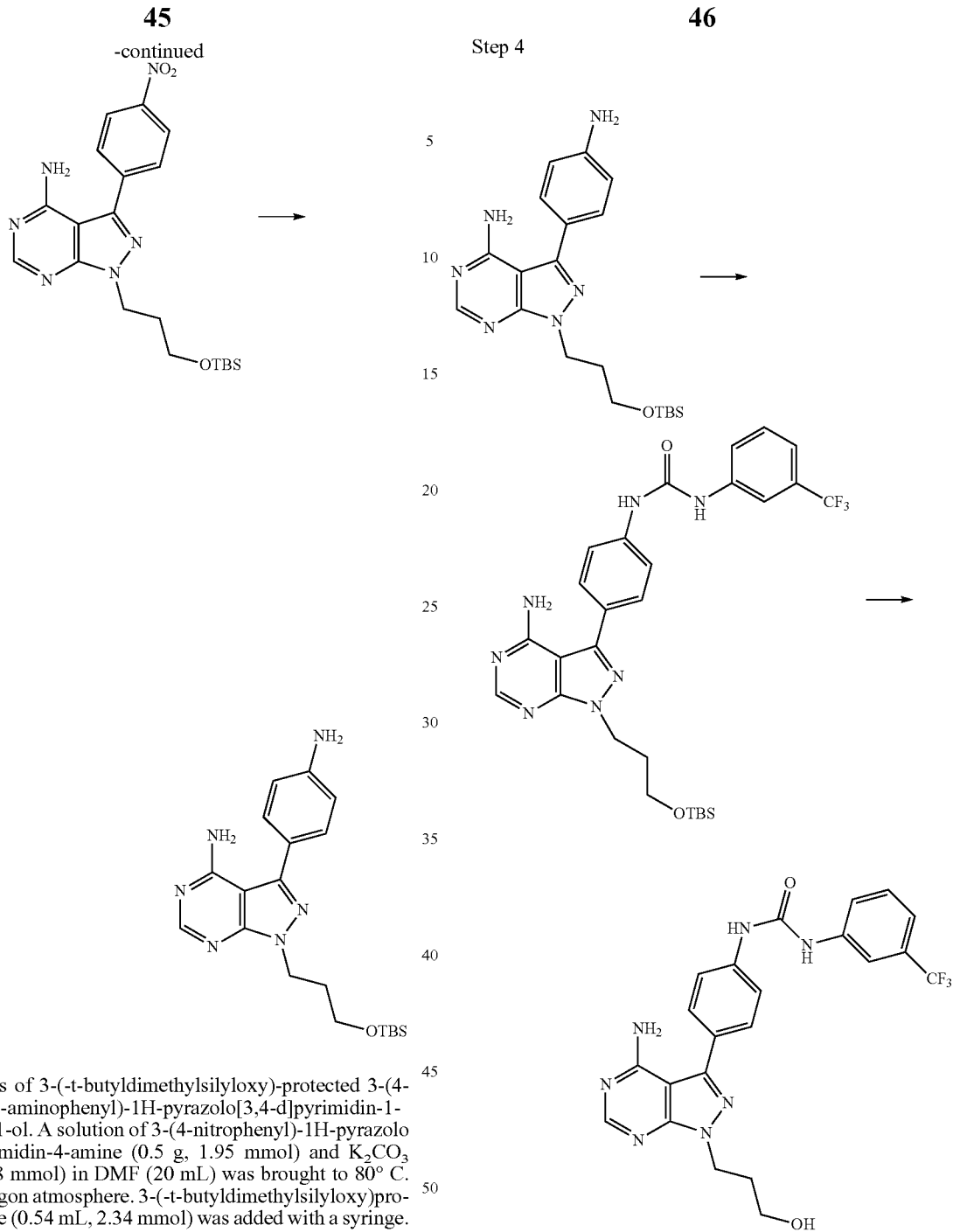

Step 4

Synthesis of 3-(-t-butyldimethylsilyloxy)-protected 3-(4-amino-3-(4-aminophenyl)-1H-pyrazolo[3,4-d]pyrimidin-1-yl)propan-1-ol. A solution of 3-(4-nitrophenyl)-1H-pyrazolo[3,4-d]pyrimidin-4-amine (0.5 g, 1.95 mmol) and $K_2CO_3$ (1.08 g, 7.8 mmol) in DMF (20 mL) was brought to 80° C. under an argon atmosphere. 3-(-t-butyldimethylsilyloxy)propyl bromide (0.54 mL, 2.34 mmol) was added with a syringe. The reaction mixture was left stirring for 3 hours. The reaction mixture was cooled and then filtered. The filtrate was concentrated in vacuo, but not to dryness. 14 mL of 0.1 sodium citrate was added causing an orange solid to form, which was collected by filtration to afford TBS-protected 3-(4-amino-3-(4-nitrophenyl)-1H-pyrazolo[3,4-d]pyrimidin-1-yl)propan-1-ol (0.79 g, 94% yield). ESI-MS m/z [M+H]+ found 429.6, calculated 429.6.

The orange solid (400 mg, 0.93 mmol) was combined with zinc dust (1.8 g, 28 mmol), 10 mL THF, and 1 mL HOAc for 12 hours at room temperature under an argon atmosphere. Following, the reaction mixture was filtered through Celite®, extracted with EtOAc, and concentrated in vacuo to afford TBS-protected 3-(4-amino-3-(4-aminophenyl)-1H-pyrazolo[3,4-d]pyrimidin-1-yl)propan-1-ol. ESI-MS m/z [M+H]+ found 399.7, calculated 399.6).

A solution of TBS-protected 3-(4-amino-3-(4-aminophenyl)-1H-pyrazolo[3,4-d]pyrimidin-1-yl)propan-1-ol (0.2 g, 0.51 mmol) in $CH_2Cl_2$ (10 mL) was cooled in an ice-water bath. To this, 3-(trifluoromethyl)phenyl isocyanate (0.072 mL, 0.5 mmol) diluted in $CH_2Cl_2$ (5 mL) was added dropwise. The reaction was allowed to warm to room temperature and left stirring for 12 hours. Formation of the urea intermediate was judged by TLC and LC-MS (ESI-MS m/z [M+H]+ found 586.8, calculated 587.7). Then 2N HCl (3 mL) was added into the reaction mixture. After 1 hour, water (25 mL) was added, and organic phases were extracted (2×50 mL $CH_2Cl_2$). Organic phases were concentrated in vacuo and purified using silica gel column chromatography (EtOAc, 100%) to afford final compound AD64. ESI-MS m/z [M+H]+ found 472.6, calculated 472.4.

Example 2.8

Synthesis of AD65

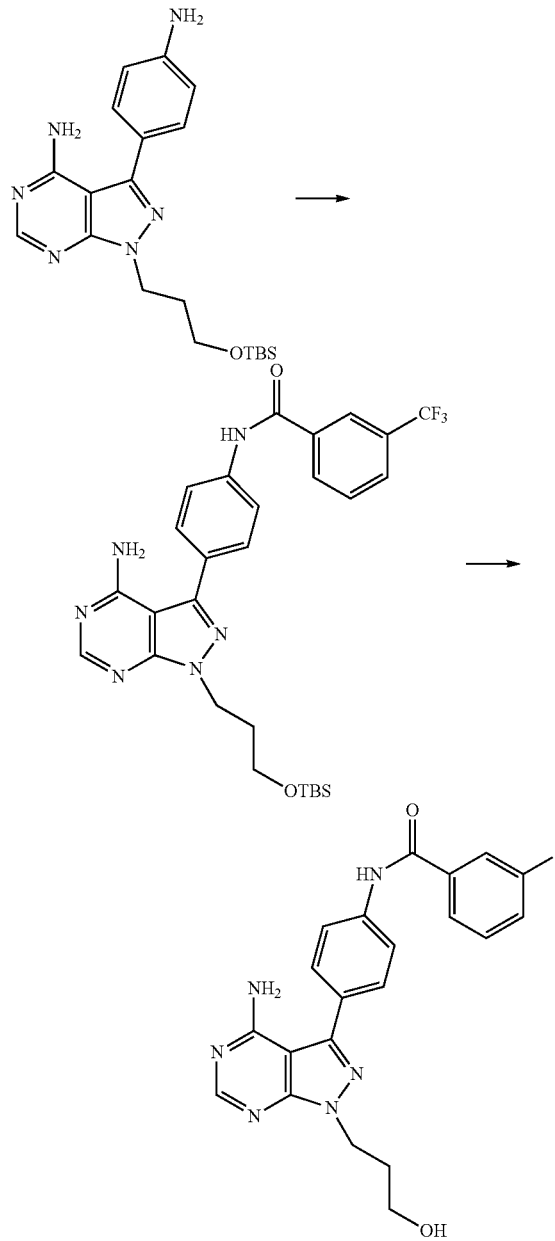

A solution of TBS-protected 3-(4-amino-3-(4-aminophenyl)-1H-pyrazolo[3,4-d]pyrimidin-1-yl)propan-1-ol (0.2 g, 0.51 mmol) in CH$_2$Cl$_2$ (10 mL) was cooled in an ice-water bath. To this, 3-(trifluoromethyl)benzoyl chloride (0.074 mL, 0.5 mmol; Sigma-Aldrich) diluted in CH$_2$Cl$_2$ (5 mL) was added dropwise. The reaction was allowed to warm to room temperature and left stirring for 3 hours. Formation of the benzamide intermediate was judged by TLC and LC-MS (ESI-MS m/z [M+H]+ found 571.7, calculated 571.2). Afterwards, 2N HCl (3 mL) was added directly to the reaction mixture and stirred for 1 hour. Water (25 mL) was added, and organic phases were extracted (2×CH$_2$Cl$_2$). Organic phases were concentrated in vacuo and purified using silica gel column chromatography (EtOAc, 100%) to afford final compound AD65. ESI-MS m/z [M+H]+ found 457.6, calculated 457.2.

Example 2.9

Synthesis of AD66: 1-(4-(4-amino-1-((S)-tetrahydrofuran-3-yl)-1H-pyrazolo[3,4-d]pyrimidin-3-yl)phenyl)-3-(3-(trifluoromethyl)phenyl)urea Step 1

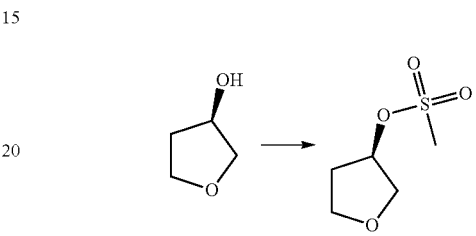

Synthesis of (R)-tetrahydrofuran-3-yl methanesulfonate. A solution of (R)-tetrahydrofuran-3-ol (1.1 g, 12.5 mmol) and triethylamine (13.6 mL, 97.5 mmol) in CH$_2$Cl$_2$ was cooled in an ice-water bath. To this, methanesulfonyl chloride (3.0 mL, 39 mmol) diluted in CH$_2$Cl$_2$ (10 mL) was added dropwise. The reaction was left stirring for 12 hours at room temperature. Water was added, and organic phases extracted in CH$_2$Cl$_2$ (3×50 mL), which were subsequently dried onto silica and purified by silica gel chromatography (50% EtOAc: Hexanes to 100% EtOAc gradient) to afford (R)-tetrahydrofuran-3-yl methanesulfonate (0.97 g, brown oil, 47% yield).

Step 2

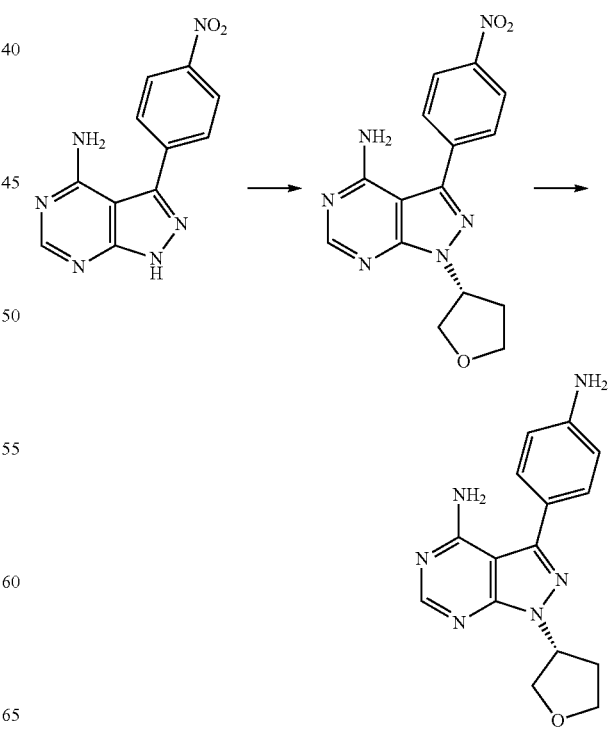

Synthesis of 3-(4-aminophenyl)-1-((S)-tetrahydrofuran-3-yl)-1H-pyrazolo[3,4-d]pyrimidin-4-amine. A solution of 3-(4-nitrophenyl)-1H-pyrazolo[3,4-d]pyrimidin-4-amine (0.5 g, 1.95 mmol), K$_2$CO$_3$ (1.08 g, 7.8 mmol), and (R)-tetrahydrofuran-3-yl methanesulfonate (0.389 g, 2.34 mmol) in DMF (20 mL) was brought to 80° C. under an argon atmosphere. The reaction mixture was left stirring for 3 hours, then cooled and filtered. The filtrate was concentrated in vacuo, but not to dryness. 20 mL of 0.1 sodium citrate was added causing a solid to form, which was collected by filtration to afford 1-((S)-tetrahydrofuran-3-yl)-3-(4-nitrophenyl)-1H-pyrazolo[3,4-d]pyrimidin-4-amine. ESI-MS m/z [M+H]+ found 327.6, calculated 327.3.

The resulting solid (250 mg, 0.77 mmol) was combined with zinc dust (1.5 g, 23 mmol), 30 mL THF, and 0.9 mL HOAc for 12 hours at room temperature under an argon atmosphere. Following, the reaction mixture was filtered through Celite® and concentrated in vacuo to afford 3-(4-aminophenyl)-1-((S)-tetrahydrofuran-3-yl)-1H-pyrazolo[3,4-d]pyrimidin-4-amine. ESI-MS m/z [M+H]+ found 297.2, calculated 297.1).

Step 3

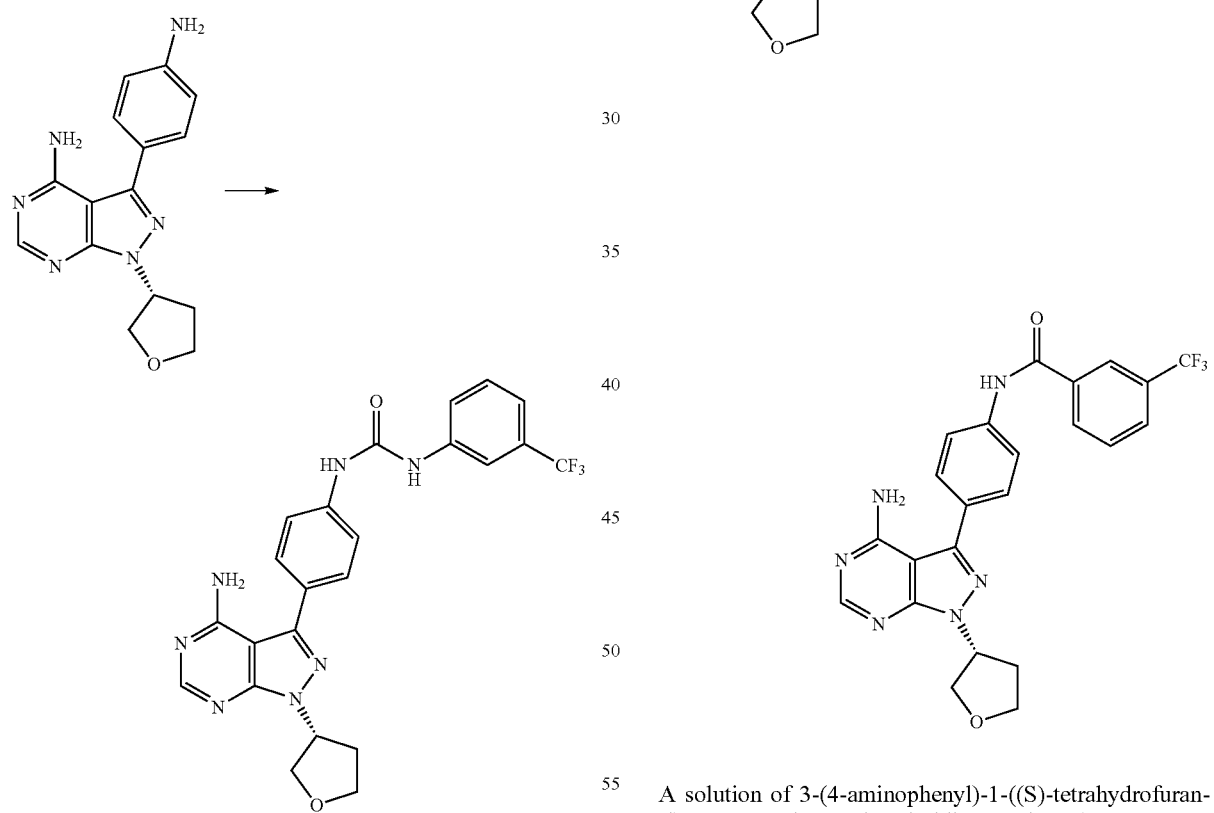

A solution of 3-(4-aminophenyl)-1-((S)-tetrahydrofuran-3-yl)-1H-pyrazolo[3,4-d]pyrimidin-4-amine (0.1 g, 0.34 mmol) in CH$_2$Cl$_2$ (10 mL) was cooled in an ice-water bath. To this, 3-(trifluoromethyl)phenyl isocyanate (0.047 mL, 0.34 mmol) diluted in CH$_2$Cl$_2$ (5 mL) was added dropwise. The reaction was allowed to warm to room temperature and left stirring for 12 hours. Reaction completion was judged by TLC and LC-MS. The reaction mixture was filtered, dried onto silica, and purified using silica gel column chromatography (50% EtOAc:Hexanes to 100% EtOAc gradient) to afford final compound AD66. ESI-MS m/z [M+H]+ found 484.4, calculated 484.2.

Example 2.10

Synthesis of AD67: N-(4-(4-amino-1-((S)-tetrahydrofuran-3-yl)-1H-pyrazolo[3,4-d]pyrimidin-3-yl)phenyl)-3-(trifluoromethyl)benzamide

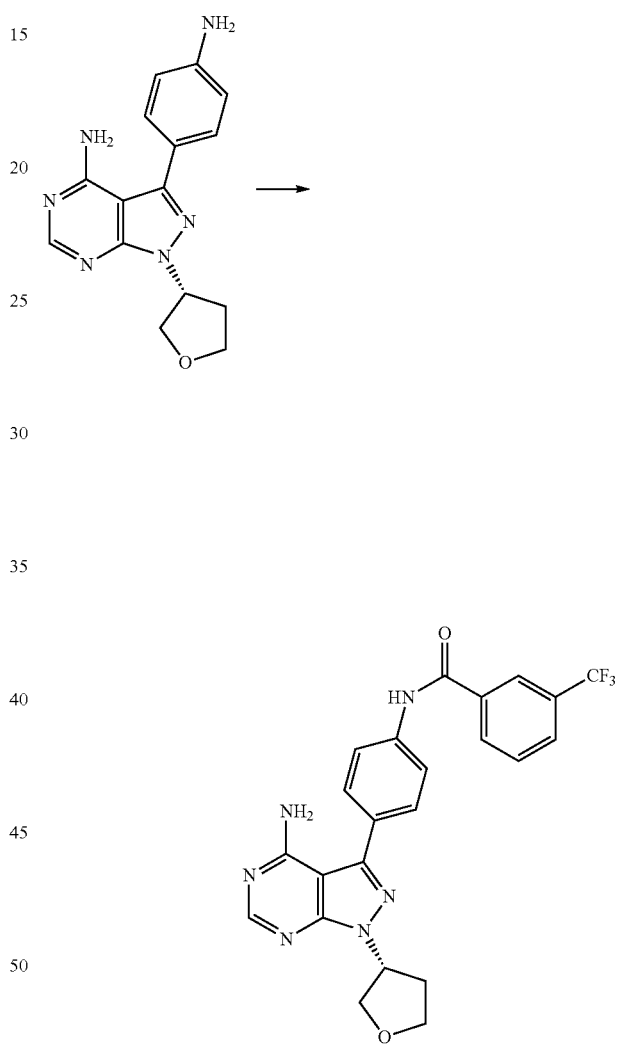

A solution of 3-(4-aminophenyl)-1-((S)-tetrahydrofuran-3-yl)-1H-pyrazolo[3,4-d]pyrimidin-4-amine (0.1 g, 0.34 mmol) in CH$_2$Cl$_2$ (10 mL) was cooled in an ice-water bath. To this, 3-(trifluoromethyl)benzoyl chloride (0.050 mL, 0.34 mmol) diluted in CH$_2$Cl$_2$ (5 mL) was added dropwise. The reaction was allowed to warm to room temperature and left stirring for 12 hours. The reaction proceeded until completion as judged by TLC and LC-MS, was concentrated in vacuo, resuspended in 50:50 H$_2$O—CH$_3$CN, and purified on a C18 column in CH$_3$CN/H$_2$O/0.1% TFA (1-100% gradient) to afford AD67. ESI-MS m/z [M+H]+ found 469.4, calculated 469.2.

Example 2.11

Synthesis of AD68: N-(4-(4-amino-1-((R)-tetrahydrofuran-3-yl)-1H-pyrazolo[3,4-d]pyrimidin-3-yl)phenyl)-3-(trifluoromethyl)benzamide Step 1

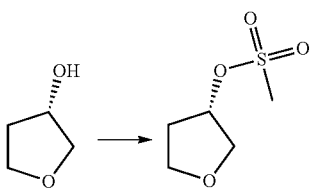

Synthesis of (S)-tetrahydrofuran-3-yl methanesulfonate. A solution of (S)-tetrahydrofuran-3-ol (1.0 g, 11 mmol) and triethylamine (9.4 mL, 86 mmol) in $CH_2Cl_2$ (20 mL) was cooled in an ice-water bath. To this, methanesulfonyl chloride (3.0 mL, 39 mmol) diluted in $CH_2Cl_2$ (10 mL) was added dropwise. The reaction was left stirring for 12 hours at room temperature. Water was added, and organic phases extracted in $CH_2Cl_2$ (3×50 mL), which were subsequently dried onto silica and purified by silica gel chromatography (50% EtOAc: Hexanes to 100% EtOAc gradient) to afford (S)-tetrahydrofuran-3-yl methanesulfonate (1.52 g, brown oil, 83% yield).

Step 2

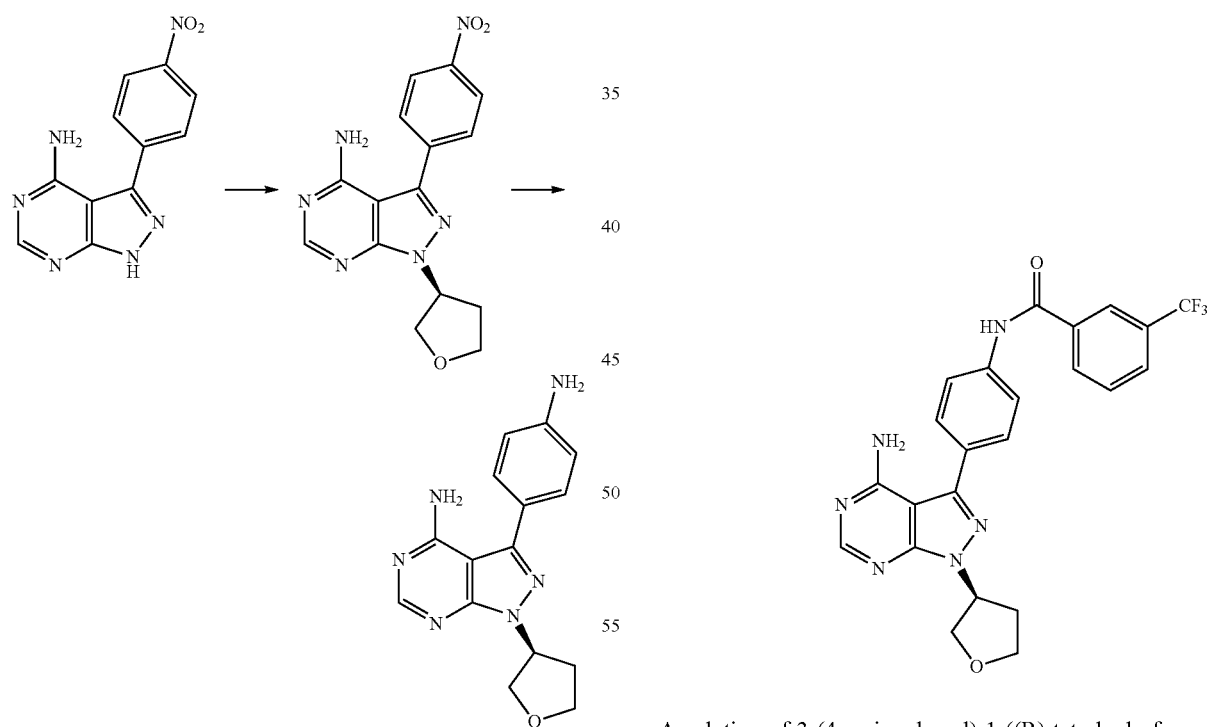

Synthesis of 3-(4-aminophenyl)-1-((R)-tetrahydrofuran-3-yl)-1H-pyrazolo[3,4-d]pyrimidin-4-amine. A solution of 3-(4-nitrophenyl)-1H-pyrazolo[3,4-d]pyrimidin-4-amine (0.5 g, 1.95 mmol), $K_2CO_3$ (1.08 g, 7.8 mmol), and (S)-tetrahydrofuran-3-yl methanesulfonate (0.389 g, 2.34 mmol) in DMF (20 mL) was brought to 80° C. under an argon atmosphere. The reaction mixture was left stirring for 3 hours, then cooled and filtered. The filtrate was concentrated in vacuo, but not to dryness. 20 mL of 0.1 sodium citrate was added causing a solid to form, which was collected by filtration to afford 1-((R)-tetrahydrofuran-3-yl)-3-(4-nitrophenyl)-1H-pyrazolo[3,4-d]pyrimidin-4-amine. ESI-MS m/z [M+H]+ found 327.6, calculated 327.3.

The resulting solid (250 mg, 0.77 mmol) was combined with zinc dust (1.5 g, 23 mmol), 30 mL THF, and 0.9 mL HOAc for 12 hours at room temperature under an argon atmosphere. Following, the reaction mixture was filtered through Celite® and concentrated in vacuo to afford 3-(4-aminophenyl)-1-((R)-tetrahydrofuran-3-yl)-1H-pyrazolo[3,4-d]pyrimidin-4-amine. ESI-MS m/z [M+H]+ found 297.5, calculated 297.1).

Step 3

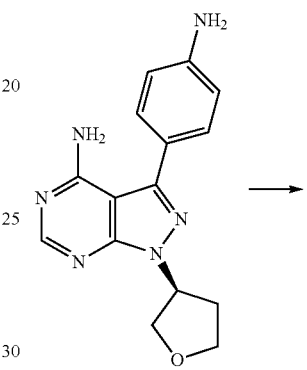

A solution of 3-(4-aminophenyl)-1-((R)-tetrahydrofuran-3-yl)-1H-pyrazolo[3,4-d]pyrimidin-4-amine (0.075 g, 0.25 mmol) in $CH_2Cl_2$ (10 mL) was cooled in an ice-water bath. To this, 3-(trifluoromethyl)benzoyl chloride (0.035 mL, 0.25 mmol) diluted in $CH_2Cl_2$ (5 mL) was added dropwise. The reaction was allowed to warm to room temperature and left stirring for 12 hours. The reaction proceeded until completion as judged by TLC and LC-MS, was concentrated in vacuo, resuspended in 50:50 $H_2O$—$CH_3CN$, and purified on a C18

Example 2.12

Synthesis of AD69: 1-(4-(4-amino-1-((R)-tetrahydrofuran-3-yl)-1H-pyrazolo[3,4-d]pyrimidin-3-yl)phenyl)-3-(3-(trifluoromethyl)phenyl)urea

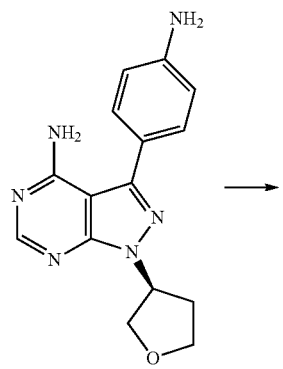

A solution of 3-(4-aminophenyl)-1-((R)-tetrahydrofuran-3-yl)-1H-pyrazolo[3,4-d]pyrimidin-4-amine (0.075 g, 0.25 mmol) in CH$_2$Cl$_2$ (10 mL) was cooled in an ice-water bath. To this, 3-(trifluoromethyl)phenyl isocyanate (0.035 mL, 0.25 mmol) diluted in CH$_2$Cl$_2$ (5 mL) was added dropwise. The reaction was allowed to warm to room temperature and left stirring for 12 hours. The reaction proceeded until completion as judged by TLC and LC-MS, was concentrated in vacuo, resuspended in 50:50 H$_2$O—CH$_3$CN, and purified on a C18 column in CH$_3$CN/H$_2$O/0.1% TFA (1-100% gradient) to afford AD69. ESI-MS m/z [M+H]+ found 484.4, calculated 484.4.

Example 2.13

Synthesis of AD70: N-(4-(4-amino-1-((S)-pyrrolidin-3-yl)-1H-pyrazolo[3,4-d]pyrimidin-3-yl)phenyl)-3-(trifluoromethyl)benzamide Step 1

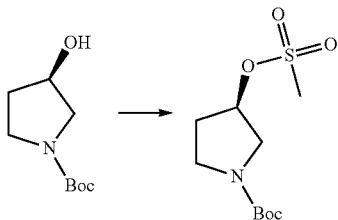 [SMILES: CC(C)(C)OC(=O)N1CC[C@@H](O)C1 ; CC(C)(C)OC(=O)N1CC[C@@H](OS(C)(=O)=O)C1]

Synthesis of (R)-1-(tert-butoxycarbonyl)pyrrolidin-3-yl methanesulfonate. A solution of (R)-tert-butyl 3-hydroxypyrrolidine-1-carboxylate (1.0 g, 5.3 mmol) and triethylamine (2.77 mL, 20 mmol) in CH$_2$Cl$_2$ (20 mL) was cooled in an ice-water bath. To this, methanesulfonyl chloride (1.15 mL, 15 mmol) diluted in CH$_2$Cl$_2$ (10 mL) was added dropwise. The reaction was left stirring for 12 hours at room temperature. Water was added, and organic phases extracted in CH$_2$Cl$_2$ (3×50 mL), which were subsequently dried onto silica and purified by silica gel chromatography (50% EtOAc: Hexanes to 100% EtOAc gradient) to afford (R)-1-(tert-butoxycarbonyl)pyrrolidin-3-yl methanesulfonate (1.53 g, brown oil, 100% yield).

Step 2

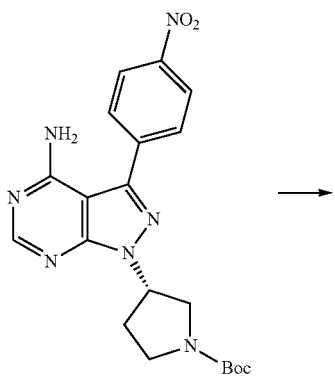

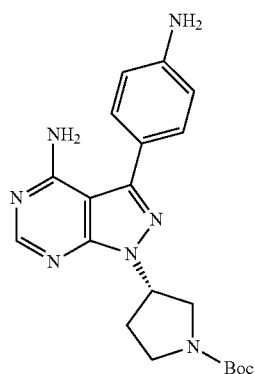

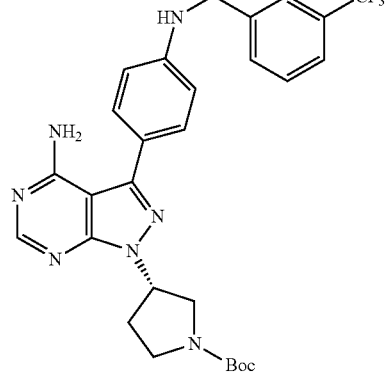

Synthesis of (S)-tert-butyl 3-(4-amino-3-(4-aminophenyl)-1H-pyrazolo[3,4-d]pyrimidin-1-yl)pyrrolidine-1-carboxylate. A solution of 3-(4-nitrophenyl)-1H-pyrazolo[3,4-d]pyrimidin-4-amine (0.5 g, 1.95 mmol), $K_2CO_3$ (1.08 g, 7.8 mmol), and (R)-1-(tert-butoxycarbonyl)pyrrolidin-3-yl methanesulfonate (0.62 g, 2.34 mmol) in DMF (20 mL) was brought to 80° C. under an argon atmosphere. The reaction mixture was left stirring for 6 hours, then cooled and filtered. The filtrate was concentrated in vacuo, but not to dryness. 20 mL of 0.1 sodium citrate was added causing a solid to form, which was collected by filtration to afford (S)-tert-butyl 3-(4-amino-3-(4-nitrophenyl)-1H-pyrazolo[3,4-d]pyrimidin-1-yl)pyrrolidine-1-carboxylate (0.43 g, 52% yield). ESI-MS m/z [M+H]+ found 426.7, calculated 426.2.

The resulting solid (330 mg, 0.78 mmol) was combined with zinc dust (1.5 g, 23 mmol), 30 mL THF, and 0.9 mL HOAc for 12 hours at room temperature under an argon atmosphere. Following, the reaction mixture was filtered through Celite®, mixed with water, and extracted with EtOAc. The organic phases were concentrated in vacuo to afford (S)-tert-butyl 3-(4-amino-3-(4-aminophenyl)-1H-pyrazolo[3,4-d]pyrimidin-1-yl)pyrrolidine-1-carboxylate. ESI-MS m/z [M+H]+ found 396.5, calculated 396.5).

Step 3

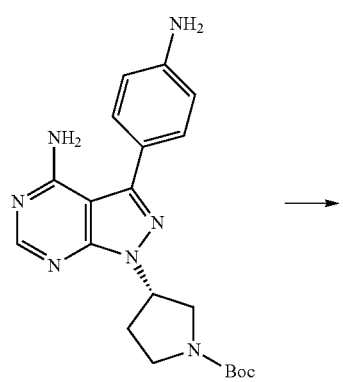

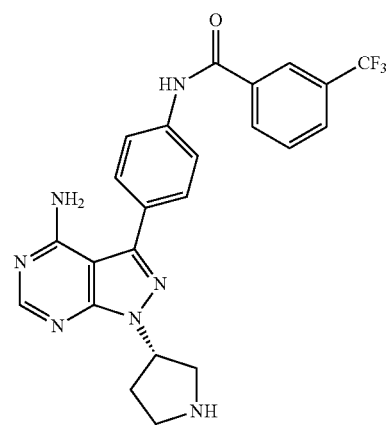

A solution of (S)-tert-butyl 3-(4-amino-3-(4-aminophenyl)-1H-pyrazolo[3,4-d]pyrimidin-1-yl)pyrrolidine-1-carboxylate (0.075 g, 0.17 mmol) in $CH_2Cl_2$ (10 mL) was cooled in an ice-water bath. To this, 3-(trifluoromethyl)benzoyl chloride (0.025 mL, 0.17 mmol) diluted in $CH_2Cl_2$ (5 mL) was added dropwise. The reaction was allowed to warm to room temperature and left stirring for 4 hours, yielding the benzamide derivative (ESI-MS m/z [M+H]+ found 568.5, calculated 568.6). Boc-deprotection was completed through the addition of formic acid (5 mL) and concentrated HCl (0.5 mL) added dropwise directly to the reaction mixture. The reaction mixture was left stirring for 12 hours and then was concentrated in vacuo, resuspended in 50:50 $H_2O$—$CH_3CN$, and purified on a C18 column in $CH_3CN/H_2O/0.1$% TFA (1-100% gradient) to afford AD70. ESI-MS m/z [M+H]+ found 468.5, calculated 468.2.

Example 2.14

Synthesis of AD71a 1-(4-(4-amino-1-((S)-pyrrolidin-3-yl)-1H-pyrazolo[3,4-d]pyrimidin-3-yl)phenyl)-3-(3-(trifluoromethyl)phenyl)urea

Example 2.15

Synthesis of AD71b (S)-3-(4-amino-3-(4-aminophenyl)-1H-pyrazolo[3,4-d]pyrimidin-1-yl)-N-(3-(trifluoromethyl)phenyl)pyrrolidine-1-carboxamide

Example 2.16

Synthesis of AD71c

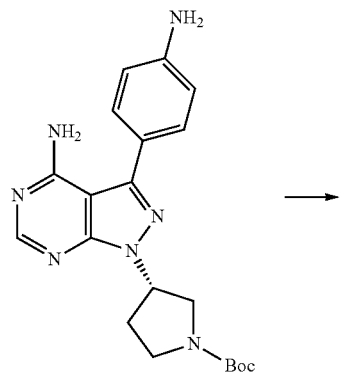

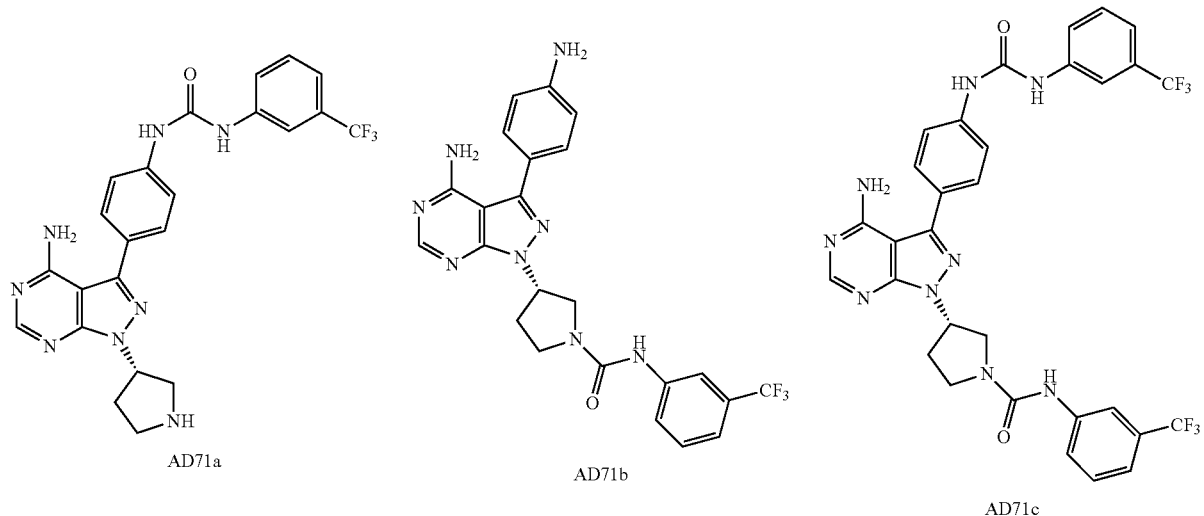

A solution of (S)-tert-butyl 3-(4-amino-3-(4-aminophenyl)-1H-pyrazolo[3,4-d]pyrimidin-1-yl)pyrrolidine-1-carboxylate (0.080 g, 0.17 mmol) in $CH_2Cl_2$ (10 mL) was cooled in an ice-water bath. To this, 3-(trifluoromethyl)phenyl isocyanate (0.026 mL, 0.19 mmol) diluted in $CH_2Cl_2$ (5 mL) was added dropwise. The reaction was allowed to warm to room temperature and left stirring for 6 hours. After, formic acid (5 mL) and concentrated HCl (0.5 mL) were added dropwise directly to the reaction mixture. Three major species were observed by LC-MS corresponding to AD71a, AD71b, and AD71c. The reaction mixture was left stirring for 12 hours and then was concentrated in vacuo, resuspended in 50:50 $H_2O$—$CH_3CN$, and purified on a C18 column in $CH_3CN$/$H_2O$/0.1% TFA (1-100% gradient) to afford AD71a (ESI-MS m/z [M+H]+ found 483.5, calculated 483.2), AD71b (ESI-MS m/z [M+H]+ found 483.5, calculated 483.2), and AD71c (ESI-MS m/z [M+H]+ found 670.5, calculated 670.2).

Example 2.17

Synthesis of AD72: N-(4-(4-amino-1-((R)-pyrrolidin-3-yl)-1H-pyrazolo[3,4-d]pyrimidin-3-yl)phenyl)-3-(trifluoromethyl)benzamide Step 1

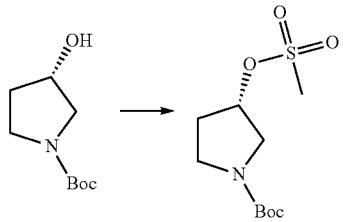 [SMILES: CC(C)(C)OC(=O)N1CC[C@H](O)C1 ; CC(C)(C)OC(=O)N1CC[C@H](OS(C)(=O)=O)C1]

Synthesis of (S)-1-(tert-butoxycarbonyl)pyrrolidin-3-yl methanesulfonate. A solution of (S)-tert-butyl 3-hydroxypyrrolidine-1-carboxylate (1.0 g, 5.3 mmol) and triethylamine (2.77 mL, 20 mmol) in $CH_2Cl_2$ (20 mL) was cooled in an ice-water bath. To this, methanesulfonyl chloride (1.15 mL, 15 mmol) diluted in $CH_2Cl_2$ (10 mL) was added dropwise. The reaction was left stirring for 12 hours at room temperature. Water was added, and organic phases extracted in $CH_2Cl_2$ (3×50 mL), which were subsequently dried onto silica and purified by silica gel chromatography (50% EtOAc: Hexanes to 100% EtOAc gradient) to afford (S)-1-(tert-butoxycarbonyl)pyrrolidin-3-yl methanesulfonate (0.97 g, brown oil, 70% yield).

Step 2

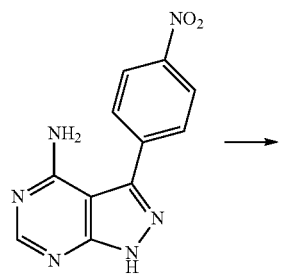

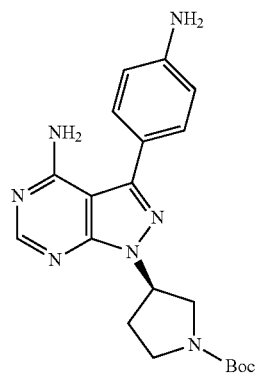

Synthesis of (R)-tert-butyl 3-(4-amino-3-(4-aminophenyl)-1H-pyrazolo[3,4-d]pyrimidin-1-yl)pyrrolidine-1-carboxylate. A solution of 3-(4-nitrophenyl)-1H-pyrazolo[3,4-d]pyrimidin-4-amine (0.5 g, 1.95 mmol), $K_2CO_3$ (1.08 g, 7.8 mmol), and (S)-1-(tert-butoxycarbonyl)pyrrolidin-3-yl methanesulfonate (0.62 g, 2.34 mmol) in DMF (20 mL) was brought to 80° C. under an argon atmosphere. The reaction mixture was left stirring for 2 hours, then cooled and filtered. The filtrate was concentrated in vacuo, but not to dryness. 20 mL of 0.1 sodium citrate was added causing a solid to form, which was collected by filtration to afford (R)-tert-butyl 3-(4-amino-3-(4-nitrophenyl)-1H-pyrazolo[3,4-d]pyrimidin-1-yl)pyrrolidine-1-carboxylate (0.38 g, 46% yield). ESI-MS m/z [M+H]+ found 426.5, calculated 426.2.

The resulting solid (300 mg, 0.70 mmol) was combined with zinc dust (1.4 g, 21 mmol), 30 mL THF, and 0.8 mL HOAc for 12 hours at room temperature under an argon atmosphere. Following, the reaction mixture was filtered through Celite® and concentrated in vacuo to afford (R)-tert-butyl 3-(4-amino-3-(4-aminophenyl)-1H-pyrazolo[3,4-d]pyrimidin-1-yl)pyrrolidine-1-carboxylate. ESI-MS m/z [M+H]+ found 396.5, calculated 396.5.

Step 3

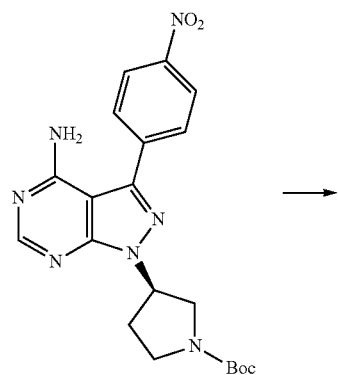

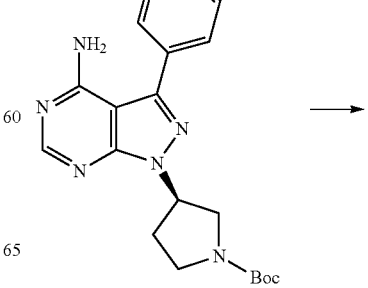

-continued

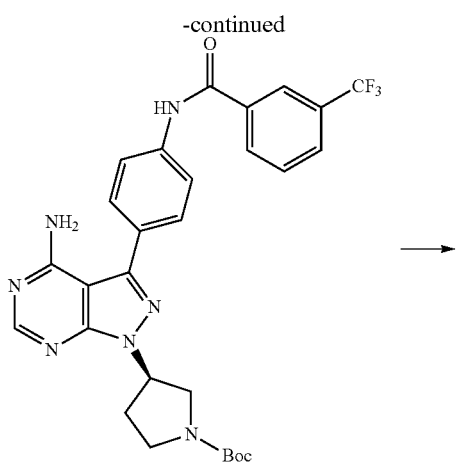

A solution of (R)-tert-butyl 3-(4-amino-3-(4-aminophenyl)-1H-pyrazolo[3,4-d]pyrimidin-1-yl)pyrrolidine-1-carboxylate (0.055 g, 0.14 mmol) in CH$_2$Cl$_2$ (10 mL) was cooled in an ice-water bath. To this, 3-(trifluoromethyl)benzoyl chloride (0.021 mL, 0.14 mmol) diluted in CH$_2$Cl$_2$ (5 mL) was added dropwise. The reaction was allowed to warm to room temperature and left stirring for 4 hours, yielding the benzamide derivative. Boc-deprotection was completed through the addition of formic acid (5 mL) and concentrated HCl (0.5 mL) added dropwise directly to the reaction mixture. The reaction mixture was left stirring for 12 hours and then was concentrated in vacuo, resuspended in 50:50 H$_2$O—CH$_3$CN, and purified on a C18 column in CH$_3$CN/H$_2$O/0.1% TFA (1-100% gradient) to afford AD72. ESI-MS m/z [M+H]+ found 468.5, calculated 468.2.

Example 2.18

Synthesis of AD73a 1-(4-(4-amino-1-((R)-pyrrolidin-3-yl)-1H-pyrazolo[3,4-d]pyrimidin-3-yl)phenyl)-3-(3-(trifluoromethyl)phenyl)urea Example 2.19

Synthesis of AD73b (R)-3-(4-amino-3-(4-aminophenyl)-1H-pyrazolo[3,4-d]pyrimidin-1-yl)-N-(3-(trifluoromethyl)phenyl)pyrrolidine-1-carboxamide Example 2.20

Synthesis of AD73c

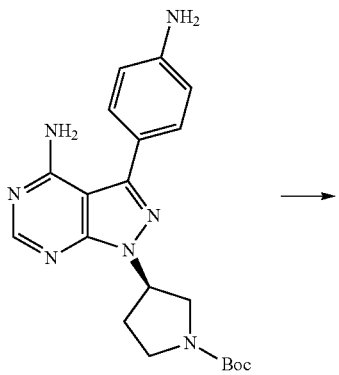

-continued

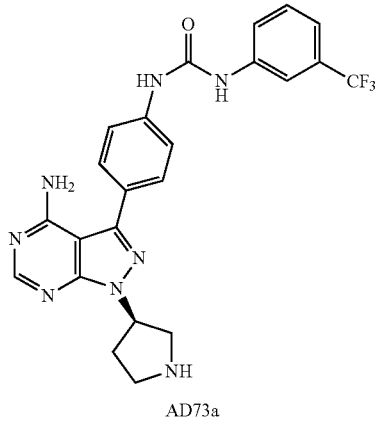
AD73a

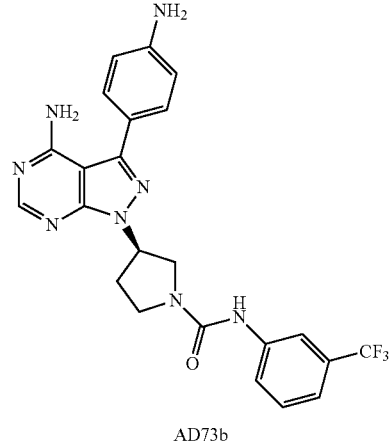
AD73b

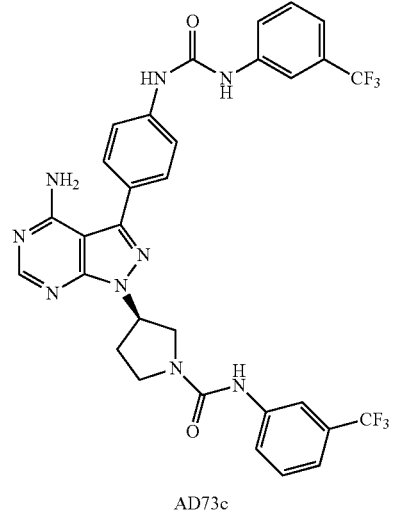
AD73c

A solution of (R)-tert-butyl 3-(4-amino-3-(4-aminophenyl)-1H-pyrazolo[3,4-d]pyrimidin-1-yl)pyrrolidine-1-carboxylate (0.090 g, 0.23 mmol) in CH$_2$Cl$_2$ (10 mL) was cooled in an ice-water bath. To this, 3-(trifluoromethyl)phenyl isocyanate (0.032 mL, 0.23 mmol) diluted in CH$_2$Cl$_2$ (5 mL) was added dropwise. The reaction was allowed to warm to room temperature and left stirring for 6 hours. After, formic acid (5 mL) and concentrated HCl (0.5 mL) were added dropwise directly to the reaction mixture. Three major species were observed by LC-MS corresponding to AD73a, AD73b, and AD73c. The reaction mixture was left stirring for 12 hours and then was concentrated in vacuo, resuspended in 50:50 H$_2$O—CH$_3$CN, and purified on a C18 column in CH$_3$CN/H$_2$O/0.1% TFA (1-100% gradient) to afford AD73a (ESI-MS m/z [M+H]+ found 483.5, calculated 483.2), AD73b (ESI-MS m/z [M+H]+ found 483.5, calculated 483.2), and AD73c (ESI-MS m/z [M+H]+ found 670.5, calculated 670.2).

Example 2.21

Synthesis of AD78

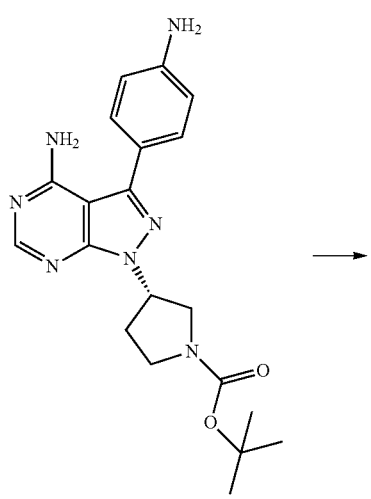

→

-continued

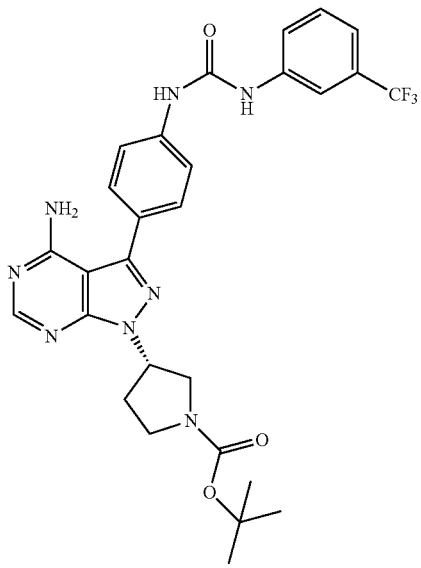

A solution of (S)-tert-butyl 3-(4-amino-3-(4-aminophenyl)-1H-pyrazolo[3,4-d]pyrimidin-1-yl)pyrrolidine-1-carboxylate (0.035 g, 0.09 mmol) in CH$_2$Cl$_2$ (10 mL) was cooled in an ice-water bath. To this, 3-(trifluoromethyl)phenyl isocyanate (0.012 mL, 0.09 mmol) diluted in CH$_2$Cl$_2$ (5 mL) was added dropwise. The reaction was allowed to warm to room temperature and left stirring for 6 hours. The reaction proceeded until completion as judged by TLC and LC-MS, was concentrated in vacuo, resuspended in 50:50 H$_2$O—CH$_3$CN, and purified on a C18 column in CH$_3$CN/H$_2$O/0.1% TFA (1-100% gradient) to afford AD78. ESI-MS m/z [M+H]+ found 583.5, calculated 583.2.

Example 2.22

Synthesis of AD79

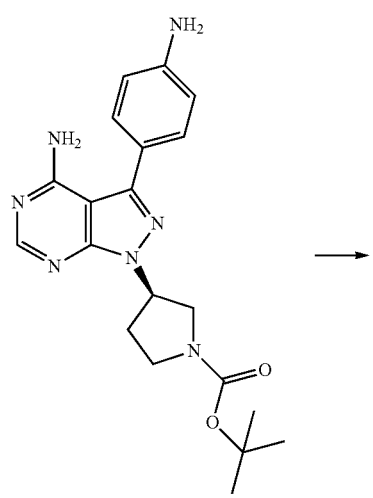

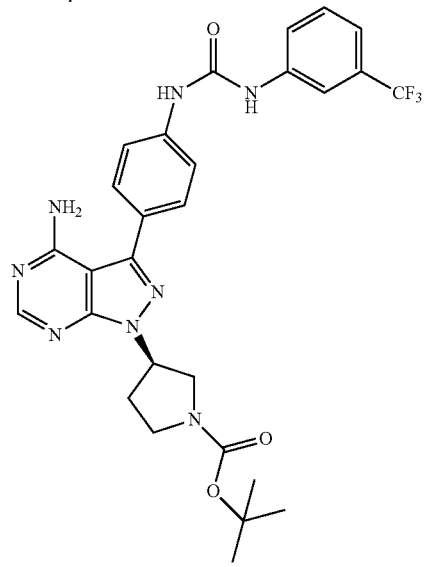

A solution of (R)-tert-butyl 3-(4-amino-3-(4-aminophenyl)-1H-pyrazolo[3,4-d]pyrimidin-1-yl)pyrrolidine-1-carboxylate (0.100 g, 0.25 mmol) in $CH_2Cl_2$ (10 mL) was cooled in an ice-water bath. To this, 3-(trifluoromethyl)phenyl isocyanate (0.035 mL, 0.25 mmol) diluted in $CH_2Cl_2$ (5 mL) was added dropwise. The reaction was allowed to warm to room temperature and left stirring for 6 hours. The reaction proceeded until completion as judged by TLC and LC-MS, was concentrated in vacuo, resuspended in 50:50 $H_2O$—$CH_3CN$, and purified on a C18 column in $CH_3CN/H_2O/0.1\%$ TFA (1-100% gradient) to afford AD79. ESI-MS m/z [M+H]+ found 583.5, calculated 583.2.

Example 3

In Vitro Inhibition Assay

Recombinant human Ire1-alpha (1 μM f/c) was mixed with reaction buffer, inhibitor solution in DMSO, and $^{32}P$-labeled RNA substrate having sequence 5'-UGC ACC UCU GCA GCA GGU GCA (SEQ ID NO:1). Reactions were conducted at 30° C. and initiated by adding the RNA to reaction pre-mix containing all the components minus the RNA. The final reaction contained: 20 mM HEPES pH 7, 70 mM NaCl, 2 mM $MgCl_2$, 5% glycerol, 4 mM DTT, 10% DMSO, 1 μM Ire1 and <1 nM 32P-labeled RNA. (The reaction mixture may be modified by using different components or concentrations, different RNA substrate, or different Ire1 protein construct.)

At time intervals (0 seconds, ~10 seconds, ~30 seconds, and ~3 minutes), 1 μl aliquots of reaction mixture were taken and quenched in 10 M Urea, 0.1% SDS. Samples were analyzed by denaturing polyacrylamide gel electrophoresis and quantified using Typhoon phosphorImager.

Inhibition was measured by the extent of RNA cleavage slowdown in the presence of inhibitor (0.3-100 μM) compared to reaction containing no inhibitors.

Reactions with Irestatin and exemplary compounds were conducted analogously. Irestatin was a gift obtained from the SPECS screen available as 5 mM solution in DMSO at UCSF small molecule discovery center.

Results are shown in the table below:

| Compound | Ire1 activity with yeast Ire1 | Ire1 activity with human Ire1 alpha |
|---|---|---|
| Control (no inhibitor) | 0.1149 | 0.085 |
| Imatinib | 0.061 | 0.155 |
| Sorafenib | 0.0683 | 0.03645 |
| BB5 | 5.00E−03 | 0.1247 |
| BB6 | 3.00E−03 | 0.1506 |
| AD36 | 1.05E−03 | 0.09575 |
| AD57 | 3.26E−03 | 0.05508 |
| AD60 | 2.42E−03 | 0.02258 |

In vitro cleavage of 32P-stem-loop RNA by human Ire1, with AD series of Ire1 modulators gave the following results:

| Compound | Ire1 activity |
|---|---|
| Control (no inhibitor) | 8.8310e-3 |
| AD59 | 3.0550e-3 |
| AD60 | 4.0180e-3 |
| AD64 | 6.9280e-4 |
| AD66 | 0.0107 |
| AD67 | 0.0100 |
| AD68 | 8.4550e-3 |
| AD69 | 0.0127 |
| AD70 | 9.0580e-3 |
| AD71a | 7.1670e-3 |
| AD71b | 5.5810e-3 |
| AD71c | 1.2650e-3 |
| AD72 | 6.4950e-3 |
| AD73a | 7.7190e-3 |
| AD73b | 8.9410e-3 |
| AD73c | 2.9310e-4 |

Example 4

UPR Activation/Inhibition

RNase Cleavage Assay.

RNA cleavage reactions were conducted at 30° C. in buffer containing 20 mM HEPES (pH 7.5), 70 mM NaCl, 2 mM ADP (pH 7.0), 2 mM Mg(OAc)$_2$, 5 mM DTT, 5% glycerol, less than 1 nM $^{32}$p-labeled RNA substrate, and 3 nM-20 M Ire1. Reaction solutions and buffers were designed using Biochem Lab Solutions 3.5. Reactions were prepared such that 1 µl of RNA was added to 9 µl of pre-warmed reaction mixture containing all components except RNA. Typically, 3-10 minute time courses were collected starting from 5 seconds for the first time point. At time intervals, 1 µl of solution was withdrawn from each reaction and mixed with 6 µl stop solution containing 10 M urea, 0.1% SDS, 0.1 mM EDTA, 0.05% xylene cyanol, and 0.05% bromophenol blue. The samples were separated by a denaturing 10% PAGE and exposed on a phosphor storage screen. The screens were scanned on a Storm or a Typhoon instrument and quantified using ImageQuant 5.0 or GelQuant.NET 1.4 programs. The data were plotted and fit in SigmaPlot 6.0.

RNA cleavage can be used to assess yIre1 activation as shown in the table below:

| Compound | Ire1 activity |
|---|---|
| Control (no inhibitor) | 0.000504 |
| AD36 | 0.000322 |
| AD59 | 0.0001 |
| AD60 | 4.04E−05 |

Example 5

Cell-Based IRE1 Inhibition Assay with Mouse Embryonic Fibroblasts (MEFS)

A cell-based assay of Ire1 inhibition was conducted on mouse embryonic fibroblasts (MEFS) isolated from a transgenic mouse expressing an XBP-1 luciferase reporter (Riken Research, Japan). The XBP-1 luciferase reporter produces a frameshift and production of luciferase only after splicing of the intron by activated IRE1. The effect of test compound or control on the action of UPR-inducing drugs or control (DMSO) in the cells was assayed.

Experimental.

Primary MEFs expressing an XBP1 luciferase reporter were plated in a 96 well white plate and allowed to recover overnight (80% confluency). Cells were induced with either thapsigargin (Tg) (600 nM) or tunicamycin (Tm) (2.5 ug/mL) in the absence or presence of compound AD73c (5 uM) and returned to incubation for 8 hrs. Control experiments employed no compound or Mitoxan (10 uM). Mitoxan, also known as mitoxantrone, is an FDA-approved anti-cancer agent. Luciferase activity was measured by the additional of 50 uL of One-Glo™ Luciferase Assay System (Promega), and the relative luminescence was quantitated using a luminometer (Analyst).

Results.

Figure 5:
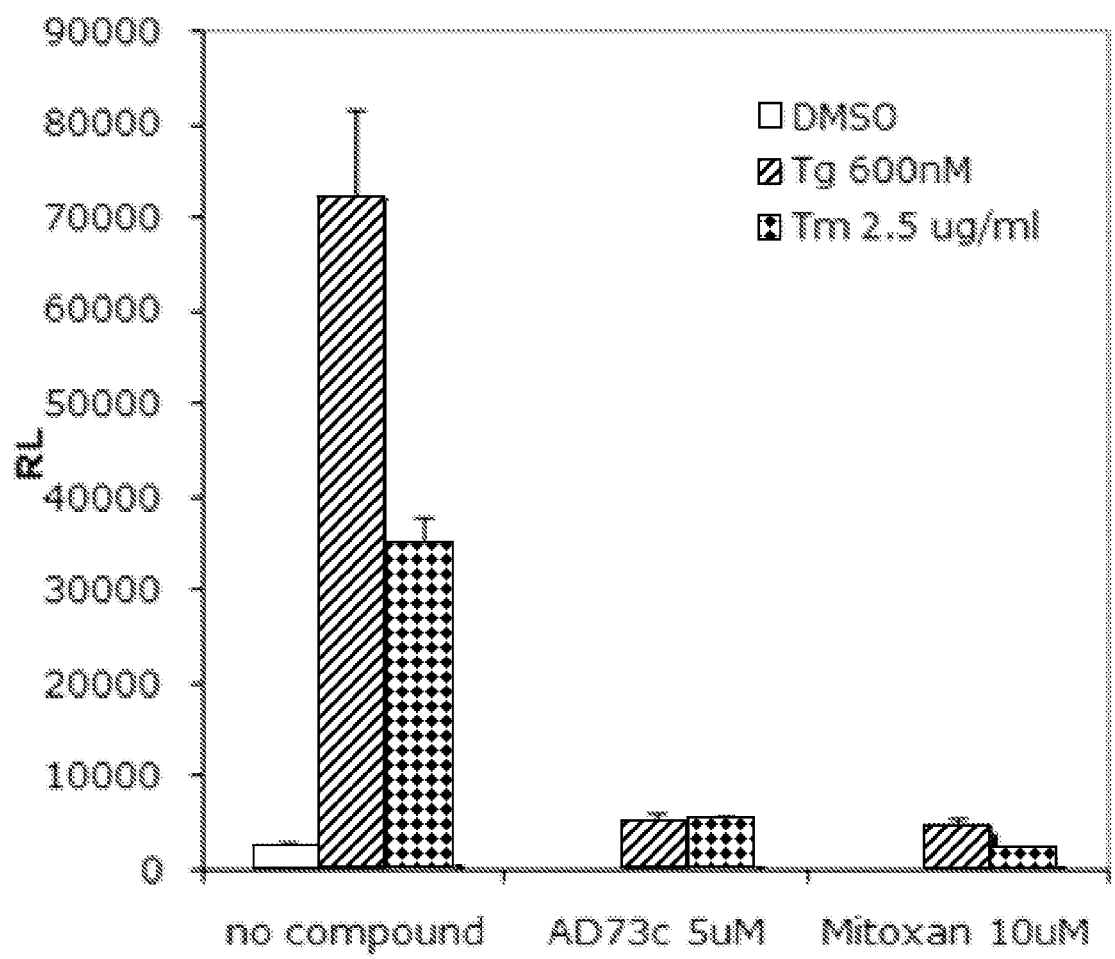
FIG. 5 depicts histogram results of cell-based Ire1 inhibition assay in mouse embryonic fibroblasts (MEFS). Primary MEFS isolated from a transgenic mouse expressing an XBP1 luciferase reporter were incubated with either thapsigargin (Tg) or tunicamycin (Tm) in the absence or presence of test compound or control. See Example 5. Treatment order in histogram (left to right): no compound, AD73c at 5 uM, mitoxan (10 uM). Incubation conditions (left to right): DMSO, Tg (600 nM), Tm (2.6 ug/mL). Legend: RL: relative luminosity (arbitrary units); DMSO (no fill); Tg (diagonal stripe); Mitoxan (diamond fill).

As depicted in the histogram of FIG. 5, the luminescence of luciferase expressed in Ire1-dependent assay was measured to assess Ire1 and UPR activity. As known in the art, higher luminescent intensity correlates with higher Ire1 and UPR activity, and lower intensity indicates inhibition of Ire1 and UPR. Under these assay conditions, compound AD73c was observed to strongly inhibit induction by both Tm and Tg.

Example 6

Cell-Based IRE1 Inhibition Assay with Human Fibroblasts (IMR90)

A cell-based assay of Ire1 inhibition was conducted on human diploid fibroblastic cells (IMR90) expressing an XBP-1 YFP (yellow fluorescent protein) reporter. The effect of test compound or control on UPR induction was assayed by fluorescence microscopy to measure the fluorescence of YFP expressed in a Ire1-dependent manner. The XBP1-YFP reporter only produces YFP after a frameshift produced by splicing of its intron by activated IRE1. As known in the art, higher fluorescence intensity means higher Ire1 and UPR activity. Conversely, lower fluorescence intensity means inhibitions of Ire1 and UPR.

Experimental.

IMR90 stable retroviral transductants expressing an XBP-1 YTP reporter were plated in a 96 well clear bottom plate and allowed to recover overnight (80% confluency). Cells were induced with Tg (100 uM) in the absence or presence (2 uM) of DMSO, Tg, bortezomib, MG132, Irestatin, AD71c, AD73c, AD58 or AD59, and the cells were returned to incubation for 8 hrs. Cells were washed with PBS (phosphate buffered saline) and imaged. Induction of the XBP1-YFP reported was assayed by fluorescence microscopy (GE Healthcare IN Cell Analyzer 2000). The number of YFP cells and the total number of cells, as judged by nuclear staining (Hoechst) were counted in each well. The number of YFP expressing cells was normalized to the total number of cells in each field.

Results.

Figure 6:
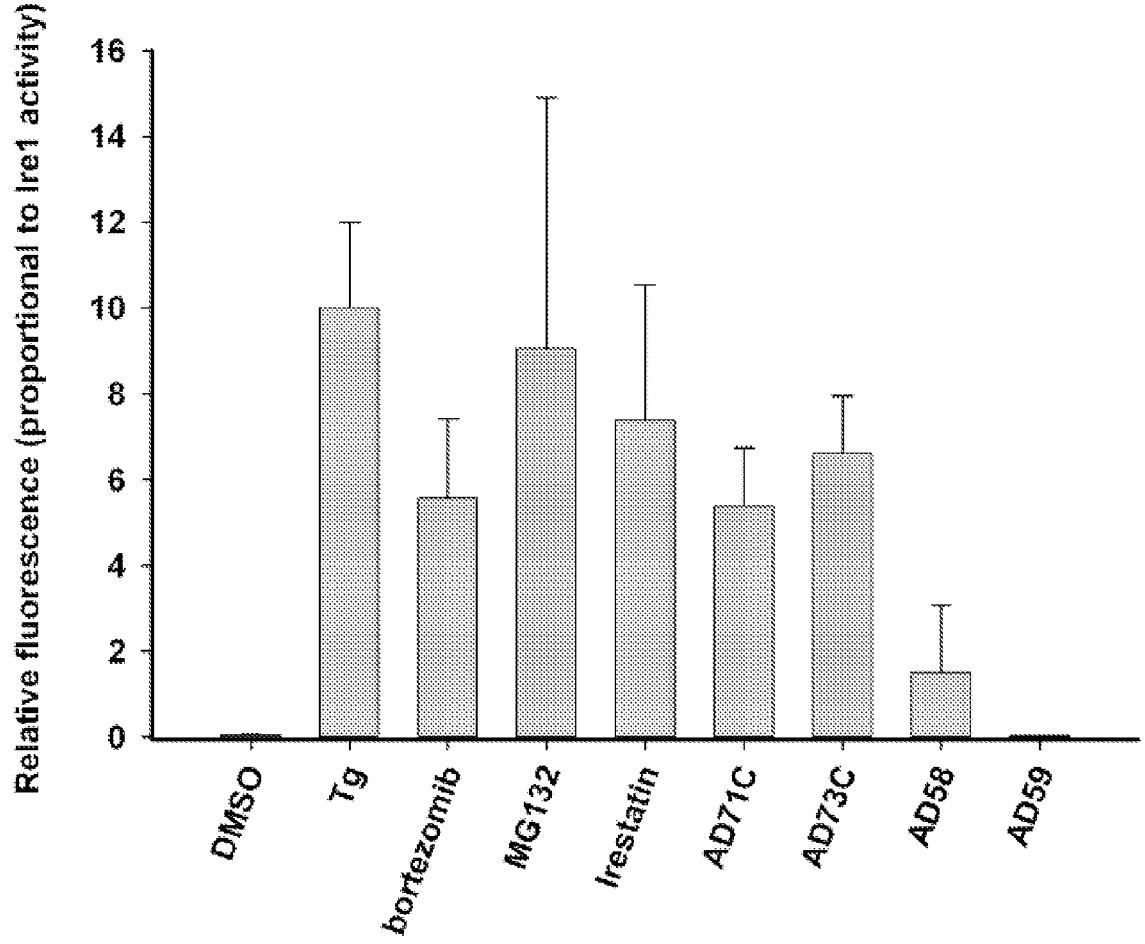
FIG. 6 depicts histogram results of cell-based Ire1 inhibition assay employing IMR90 human diploid fibroblastic cell line. IMR90 stable retroviral transductants expressing an XBP-1 YFP reporter were induced with Tg (100 nM) in the absence or presence of compounds (2 uM) indicated in the histogram. Induction of XBP-1 YFP reporter was assayed by fluorescence microscopy. See Example 6. Test compounds (left to right): DMSO; Tg; bortezomib; MG132; Irestatin; AD71c; AD73c; AD58; AD59. Ordinate: relative fluorescence (proportional to Ire1 activity.)

As depicted in the histogram of FIG. 6, compounds AD58 and even more strongly AD59 were observed to inhibit UPR induced in IMR90 cells by Tg under the assay conditions.

What is claimed is:

1. A method of decreasing Ire1 activity by contacting Ire1 with an effective amount of a compound having the formula:

wherein $Z^1$ and $Z^2$ are independently N;
$R^1$ and $R^2$ are independently hydrogen, substituted or unsubstituted alkyl, or substituted or unsubstituted heteroalkyl;
ring A is arylenyl;
ring B is aryl;
$R^3$ is independently halogen, —CN, —CF$_3$, —SH, —N(O), —N(O)$_2$, —NH$_2$, —C(O)H, —C(O)OH, —N=NH, —NH—C(O)H, —NH—C(O)—OH, —C(O)NH$_2$, —NHS$_2$H, —S(O)$_2$NH$_2$, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is independently halogen, —CN, —CF$_3$, —SH, —N(O), —N(O)$_2$, —NH$_2$, —C(O)H, —C(O)OH, —N=NH, —NH—C(O)H, —NH—C(O)—OH, —C(O)NH$_2$, —NHSO$_2$H, —SO$_2$NH$_2$, —OH, or unsubstituted C$_1$-C$_4$ alkyl or substituted or unsubstituted 2 to 4 membered heteroalkyl;
x is 0;
y is an integer from 0 to 5;
$L^1$ is a bond, substituted or unsubstituted alkylene, or substituted or unsubstituted heteroalkylene;
$L^2$ is —C(O)—;
$L^3$ is a bond or —N(H)—; and
$L^4$ is —NH—.

2. The method of claim 1, wherein $R^1$ and $R^2$ are independently hydrogen or C$_{1-10}$ unsubstituted alkyl.

3. The method claim 1, wherein ring A is unsubstituted phenylenyl.

4. The method of claim 1, wherein ring B is phenyl.

5. The method of claim 1, wherein $R^3$ is substituted or unsubstituted C$_{1-10}$ alkyl, substituted or unsubstituted C$_{3-8}$ cycloalkyl, or substituted or unsubstituted 5-6 membered heterocycloalkyl.

6. The method of claim 1, wherein $R^5$ is —CF$_3$, F, Br, Cl, I, NO$_2$, CH$_3$, C$_2$H$_5$, SH, OH, OMe, CN, SMe, NO, or C(O)H.

7. The method of claim 1, wherein y is 0 or 1.

8. The method of claim 1, wherein $L^1$ is a bond or substituted or unsubstituted alkylene.

9. The method of claim 1, wherein $L^3$ is a bond.

10. The method of claim 1, wherein $L^3$ is —N(H)—.

11. The method claim 1, wherein the compound is one of the formulae:

AD59
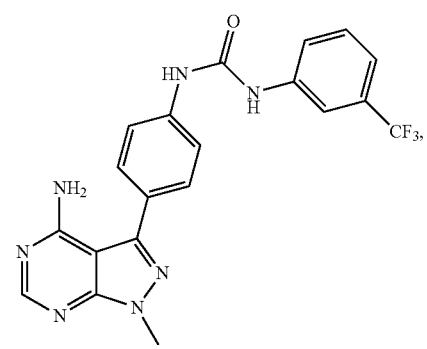
AD60
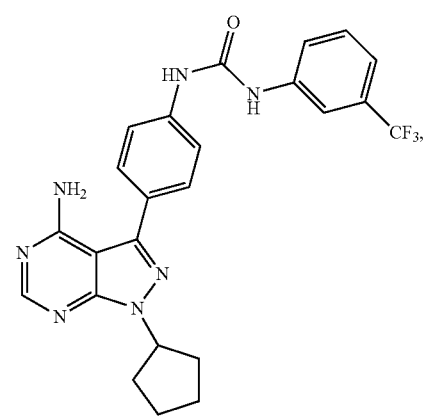
AD61
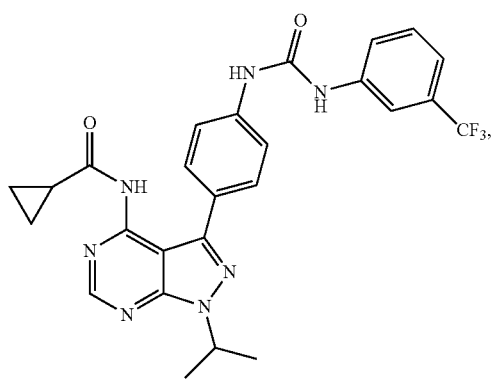
AD62
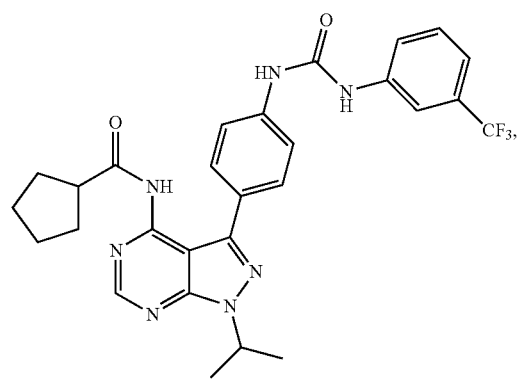
AD63
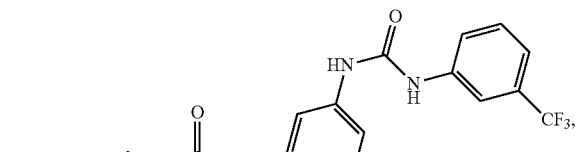
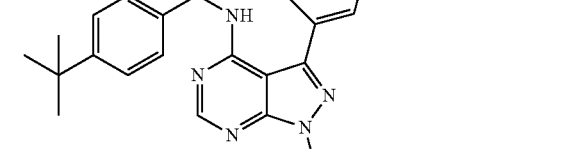
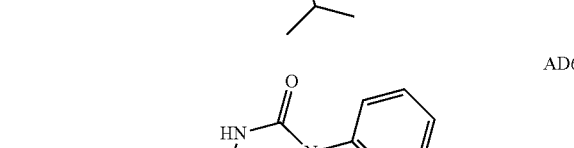
AD64
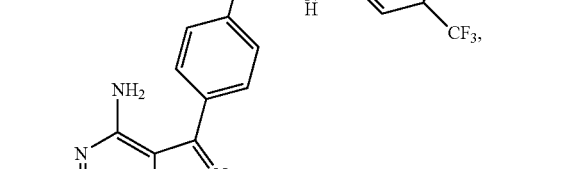
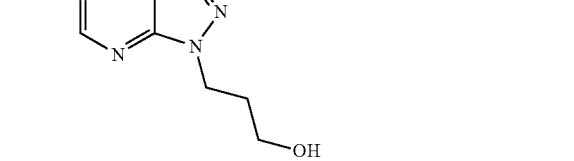
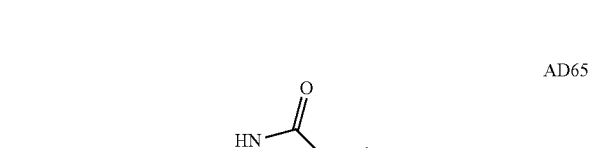
AD65
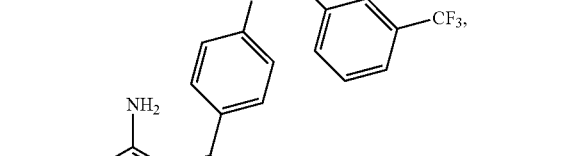
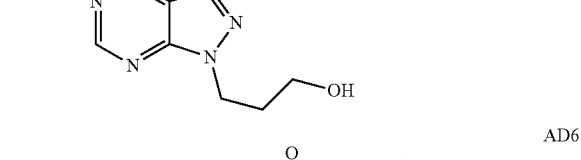
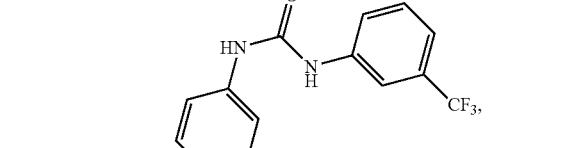
AD66
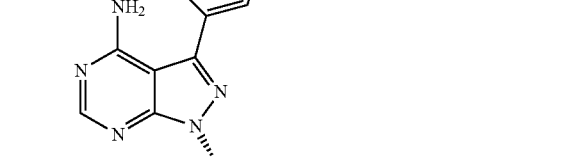
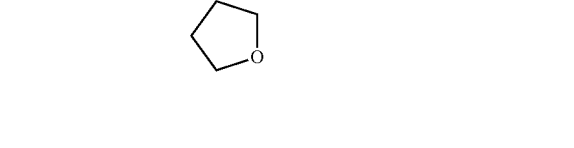

AD67
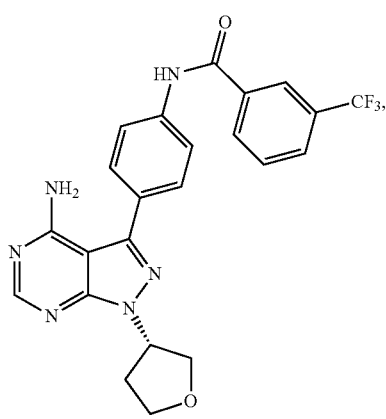
AD68
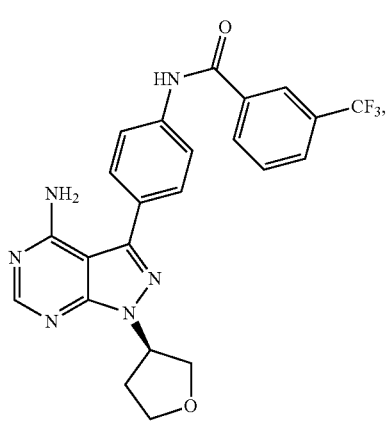
AD69
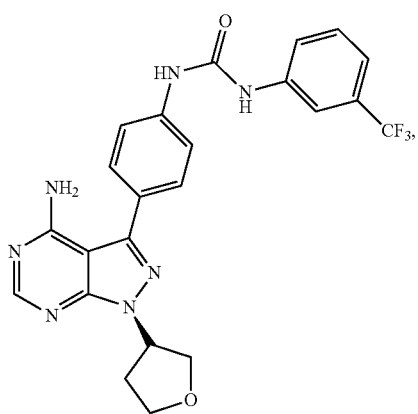
AD70
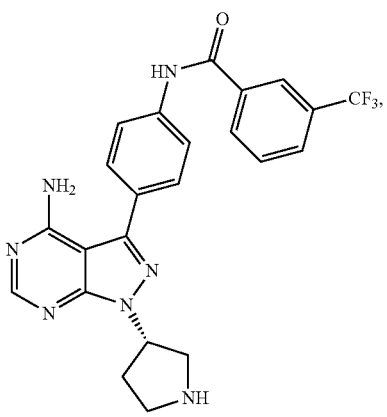
AD71b
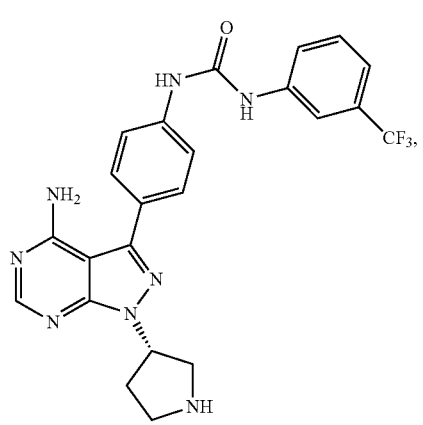
AD72
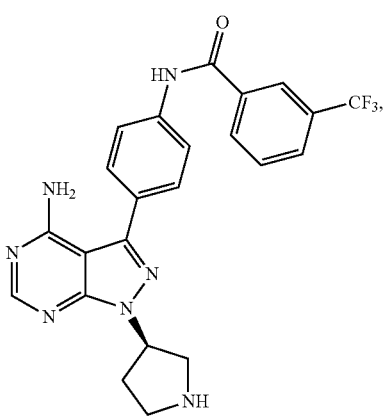

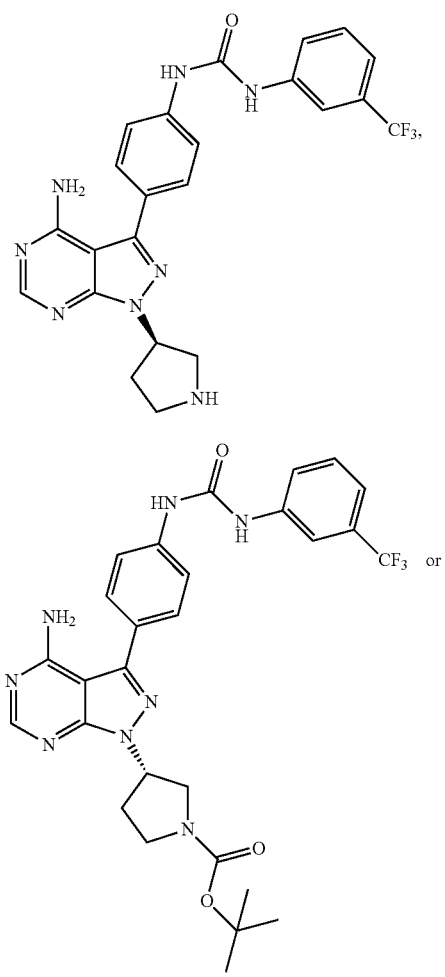

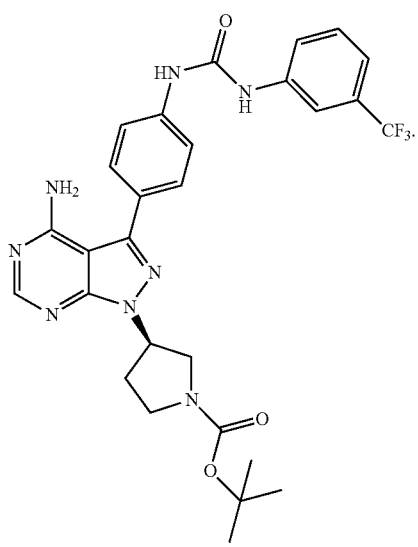

12. The method of claim 1, wherein the method comprises decreasing hIre1 activity.

13. The method claim 1, wherein $R^1$ and $R^2$ are hydrogen.

14. The method claim 1, wherein $L^1$ is a substituted or unsubstituted methylene.

15. The method claim 1, wherein $L^1$ is unsubstituted methylene.

16. The method of claim 1, wherein $R^3$ is unsubstituted $C_{1-4}$ alkyl, unsubstituted $C_{3-6}$ cycloalkyl, or unsubstituted 5-membered heterocycloalkyl.

* * * * *

SEQUENCE LISTING

```
<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: Synthetic RNA construct

<400> SEQUENCE: 1
ugcaccucug cagcaggugc a                                              21
```